(12) United States Patent
Dineen et al.

(10) Patent No.: US 9,079,902 B2
(45) Date of Patent: Jul. 14, 2015

(54) HETEROARYL SODIUM CHANNEL INHIBITORS

(75) Inventors: Thomas Dineen, Somerville, MA (US); Isaac E Marx, Cambride, MA (US); Hanh Nho Nguyen, Arlington, MA (US); Matthew Weiss, Boston, MA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 14/238,816

(22) PCT Filed: Aug. 16, 2012

(86) PCT No.: PCT/US2012/051100
§ 371 (c)(1),
(2), (4) Date: May 28, 2014

(87) PCT Pub. No.: WO2013/025883
PCT Pub. Date: Feb. 21, 2013

(65) Prior Publication Data
US 2014/0256707 A1    Sep. 11, 2014

Related U.S. Application Data

(60) Provisional application No. 61/524,691, filed on Aug. 17, 2011.

(51) Int. Cl.
*C07D 209/04* (2006.01)
*C07D 471/04* (2006.01)
*C07D 403/14* (2006.01)
*C07D 417/12* (2006.01)
*C07D 417/14* (2006.01)

(52) U.S. Cl.
CPC ............ *C07D 471/04* (2013.01); *C07D 403/14* (2013.01); *C07D 417/12* (2013.01); *C07D 417/14* (2013.01)

(58) Field of Classification Search
CPC .................................................. C07D 209/04
USPC .......................................... 548/490; 514/415
See application file for complete search history.

(56) References Cited

U.S. PATENT DOCUMENTS

2014/0371201 A1*  12/2014  Weiss et al. ............... 514/210.21

OTHER PUBLICATIONS

Berge, S.M., et al., "Pharmaceutical Salts," J Pharm Sci, 1977, 66: 1-19.
Cox J.J. et al., "An SCN9A channelopathy causes congenital inability to experience pain" Nature, 2006, 444:894-898.
Do & Bean, "Subthreshold Sodium Currents and Pacemaking of Subthalamic Neurons", Neuron, 2003, 39 :109-120.
Drenth, J.P.H. et al., "SCN9A mutations dene primary erythermalgia as a neuropathic disorder of ," J Invest Derm, 2005, 124:1333-1338.

Ettinger & Argoff, "Use of antiepileptic drugs for nonepilleptic conditions: psychiatric disorders and chronic pain", Neurotherapeutics, 2007, 4:75-83.
Fertleman C. R., et al., SCN9A mutations in paroxysmal extreme pain disorder: Neuron, 2006, 52:767-774.
Gillet L., et. al., "Voltage-gated sodium channel activity promotes cysteine cathespin-dependent" J Biol Chem 2009, 284:8680-8691.
Goldberg et al., "Loss-of-function mutations in the Nav1.7 gene underlie congenital indifference to pain," Clin Genet, 2007, 71:311-319.
Goldin, A. L., "Resurgence of sodium channel research," Ann Rev Physiol, 2001, 63:871-894.
Gonzalez, et al., Methods & Principles in Medicinal Chemistry, 2006, 29:168-192.
Hamann M., et. al., "Motor disturbances in mice with deficiency of sodium channel gene Scn8a", Exper Neuro, 2003 184 (2):830-838.
Haufe V., et. al., "The promiscuous nature of the cardiac sodium current", J Mol Cell Cardiol, 2007, 42(3):469-477.
Higuchi T. et al., "Pro-drugs as Novel Delivery Systems," vol. 14 of the A.C.S. 197 Symposium Series, and in Bioreversible Carriers in Drug Design, ed. (1974).

(Continued)

*Primary Examiner* — Niloofar Rahmani
(74) *Attorney, Agent, or Firm* — Elsa D. Lemoine

(57) ABSTRACT

The present invention provides compounds of Formula I or II, or pharmaceutically acceptable salts thereof, that are inhibitors of voltage-gated sodium channels, in particular Nav 1.7. The compounds are useful for the treatment of diseases treatable by inhibition of channels such as pain disorders. Also provided are pharmaceutical compositions containing compounds of the present invention.

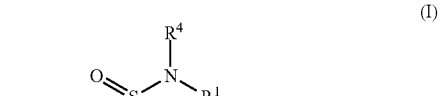

(I)

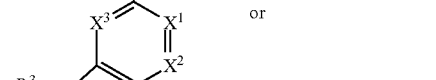

(II)

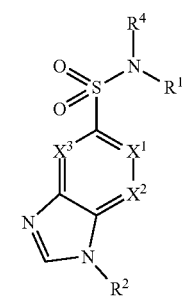

19 Claims, No Drawings

(56) References Cited

OTHER PUBLICATIONS

Hille B, Ion Channels of Excitable Membranes. Sinauer Associates, Inc.: Sunderland MA, 3rd Ed. 2001.

Johannessen L. C., CNS Drugs, "Antiepileptic drugs in non-epilepsy disorders:", 2008, 22(1)27-47.

Kim D. Y., et. al., "BACE1 regulates voltage-gated sodium channels and neuronal activity" Nat Cell Biol, 2007, 9(7):755-764.

McKinney B. C, et. al., "Exaggerated emotional behaviour in mice heterozygous" Genes Brain Behav, 2008, 7(6):629-638.

Morinville et al., "Distribution of the voltage-gated sodium channel Nav1.7 in the rat:", J Comp Neurol, 2007, 504:680-689.

Puopolo et al., "Roles of subthreshold calcium current and sodium current in spontaneous firing of" J. Neuroscience, 2007, 27:645-656.

Roche E.B., American Pharmaceutical Association and Pergamon Press, 1987.

Waxman, "Axonal conduction and injury in multiple sclerosis: the role of sodium channels" Nature Neuroscience, 2006, 7:932-941.

Wood, J. N. and, Boorman, J. "Voltage-gated sodium channel blockers;", Curr. Top Med. Chem. 2005 20055:529-537.

Woodruff-Pak D. S., et. al., "Inactivation of sodium channel Scn8A (Nav1.6)", Behav Neuroscience, 2006, 120(2):229-240.

Yang, Y., et al., "Mutations in SCN9A, encoding a sodium channel alpha subunit, in patients with primary erythermalgia," J. Med. Genet. 2004, 41:171-174.

* cited by examiner

HETEROARYL SODIUM CHANNEL INHIBITORS

This application is a US national stage application under 35 U.S.C. 371 of International Application No. PCT/US2012/051100, having an international filing date of Aug. 16, 2012, which claims the benefit of, and priority to, U.S. Provisional Application No. 61/524,691, filed on Aug. 17, 2011, which is hereby incorporated herein by reference in its entirety.

FIELD OF THE INVENTION

The present invention provides compounds that are inhibitors of voltage-gated sodium channels (Nav), in particular Nav 1.7, and are useful for the treatment of diseases treatable by inhibition of sodium channels such as pain disorders. Also provided are pharmaceutical compositions containing compounds of the present invention.

BACKGROUND OF THE INVENTION

Chronic pain by definition involves abnormal electrical spiking of neurons in the pain pathways: peripheral sensory neurons, spinal cord neurons, neurons in the pain matrix of the brain (e.g., somatosensory cortex, insular cortex, anterior cingular cortex), and/or neurons in brainstem. Although firing of these neurons is modulated and governed by many different receptors, enzymes, and growth factors, in most neurons the fast upstroke of the electrical spike is produced by entry of sodium ions through voltage-gated sodium channels (Hille B, Ion Channels of Excitable Membranes. Sinauer Associates, Inc.: Sunderland Mass., 3$^{rd}$ Ed. 2001). There are nine different isoforms of voltage-gated sodium channel (Nav 1.1-Nav 1.9), and they have distinct expression patterns in tissues including neurons and cardiac and skeletal muscle (Goldin, A. L, "Resurgence of sodium channel research," *Ann Rev Physiol* 63:871-894, 2001; Wood, J. N. and, Boorman, J. "Voltage-gated sodium channel blockers; target validation and therapeutic potential," *Curr. Top Med. Chem.* 5:529-537, 2005). Nonselective sodium channel inhibitors such as lidocaine, mexiletine, and carbamazepine show clinical efficacy in chronic pain, including neuropathic pain, but they are limited in dose and in use, likely due to effects on sodium channels outside the pain pathway.

Recent evidence from several independent genetic studies has shown that the tetrodotoxin-sensitive voltage-gated sodium ion channel Nav 1.7 (SCN9A) is required to sense pain. Rare genetic forms of severe chronic pain, Primary Erythromelalgia and Paroxysmal Extreme Pain Disorder, result from mutations that increase the activity of Nav 1.7 (Fertleman C. R., Baker M. D., Parker K. A., Moffatt S., et al., "SCN9A mutations in paroxysmal extreme pain disorder: allelic variants underlie distinct channel defects and phenotypes," *Neuron* 52:767-774, 2006; Yang Y., Wang Y., Li S, et al., "Mutations in SCN9A, encoding a sodium channel alpha subunit, in patients with primary erythermalgia," *J. Med. Genet.* 41:171-174, 2004; Drenth J. P. H., to Morsche R. H. M., Guillet G., Taieb A., et al., "SCN9A mutations define primary erythermalgia as a neuropathic disorder of voltage gated sodium channels," *J Invest Dermatol* 124:1333-1338). Conversely, two separate clinical studies have determined that the root cause of the genetic disorder Congenital Indifference to Pain (CIP) is a loss of function of Nav 1.7 via mutations that truncate the protein and destroy function (Cox J. J., Reimann F, Nicholas A. K., et al. "An SCN9A channelopathy causes congenital inability to experience pain," *Nature* 444:894-898, 2006; Goldberg Y. P., MacFarlane J., MacDonald M. L., Thompson J., et al. "Loss-of-function mutations in the Nav1.7 gene underlie congenital indifference to pain in multiple human populations," *Clin Genet.* 71:311-319, 2007). The disorder is inherited in Mendelian recessive manner with 100% penetrance. The phenotype associated with CIP is extreme: affected individuals are reported to have experienced painless burns, childbirth, appendicitis, and bone fractures, as well as to have insensitivity to clinical measures of pain such as pinprick or tendon pressure. Yet sensory, motor, autonomic, and other measured functions are normal, with the only reported abnormality being anosmia (inability to smell). These studies indicate that among the many possible targets in the pain pathway, Nav 1.7 governs one or more control points critical for pain perception. Accordingly, a therapeutic agent that inhibits Nav 1.7 should effectively treat pain in humans. The present invention provides compounds that are inhibitors of Nav 1.7.

SUMMARY OF THE INVENTION

In embodiment 1, the present invention provides compounds of Formula I or II, or pharmaceutically acceptable salts thereof,

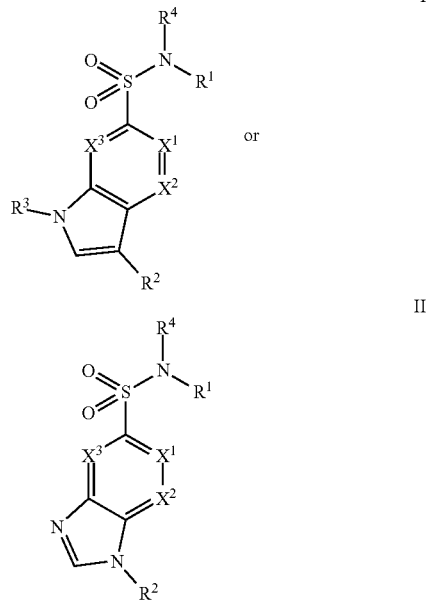

wherein:
each $X^1$, $X^2$ or $X^3$ is independently $CR^a$ or N;
each $R^a$ is independently hydrogen, halo, $C_{1-6}$alkyl, —$OC_{1-6}$alkyl, or —CN;
each $R^b$ is independently hydrogen or $C_{1-6}$alkyl;
$R^1$ is a five or six membered heteroaryl or heterocycloalkyl group having from one to four heteroatoms independently selected from O, N or S, or a five or six membered aryl or cycloalkyl group, where the heteroaryl, heterocycloalkyl, aryl or cycloalkyl group is unsubstituted or substituted with from one to four substituents selected from halo or $C_{1-6}$alkyl, —$OC_{1-6}$alkyl or —$NR^bR^b$;
$R^2$ is a five to ten membered cycloalkyl, aryl or heteroaryl group, the heteroaryl group having from one to four heteroatoms independently selected from O, N or S, and where the aryl or heteroaryl group is unsubstituted or substituted with from one to four substituents independently selected from —CF$_3$, —CHF$_2$, —CF$_2$H, —OC$_{1-6}$alkyl, —OCF$_3$, —C$_{1-6}$alkyl, halo, —C≡C—R$^b$, —CN, —NR$^b$R$^b$, —S(=O)$_2$C$_{1-6}$alkyl, or Y;

Y is a five or six membered heteroaryl or heterocycloalkyl group having from one to four heteroatoms independently selected from O, N or S, or an aryl or cycloalkyl group, which heteroaryl, heterocycloalkyl, aryl or cycloalkyl group is unsubstituted or substituted with from one to four substituents independently selected from —CF$_3$, —CHF$_2$, —CF$_2$H, —OC$_{1-6}$alkyl, —OCF$_3$, C$_{1-6}$alkyl, halo, —C≡C—R$^b$, —CN, —NR$^b$R$^b$, —S(=O)$_2$C$_{1-6}$alkyl, —C(=O)C$_{1-6}$alkyl or Z;

Z is a three to six membered heterocycloalkyl group having from one to four heteroatoms independently selected from O, N or S;

R$^3$ is hydrogen, C$_{1-6}$alkyl, —C(=O)C$_{1-6}$alkyl, —C(=O)OC$_{1-6}$alkyl, or —S(=O)$_2$C$_{1-6}$alkyl; and R$^4$ is hydrogen or C$_{1-6}$alkyl, provided that the compound of Formula I is not 1-methyl-3-(2-(1-methyl-1H-pyrazol-5-yl)-4-(trifluoromethyl)phenyl)-N-2-pyrimidinyl-1H-indole-6-sulfonamide;

3-(1-(3-azetidinyl)-1H-pyrazol-3-yl)-1-methyl-N-1,2,4-thiadiazol-5-yl-1H-indole-6-sulfonamide;

3-(2-(5-acetyl-2-thiophenyl)-4-(trifluoromethyl)phenyl)-1-methyl-N-1,2,4-thiadiazol-5-yl-1H-indole-6-sulfonamide;

1-methyl-3-(5-phenyl-2-thiophenyl)-N-1,2,4-thiadiazol-5-yl-1H-indole-6-sulfonamide;

N-(4-((1R)-1-methoxyethyl)-1,3-thiazol-2-yl)-1-methyl-3-(2-(1-methyl-1H-pyrazol-5-yl)-4-(trifluoromethyl)phenyl)-1H-indole-6-sulfonamide, N-(4-((1S)-1-methoxyethyl)-1,3-thiazol-2-yl)-1-methyl-3-(2-(1-methyl-1H-pyrazol-5-yl)-4-(trifluoromethyl)phenyl)-1H-indole-6-sulfonamide;

1-methyl-3-(4-(methylsulfonyl)phenyl)-N-1,2,4-thiadiazol-5-yl-1H-indole-6-sulfonamide;

N-(3-ethyl-1,2,4-thiadiazol-5-yl)-1-methyl-3-(2-(1-methyl-1H-pyrazol-5-yl)-4-(trifluoromethyl)phenyl)-1H-indole-6-sulfonamide;

1-methyl-3-(4-((methylsulfonyl)amino)phenyl)-N-1,2,4-thiadiazol-5-yl-1H-indole-6-sulfonamide; or 3-(1,3-dimethyl-2,4-dioxo-1,2,3,4-tetrahydro-5-pyrimidinyl)-1-methyl-N-1,2,4-thiadiazol-5-yl-1H-indole-6-sulfonamide.

In embodiment 1a, the present invention provides compounds of Formula I or II, or pharmaceutically acceptable salts thereof,

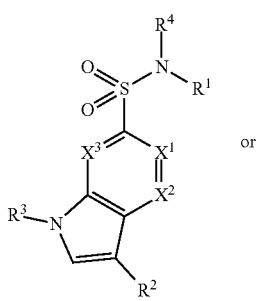

I

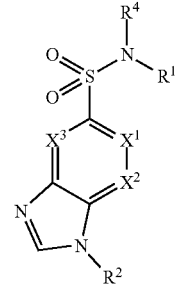

II wherein:
each X$^1$, X$^2$ or X$^3$ is independently CR$^a$ or N;
each R$^a$ is independently hydrogen, halo, C$_{1-6}$alkyl, —OC$_{1-6}$alkyl, or —CN;
each R$^b$ is independently hydrogen or C$_{1-6}$alkyl;
R$^1$ is a five or six membered heteroaryl or heterocycloalkyl group having from one to four heteroatoms independently selected from O, N or S, or a five or six membered aryl or cycloalkyl group, where the heteroaryl, heterocycloalkyl, aryl or cycloalkyl group is unsubstituted or substituted with from one to four substituents selected from halo or C$_{1-6}$alkyl, —OH, —OC$_{1-6}$alkyl or —NR$^b$R$^b$;
R$^2$ is a five to ten membered cycloalkyl, heterocycloalkyl, aryl or heteroaryl group, the heteroaryl or heterocycloalkl group having from one to four heteroatoms independently selected from O, N or S, and where the cycloalkyl, heterocycloalkyl, aryl or heteroaryl group is unsubstituted or substituted with from one to four substituents independently selected from —CF$_3$, —CHF$_2$, —CF$_2$H, —OC$_{1-6}$alkyl, —OCF$_3$, —C$_{1-6}$alkyl, halo, —C≡C—R$^b$, —CN, —NR$^b$R$^b$, —S(=O)$_2$C$_{1-6}$alkyl, or Y;

Y is a five or six membered heteroaryl or heterocycloalkyl group having from one to four heteroatoms independently selected from O, N or S, or a six membered aryl or five or six membered cycloalkyl group, which heteroaryl, heterocycloalkyl, aryl or cycloalkyl group is unsubstituted or substituted with from one to four substituents independently selected from —CF$_3$, —CHF$_2$, —CF$_2$H, —OC$_{1-6}$alkyl, —OCF$_3$, C$_{1-6}$alkyl, halo, —C≡C—R$^b$, —CN, —NR$^b$R$^b$, —S(=O)$_2$C$_{1-6}$alkyl, —C(=O)C$_{1-6}$alkyl or Z;

Z is a three to six membered heterocycloalkyl group having from one to four heteroatoms independently selected from O, N or S;

R$^3$ is hydrogen, C$_{1-6}$alkyl, —C(=O)C$_{1-6}$alkyl, —C(=O)OC$_{1-6}$alkyl, or —S(=O)$_2$ C$_{1-6}$alkyl; and R$^4$ is hydrogen or C$_{1-6}$alkyl, provided that the compound of Formula I is not 1-methyl-3-(2-(1-methyl-1H-pyrazol-5-yl)-4-(trifluoromethyl)phenyl)-N-2-pyrimidinyl-1H-indole-6-sulfonamide;

3-(1-(3-azetidinyl)-1H-pyrazol-3-yl)-1-methyl-N-1,2,4-thiadiazol-5-yl-1H-indole-6-sulfonamide;

3-(2-(5-acetyl-2-thiophenyl)-4-(trifluoromethyl)phenyl)-1-methyl-N-1,2,4-thiadiazol-5-yl-1H-indole-6-sulfonamide;

1-methyl-3-(5-phenyl-2-thiophenyl)-N-1,2,4-thiadiazol-5-yl-1H-indole-6-sulfonamide;

N-(4-((1R)-1-methoxyethyl)-1,3-thiazol-2-yl)-1-methyl-3-(2-(1-methyl-1H-pyrazol-5-yl)-4-(trifluoromethyl)phenyl)-1H-indole-6-sulfonamide, N-(4-((1S)-1-methoxyethyl)-1,3-thiazol-2-yl)-1-methyl-3-(2-(1-methyl-1H-pyrazol-5-yl)-4-(trifluoromethyl)phenyl)-1H-indole-6-sulfonamide;

1-methyl-3-(4-(methylsulfonyl)phenyl)-N-1,2,4-thiadiazol-5-yl-1H-indole-6-sulfonamide;

N-(3-ethyl-1,2,4-thiadiazol-5-yl)-1-methyl-3-(2-(1-methyl-1H-pyrazol-5-yl)-4-(trifluoromethyl)phenyl)-1H-indole-6-sulfonamide;

1-methyl-3-(4-((methylsulfonyl)amino)phenyl)-N-1,2,4-thiadiazol-5-yl-1H-indole-6-sulfonamide; or 3-(1,3-dimethyl-2,4-dioxo-1,2,3,4-tetrahydro-5-pyrimidinyl)-1-methyl-N-1,2,4-thiadiazol-5-yl-1H-indole-6-sulfonamide.

In embodiment 2, the present invention provides compounds in accordance with embodiment 1 or 1a, or pharmaceutically acceptable salts thereof, wherein $R^4$ is hydrogen or methyl.

In embodiment 3, the present invention provides compounds in accordance with embodiment 1 or 1a, or pharmaceutically acceptable salts thereof, wherein $R^4$ is hydrogen.

In embodiment 4, the present invention provides compounds in accordance with embodiment 1 or 1a, or pharmaceutically acceptable salts thereof, wherein $X^1$ is CH; $X^2$ is CH and $X^3$ is CH.

In embodiment 5, the present invention provides compounds in accordance with embodiment 1 or 1a, or pharmaceutically acceptable salts thereof, wherein $R^3$ is methyl or hydrogen.

In embodiment 6, the present invention provides compounds in accordance with embodiment 1 or 1a, or pharmaceutically acceptable salts thereof, wherein $R^3$ is methyl.

In embodiment 7, the present invention provides compounds in accordance with embodiment 1 or 1a, or pharmaceutically acceptable salts thereof, wherein $R^3$ is hydrogen.

In embodiment 8, the present invention provides compounds in accordance with embodiment 1 or 1a, or pharmaceutically acceptable salts thereof, wherein $R^3$ is hydrogen, methyl, —C(=O)CH$_3$, —C(=O)OCH$_3$, or —S(=O)$_2$CH$_3$.

In embodiment 9, the present invention provides compounds in accordance with embodiment for 1a, or pharmaceutically acceptable salts thereof, wherein $R^3$ is $C_{1-6}$alkyl.

In embodiment 10, the present invention provides compounds in accordance with embodiment 1 or 1a, or pharmaceutically acceptable salts thereof, wherein $R^1$ is a five or six membered heteroaryl group having from one to four heteroatoms independently selected from O, N or S.

In embodiment 11, the present invention provides compounds in accordance with embodiment 1 or 1a, or pharmaceutically acceptable salts thereof, wherein $R^1$ is

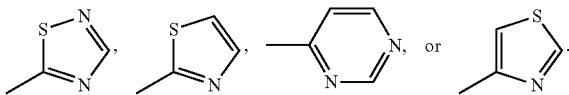

In embodiment 12, the present invention provides compounds in accordance with embodiment 1 or 1a, or pharmaceutically acceptable salts thereof, wherein $R^1$ is

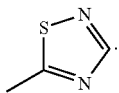

In embodiment 13, the present invention provides compounds in accordance with embodiment 1 or 1a, or pharmaceutically acceptable salts thereof, wherein $R^2$ is a five, six or ten membered aryl or heteroaryl group, the heteroaryl group having from one to four heteroatoms independently selected from O, N or S, and where the aryl or heteroaryl group is unsubstituted or substituted with from one to four substituents independently selected from —CF$_3$, —CHF$_2$, —CF$_2$H, —OC$_{1-6}$alkyl, —OCF$_3$, —C$_{1-6}$alkyl, halo, —C≡C—R$^b$, —CN, —NR$^b$R$^b$, —S(=O)$_2$C$_{1-6}$alkyl, or Y;

Y is a five or six membered heteroaryl or heterocycloalkyl group having from one to four heteroatoms independently selected from O, N or S, or six membered aryl or five or six membered cycloalkyl group, which heteroaryl, heterocycloalkyl, aryl or cycloalkyl group is unsubstituted or substituted with from one to four substituents independently selected from —CF$_3$, —CHF$_2$, —CF$_2$H, —OC$_{1-6}$alkyl, —OCF$_3$, C$_{1-6}$alkyl, halo, —C≡C—R$^b$, —CN, —NR$^b$R$^b$, —S(=O)$_2$C$_{1-6}$alkyl, —C(=O)C$_{1-6}$alkyl or Z; and Z is a three to six membered heterocycloalkyl group having from one to four heteroatoms independently selected from O, N or S.

In embodiment 14, the present invention provides compounds in accordance with embodiment 1 or 1a, or pharmaceutically acceptable salts thereof, wherein $R^2$ is a six membered aryl or heteroaryl group, the heteroaryl group having from one to four heteroatoms independently selected from O, N or S, and where the aryl or heteroaryl group is unsubstituted or substituted with from one to four substituents independently selected from —CF$_3$, —CHF$_2$, —CF$_2$H, —OC$_{1-6}$alkyl, —OCF$_3$, —C$_{1-6}$alkyl, halo, —C≡C—R$^b$, —CN, —NR$^b$R$^b$, —S(=O)$_2$C$_{1-6}$alkyl, or Y;

Y is a five or six membered heteroaryl or heterocycloalkyl group having from one to four heteroatoms independently selected from O, N or S, or six membered aryl or five or six membered cycloalkyl group, which heteroaryl, heterocycloalkyl, aryl or cycloalkyl group is unsubstituted or substituted with from one to four substituents independently selected from —CF$_3$, —CHF$_2$, —CF$_2$H, —OC$_{1-6}$alkyl, —OCF$_3$, C$_{1-6}$alkyl, halo, —C≡C—R$^b$, —CN, —NR$^b$R$^b$, —S(=O)$_2$C$_{1-6}$alkyl, —C(=O)C$_{1-6}$alkyl or Z; and Z is a three to six membered heterocycloalkyl group having from one to four heteroatoms independently selected from O, N or S.

In embodiment 15, the present invention provides compounds in accordance with embodiment 1 or 1a, or pharmaceutically acceptable salts thereof, wherein $R^2$ is a six membered aryl or heteroaryl group the heteroaryl group having from one to four heteroatoms independently selected from O, N or S, and where the aryl or heteroaryl group is unsubstituted or substituted with from one to four substituents independently selected from —CF$_3$, —CHF$_2$, —CF$_2$H, —OC$_{1-6}$alkyl, —OCF$_3$, —C$_{1-6}$alkyl, halo, —C≡C—R$^b$, —CN, —NR$^b$R$^b$, —S(=O)$_2$C$_{1-6}$alkyl, or Y;

Y is

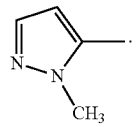

In embodiment 16, the present invention provides compounds in accordance with embodiment 1 or 1a, or pharmaceutically acceptable salts thereof, wherein $R^2$ is phenyl substituted with from one to three substituents independently selected from —CF$_3$, —CHF$_2$, —CF$_2$H, —OC$_{1-6}$alkyl, —OCF$_3$, —C$_{1-6}$alkyl, halo, —C≡C—R$^b$, —CN, —NR$^b$R$^b$, —S(=O)$_2$C$_{1-6}$alkyl, or Y;

Y is a five or six membered heteroaryl group having from one to four heteroatoms independently selected from O, N or S, which heteroaryl group is unsubstituted or substituted with from one to four substituents independently selected from —CF$_3$, —CHF$_2$, —CF$_2$H, —OC$_{1-6}$alkyl, —OCF$_3$, C$_{1-6}$alkyl, halo, —C≡C—R$^b$, —CN, —NR$^b$R$^b$, —S(═O)$_2$C$_{1-6}$alkyl, —C(═O)C$_{1-6}$alkyl or Z; and Z is a three to six membered heterocycloalkyl group having from one to four heteroatoms independently selected from O, N or S.

In embodiment 17, the present invention provides compounds in accordance with embodiment 1 or 1a, or pharmaceutically acceptable salts thereof, wherein R$^2$ is

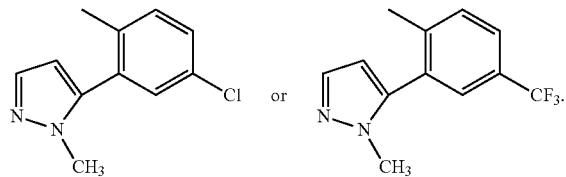 [SMILES: Cc1ccc(Cl)cc1-c1ccnn1C ; Cc1ccc(C(F)(F)F)cc1-c1ccnn1C]

In embodiment 18, the present invention provides the compound, or a pharmaceutically acceptable salt thereof, selected from:

3-(4-chloro-2-(1-methyl-1H-pyrazol-5-yl)phenyl)-N-(2,4-dimethoxybenzyl)-N-(1,2,4-thiadiazol-5-yl)-1H-indole-6-sulfonamide;
3-(4-chloro-2-(1-methyl-1H-pyrazol-5-yl)phenyl)-1-methyl-N-(1,2,4-thiadiazol-5-yl)-1H-indole-6-sulfonamide;
1-isopropyl-3-(2-(1-methyl-1H-pyrazol-5-yl)-4-(trifluoromethyl)phenyl)-N-(1,2,4-thiadiazol-5-yl)-1H-indole-6-sulfonamide;
1-acetyl-3-(2-(1-methyl-1H-pyrazol-5-yl)-4-(trifluoromethyl)phenyl)-N-(1,2,4-thiadiazol-5-yl)-1H-indole-6-sulfonamide;
3-(2-(1-methyl-1H-pyrazol-5-yl)-4-(trifluoromethyl)phenyl)-N-(1,2,4-thiadiazol-5-yl)-1H-indole-6-sulfonamide;
methyl 6-(N-(1,2,4-thiadiazol-5-yl)sulfamoyl)-3-(2-(1-methyl-1H-pyrazol-5-yl)-4-(trifluoromethyl)phenyl)-1H-indole-1-carboxylate;
3-(2-(1-methyl-1h-pyrazol-5-yl)-4-(trifluoromethyl)phenyl)-1-(methylsulfonyl)-N-(1,2,4-thiadiazol-5-yl)-1H-indole-6-sulfonamide;
1-methyl-3-(2-(1-methyl-1H-pyrazol-5-yl)-4-(trifluoromethyl)phenyl)-N-(1,2,4-thiadiazol-5-yl)-1h-indole-6-sulfonamide;
1-methyl-3-(pyridin-3-yl)-N-(1,2,4-thiadiazol-5-yl)-1H-indole-6-sulfonamide;
3-(2,5-difluorophenyl)-1-methyl-N-(1,2,4-thiadiazol-5-yl)-1H-indole-6-sulfonamide;
1-methyl-3-(2-(1-methyl-1H-pyrazol-5-yl)-4-(trifluoromethyl)phenyl)-N-(thiazol-2-yl)-1H-indole-6-sulfonamide;
1-methyl-3-(2-(1-methyl-1H-pyrazol-5-yl)-4-(trifluoromethyl)phenyl)-N-(pyrimidin-4-yl)-1H-indole-6-sulfonamide;
1-methyl-3-(2-(1-methyl-1H-pyrazol-5-yl)-4-(trifluoromethyl)phenyl)-N-(1,3,4-thiadiazol-2-yl)-1H-indole-6-sulfonamide;
1-methyl-3-(5-(prop-1-yn-1-yl)pyridin-3-yl)-N-(1,2,4-thiadiazol-5-yl)-1H-indole-6-sulfonamide;
1-methyl-3-(3-(pyridin-4-yl)-5-(trifluoromethyl)phenyl)-N-(1,2,4-thiadiazol-5-yl)-1H-indole-6-sulfonamide;
3-(2-cyano-4-(trifluoromethyl)phenyl)-1-methyl-n-(1,2,4-thiadiazol-5-yl)-1h-indole-6-sulfonamide;
3-(3-bromo-5-(trifluoromethyl)phenyl)-1-methyl-n-(1,2,4-thiadiazol-5-yl)-1h-indole-6-sulfonamide;
1-methyl-3-(2-(pyridin-4-yl)-4-(trifluoromethyl)phenyl)-N-(1,2,4-thiadiazol-5-yl)-1H-indole-6-sulfonamide;
3-(2-(1-(azetidin-3-yl)-1H-pyrazol-3-yl)-4-(trifluoromethyl)phenyl)-1-methyl-N-(1,2,4-thiadiazol-5-yl)-1H-indole-6-sulfonamide;
1-methyl-3-(2-(1-methyl-1H-pyrazol-5-yl)-4-(trifluoromethyl)phenyl)-N-(5-methyl-4-(trifluoromethyl)thiazol-2-yl)-1H-indole-6-sulfonamide;
3-(2-(1H-pyrazol-4-yl)-4-(trifluoromethyl)phenyl)-1-methyl-N-(1,2,4-thiadiazol-5-yl)-1H-indole-6-sulfonamide;
1-methyl-3-(2-(1,2,3,6-tetrahydropyridin-4-yl)-4-(trifluoromethyl)phenyl)-N-(1,2,4-thiadiazol-5-yl)-1H-indole-6-sulfonamide;
3-(2-chloro-4-(trifluoromethyl)phenyl)-1-methyl-N-(1,2,4-thiadiazol-5-yl)-1H-indole-6-sulfonamide;
3-(3-chloro-4-(trifluoromethyl)phenyl)-1-methyl-N-(1,2,4-thiadiazol-5-yl)-1H-indole-6-sulfonamide;
3-(2-(1-methyl-1H-pyrazol-5-yl)-4-(trifluoromethyl)phenyl)-N-(1,2,4-thiadiazol-5-yl)-1H-pyrrolo[2,3-b]pyridine-6-sulfonamide;
1-methyl-3-(2-(1-methyl-1H-pyrazol-5-yl)-4-(trifluoromethyl)phenyl)-N-(1,2,4-thiadiazol-5-yl)-1H-pyrrolo[2,3-b]pyridine-6-sulfonamide;
1-acetyl-3-(2-(1-methyl 1h-pyrazol-5-yl)-4-(trifluoromethyl)phenyl)-N-(1,2,4-thiadiazol-5-yl)-1H-pyrrolo[2,3-b]pyridine-6-sulfonamide;
3-(4-fluoro-2-methoxyphenyl)-1-methyl-N-(1,2,4-thiadiazol-5-yl)-1H-indole-6-sulfonamide;
3-(3,5-dimethoxyphenyl)-1-methyl-N-(1,2,4-thiadiazol-5-yl)-1H-indole-6-sulfonamide;
3-(3-cyano-4-fluorophenyl)-1-methyl-N-(1,2,4-thiadiazol-5-yl)-1H-indole-6-sulfonamide;
3-(4-cyano-3-fluorophenyl)-1-methyl-N-(1,2,4-thiadiazol-5-yl)-1H-indole-6-sulfonamide;
1-methyl-N-(1,2,4-thiadiazol-5-yl)-3-(4-(trifluoromethoxy)phenyl)-1H-indole-6-sulfonamide;
1-methyl-N-(1,2,4-thiadiazol-5-yl)-3-(3-(trifluoromethoxy)phenyl)-1H-indole-6-sulfonamide;
3-(3-cyanophenyl)-1-methyl-N-(1,2,4-thiadiazol-5-yl)-1H-indole-6-sulfonamide;
1-methyl-3-phenyl-N-(1,2,4-thiadiazol-5-yl)-1H-indole-6-sulfonamide;
3-(2,4-dimethoxyphenyl)-1-methyl-N-(1,2,4-thiadiazol-5-yl)-1H-indole-6-sulfonamide;
1-methyl-3-(naphthalen-1-yl)-N-(1,2,4-thiadiazol-5-yl)-1H-indole-6-sulfonamide;
1-methyl-3-(quinolin-5-yl)-N-(1,2,4-thiadiazol-5-yl)-1H-indole-6-sulfonamide;
1-methyl-3-(3-(methylsulfonyl)phenyl)-N-(1,2,4-thiadiazol-5-yl)-1H-indole-6-sulfonamide;
3-(4-methoxynaphthalen-1-yl)-1-methyl-N-(1,2,4-thiadiazol-5-yl)-1H-indole-6-sulfonamide;
3-(2-chloro-4-methoxyphenyl)-1-methyl-N-(1,2,4-thiadiazol-5-yl)-1H-indole-6-sulfonamide;
3-(3,5-dimethylisoxazol-4-yl)-1-methyl-N-(1,2,4-thiadiazol-5-yl)-1H-indole-6-sulfonamide;
3-(4-bromo-2-(trifluoromethyl)phenyl)-1-methyl-N-(1,2,4-thiadiazol-5-yl)-1H-indole-6-sulfonamide;
1-methyl-N-(1,2,4-thiadiazol-5-yl)-3-(2-(trifluoromethyl)phenyl)-1H-indole-6-sulfonamide;
3-(2-amino-5-methylpyridin-3-yl)-1-methyl-N-(1,2,4-thiadiazol-5-yl)-1H-indole-6-sulfonamide;
3-(4-cyano-2-methylphenyl)-1-methyl-N-(1,2,4-thiadiazol-5-yl)-1H-indole-6-sulfonamide;

3-(3-(dimethylamino)phenyl)-1-methyl-N-(1,2,4-thiadiazol-5-yl)-1H-indole-6-sulfonamide;
1-methyl-N-(1,2,4-thiadiazol-5-yl)-3-(3-(trifluoromethyl)phenyl)-1H-indole-6-sulfonamide;
3-(4-methoxy-3-(trifluoromethyl)phenyl)-1-methyl-N-(1,2,4-thiadiazol-5-yl)-1H-indole-6-sulfonamide;
N-(3-bromo-1,2,4-thiadiazol-5-yl)-1-methyl-3-(2-(1-methyl-1h-pyrazol-5-yl)-4-(trifluoromethyl)phenyl)-1H-indole-6-sulfonamide;
3-(3-chloropyridin-4-yl)-1-methyl-N-(1,2,4-thiadiazol-5-yl)-1H-indole-6-sulfonamide;
1-methyl-3-(1-methyl-1H-pyrazol-5-yl)-n-(1,2,4-thiadiazol-5-yl)-1H-indole-6-sulfonamide;
1-methyl-3-(1,2,3,4-tetrahydroisoquinolin-5-yl)-N-(1,2,4-thiadiazol-5-yl)-1H-indole-6-sulfonamide hydrochloride;
1-methyl-3-(1,2,3,4-tetrahydroisoquinolin-8-yl)-n-(1,2,4-thiadiazol-5-yl)-1H-indole-6-sulfonamide hydrochloride;
3-(1-cyclopropyl-1h-pyrazol-4-yl)-1-methyl-N-(1,2,4-thiadiazol-5-yl)-1H-indole-6-sulfonamide;
3-(5-fluoro-2-methoxypyridin-4-yl)-1-methyl-N-(1,2,4-thiadiazol-5-yl)-1H-indole-6-sulfonamide;
1-methyl-N-(1,2,4-thiadiazol-5-yl)-3-(4-(trifluoromethyl)phenyl)-1H-indole-6-sulfonamide;
1-methyl-N-(1,2,4-thiadiazol-5-yl)-3-(2-(trifluoromethoxy)phenyl)-1H-indole-6-sulfonamide;
3-(benzofuran-2-yl)-1-methyl-N-(1,2,4-thiadiazol-5-yl)-1H-indole-6-sulfonamide;
3-(3-cyano-4-methoxyphenyl)-1-methyl-N-(1,2,4-thiadiazol-5-yl)-1H-indole-6-sulfonamide;
3-(6-methoxypyridin-3-yl)-1-methyl-N-(1,2,4-thiadiazol-5-yl)-1H-indole-6-sulfonamide;
1-(4-chloro-2-(1-methyl-1H-pyrazol-5-yOphenyl)-N-(1,2,4-thiadiazol-5-yl)-1H-benzo[d]imidazole-5-sulfonamide;
1-(2-(1-methyl-1H-pyrazol-5-yl)-4-(trifluoromethyl)phenyl)-N-(1,2,4-thiadiazol-5-yl)-1H-benzo[d]imidazole-5-sulfonamide;
1-methyl-3-(1,2,3,4-tetrahydroisoquinolin-8-yl)-N-(1,2,4-thiadiazol-5-yl)-1H-indole-6-sulfonamide;
1-methyl-3-(2-(1,2,3,6-tetrahydropyridin-4-yl)-4-(trifluoromethyl)phenyl)-N-(thiazol-2-yl)-1H-indole-6-sulfonamide; or
1-methyl-3-(2-(1,2,3,6-tetrahydropyridin-4-yl)-4-(trifluoromethyl)phenyl)-N-(thiazol-4-yl)-1H-indole-6-sulfonamide.

In embodiment 19, the present invention provides methods of treating pain, the method comprising administering to a patient in need thereof a therapeutically effective amount of a compound in accordance with any one of embodiments 1, 1a to 18, or a pharmaceutically acceptable salt thereof.

In embodiment 20, the present invention provide the methods of embodiment 19 wherein the treatment is for chronic pain, acute pain, neuropathic pain, pain associated with rheumatoid arthritis, pain associated with osteoarthritis or pain associated with cancer.

In embodiment 21, the present invention provides pharmaceutical compositions comprising a compound in accordance with any one of embodiments 1, 1a to 18, or pharmaceutically acceptable salts thereof, and a pharmaceutically acceptable excipient.

DETAILED DESCRIPTION OF THE INVENTION

The present invention provides compounds of Formula I or II, as defined above, or pharmaceutically acceptable salts thereof. The present invention also provides pharmaceutical compositions comprising a compound of Formula I or II, or pharmaceutically acceptable salts thereof, and methods of treating diseases and/or conditions, such as pain, using compounds of Formula I or II, or pharmaceutically acceptable salts thereof.

The term "alkyl" means a straight or branched chain hydrocarbon. Representative examples of alkyl groups include methyl, ethyl, propyl, isopropyl, butyl, isobutyl, tert-butyl, sec-butyl, pentyl and hexyl. Typical alkyl groups are alkyl groups having from 1 to 8 carbon atoms, which groups are commonly represented as $C_{1-8}$alkyl.

The term "alkoxy" means an alkyl group bonded to an oxygen atom. Representative examples of alkoxy groups include methoxy, ethoxy, tert-butoxy, propoxy and isobutoxy. Common alkoxy groups are $C_{1-8}$alkoxy.

The term "halogen" or "halo" means chlorine, fluorine, bromine or iodine.

The term "alkenyl" means a branched or straight chain hydrocarbon having one or more carbon-carbon double bonds. Representative examples alkenyl groups include ethenyl, propenyl, allyl, butenyl and 4-methylbutenyl. Common alkenyl groups are $C_{2-8}$alkenyl.

The term "alkynyl" means a branched or straight chain hydrocarbon having one or more carbon-carbon triple bonds. Representative examples of alkynyl groups include ethynyl, propynyl (propargyl) and butynyl. Common alkynyl groups are $C_{2-8}$ alkynyl.

The term "cycloalkyl" means a cyclic, nonaromatic hydrocarbon. Examples of cycloalkyl groups include cyclopropyl, cyclobutyl, cyclopentyl, cyclohexyl and cycloheptyl. A cycloalkyl group can contain one or more double bond. Examples of cycloalkyl groups that contain double bonds include cyclopentenyl, cyclohexenyl, cyclohexadienyl and cyclobutadienyl. Common cycloalkyl groups are $C_{3-8}$ cycloalkyl groups. A cycloalkyl group can also be a bicyclic group comprising a cycloalkyl ring fused to an aryl or heteroaryl ring. An example of such a fused bicyclic group is tetrahydronapthalene.

The term "perfluoroalkyl" means an alkyl group in which all of the hydrogen atoms have been replaced with fluorine atoms. Common perfluoroalkyl groups are $C_{1-8}$perfluoroalkyl. An example of a common perfluoroalkyl group is —$CF_3$.

The term "acyl" means a group derived from an organic acid by removal of the hydroxy group (—OH). For example, the acyl group $CH_3C(=O)$— is formed by the removal of the hydroxy group from $CH_3C(=O)OH$.

The term "aryl" means a cyclic, aromatic hydrocarbon. Examples of aryl groups include phenyl and naphthyl. Common aryl groups are six to thirteen membered rings.

The term "heteroatom" as used herein means an oxygen, nitrogen or sulfur atom.

The term "heteroaryl" means a cyclic, aromatic hydrocarbon in which one or more carbon atoms of an aryl group have been replaced with a heteroatom. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, indolyl, triazolyl, pyridazinyl, indazolyl, purinyl, quinolizinyl, isoquinolyl, quinolyl, naphthyridinyl, quinoxalinyl, isothiazolyl and benzo[b]thienyl. Common heteroaryl groups are five to thirteen membered rings that contain from 1 to 4 heteroatoms. Heteroaryl groups that are five and six membered rings that contain 1 to 3 heterotaoms are particularly common.

The term "heterocycloalkyl" means a cycloalkyl group in which one or more of the carbon atoms has been replaced with a heteroatom. If the heterocycloalkyl group contains more than one heteroatom, the heteroatoms may be the same or different.

Examples of heterocycloalkyl groups include tetrahydrofuryl, morpholinyl, piperazinyl, piperidinyl and pyrrolidinyl. It is also possible for the heterocycloalkyl group to have one or more double bonds, but is not aromatic. Examples of heterocycloalkyl groups containing double bonds include dihydrofuran. Common heterocycloalkyl groups are three to ten membered rings containing from 1 to 4 heteroatoms. Heterocycloalkyl groups that are five and six membered rings that contain 1 to 2 heteroatoms are particularly common. A heterocycloalkyl group can also be a bicyclic group comprising a heterocycloalkyl ring fused to an aryl or heteroaryl ring. Examples of such fused bicyclic ring include tetrahydroquinoline or tetrahydroisoquinoline.

It is also noted that the cyclic ring groups, i.e., aryl, heteroaryl, cycloalkyl, and heterocycloalkyl, can comprise more than one ring. For example, the naphthyl group is a fused bicyclic ring system. It is also intended that the present invention include ring groups that have bridging atoms, or ring groups that have a spiro orientation.

Representative examples of five to six membered aromatic rings, optionally having one or two heteroatoms, are phenyl, furyl, thienyl, pyrrolyl, oxazolyl, thiazolyl, imidazolyl, pyrazolyl, isoxazolyl, isothiazolyl, pyridinyl, pyridiazinyl, pyrimidinyl, and pyrazinyl.

Representative examples of partially saturated, fully saturated or fully unsaturated five to eight membered rings, optionally having one to three heteroatoms, are cyclopentyl, cyclohexyl, cycloheptyl, cyclooctyl and phenyl. Further exemplary five membered rings are furyl, thienyl, pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, isoxazolyl, isothiazolyl, 1,2-dithiolyl, 1,3-dithiolyl, 3H-1,2-oxathiolyl, 1,2,3-oxadizaolyl, 1,2,4-oxadiazolyl, 1,2,5-oxadiazolyl, 1,3,4oxadiazolyl, 1,2,3-triazolyl, 1,2,4-trizaolyl, 1,3,4-thiadiazolyl, 3H-1,2,3-dioxazolyl, 1,2,4-dioxazolyl, 1,3,2-dioxazolyl, 1,3,4-dioxazolyl, 5H-1,2,5-oxathiazolyl, and 1,3-oxathiolyl.

Further exemplary six membered rings are 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyndazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-(3 oxathiazinyl, and 1,4,2-oxadiazinyl.

Further exemplary seven membered rings are azepinyl, oxepinyl, thiepinyl and 1,2,4-triazepinyl.

Further exemplary eight membered rings are cyclooctyl, cyclooctenyl and cyclooctadienyl.

Exemplary bicyclic rings consisting of two fused partially saturated, fully saturated or fully unsaturated five and/or six membered rings, optionally having one to four heteroatoms, are indolizinyl, indolyl, isoindolyl, indolinyl, cyclopenta(b)pyridinyl, pyrano(3,4-b)pyrrolyl, benzofuryl, isobenzofuryl, benzo[b]thienyl, benzo[c]thienyl, 1H-indazolyl, indoxazinyl, benzoxazolyl, anthranilyl, benzimidazolyl, benzthiazolyl, purinyl, quinolinyl, isoquinolinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, pyrido(3,4-b)pyridinyl, pyrido(3,2-b)pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

A cyclic ring group may be bonded to another group in more than one way. If no particular bonding arrangement is specified, then all possible arrangements are intended.

For example, the term "pyridyl" includes 2-, 3-, or 4-pyridyl, and the term "thienyl" includes 2-, or 3-thienyl.

The term "substituted" means that a hydrogen atom on a molecule or group is replaced with a group or atom. Typical substituents include: halogen, $C_{1-8}$alkyl, hydroxyl, $C_{1-8}$alkoxy, —$NR^xR^x$, nitro, cyano, halo or perhalo$C_{1-8}$alkyl, $C_{2-8}$alkenyl, $C_{2-8}$alkynyl, —$SR^x$, —$S(=O)_2R^x$, —$C(=O)OR^x$, —$C(=O)R^x$, wherein each $R^x$ is independently hydrogen or $C_1$-$C_8$ alkyl. It is noted that when the substituent is —$NR^xR^x$, the $R^x$ groups may be joined together with the nitrogen atom to form a ring.

The term "oxo", when used as a substituent, means the =O group, which is typically attached to a carbon atom.

A group or atom that replaces a hydrogen atom is also called a substituent.

Any particular molecule or group can have one or more substituent depending on the number of hydrogen atoms that can be replaced.

The symbol "—" represents a covalent bond and can also be used in a radical group to indicate the point of attachment to another group. In chemical structures, the symbol is commonly used to represent a methyl group in a molecule.

The term "therapeutically effective amount" means an amount of a compound that ameliorates, attenuates or eliminates one or more symptom of a particular disease or condition, or prevents or delays the onset of one of more symptom of a particular disease or condition.

The term "patient" means animals, such as dogs, cats, cows, horses, sheep and humans. Particular patients are mammals. The term patient includes males and females.

The term "pharmaceutically acceptable" means that the referenced substance, such as a compound of the present invention or a formulation containing a compound of the present invention, or a particular excipient, are suitable for administration to a patient.

The terms "treating", "treat" or "treatment" and the like include preventative (e.g., prophylactic) and palliative treatment.

The term "patient in need thereof" means a patient who has or is at risk of having a disease and/or condition that can be treated by inhibition of Nav 1.7, such as chronic pain.

The term "excipient" means any pharmaceutically acceptable additive, carrier, diluent, adjuvant, or other ingredient, other than the active pharmaceutical ingredient (API), which is typically included for formulation and/or administration to a patient.

The compounds of the present invention are administered to a patient in a therapeutically effective amount. The compounds can be administered alone or as part of a pharmaceutically acceptable composition or formulation. In addition, the compounds or compositions can be administered all at once, as for example, by a bolus injection, multiple times, such as by a series of tablets, or delivered substantially uniformly over a period of time, as for example, using transdermal delivery. It is also noted that the dose of the compound can be varied over time.

In addition, the compounds of the present invention can be administered alone, in combination with other compounds of the present invention, or with other pharmaceutically active compounds. The other pharmaceutically active compounds can be intended to treat the same disease or condition as the compounds of the present invention or a different disease or condition. If the patient is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions may be different forms. For example, one or more compound may be delivered via a tablet, while another is administered via injection or orally as a syrup. All combinations, delivery methods and administration sequences are contemplated.

The compounds of the present invention may be used in the manufacture of a medicament for the treatment of a disease and/or condition mediated by Nav 1.7, such as pain.

Pain is typically divided into primary types: chronic and acute pain based on the duration of the pain. Typically, chronic pain lasts for longer than 3 months. Examples of chronic pain include pain associated with rheumatoid arthritis, osteoarthritis, lumbosacral radiculopathy or cancer. Chronic pain also includes idiopathic pain, which is pain that has no identified cause. An example of idiopathic pain is fibromyalgia.

Another type of pain is nociceptive pain. Nociceptive pain is caused by stimulation of peripheral nerve fibers that respond to highly noxious events such as thermal, mechanical or chemical stimuli.

Still another type of pain is neuropathic pain. Neuropathic pain is pain that is caused by damage or disease affecting a part of the nervous system. Phantom limb pain is a type of neuropathic pain. In phantom limb pain, the body detects pain from a part of a body that no longer exists. For example, a person who has had a leg amputated may feel leg pain even though the leg no longer exists.

In one embodiment of the methods of treatment provided by the present invention using the compounds of Formula I or II, or pharmaceutically acceptable salts thereof, the disease is chronic pain. In another aspect, the chronic pain is associated with, but are not limited to, post-herpetic neuralgia (shingles), rheumatoid arthritis, osteoarthritis, diabetic neuropathy, complex regional pain syndrome (CRPS), cancer or chemotherapy-induced pain, chronic back pain, phantom limb pain, trigeminal neuralgia, HIV-induced neuropathy, cluster headache disorders, and migraine, primary erythromelalgia, and paroxysmal extreme pain disorder. Other indications for Nav 1.7 inhibitors include, but are not limited to, depression (Morinville et al., *J Comp Neurol.*, 504:680-689 (2007)), bipolar and other CNS disorders (Ettinger and Argoff, *Neurotherapeutics*, 4:75-83 (2007)), epilepsy: ibid., and Gonzalez, Termin, Wilson, *Methods and Principles in Medicinal Chemistry*, 29:168-192 (2006)), multiple sclerosis (Waxman, *Nature Neurosci.* 7:932-941 (2006)), Parkinson's (Do and Bean, *Neuron* 39:109-120 (2003); Puopolo et al., *J. Neurosci.* 27:645-656 (2007)), restless legs syndrome, ataxia, tremor, muscle weakness, dystonia, tetanus (Hamann M., et. al., *Exp. Neurol.* 184(2):830-838, 2003), anxiety, depression: McKinney B. C, et. al., *Genes Brain Behav.* 7(6):629-638, 2008), learning and memory, cognition (Woodruff-Pak D. S., et. al., *Behav. Neurosci.* 120(2):229-240, 2006), cardiac arrhythmia and fibrillation, contractility, congestive heart failure, sick sinus syndrome (Haufe V., et. al., *J. Mol. Cell. Cardiol.* 42(3): 469-477, 2007), schizophrenia, neuroprotection after stroke, drug and alcohol abuse (Johannessen L. C., *CNS Drugs* 22(1) 27-47, 2008), Alzheimer's (Kim D. Y., et. al., *Nat. Cell. Biol.* 9(7):755-764, 2007), and cancer (Gillet L., et. al., *J Biol Chem* 2009, January 28 (epub)).

Another aspect of the invention relates to a method of treating acute and/or chronic inflammatory and neuropathic pain, dental pain, general headache, migraine, cluster headache, mixed-vascular and non-vascular syndromes, tension headache, general inflammation, arthritis, rheumatic diseases, rheumatoid arthritis, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, comprising the step of administering a compound according to the present invention. A preferred type of pain to be treated is chronic neuropathic pain. Another preferred type of pain to be treated is chronic inflammatory pain.

In another aspect of the invention, the compounds of the present invention can be used in combination with other compounds that are used to treat pain. Examples of such other compounds include, but are not limited to aspirin, celecoxib, hydrocodone, oxycodone, codeine, fentanyl, ibuprofen, ketoprofen, naproxen, acetaminophen, gabapentin and pregabalin. Examples of classes of medicines that contain compounds that can be used in combination with the compounds of the present invention include non-steroidal anti-inflammatory compounds (NSAIDS), steroidal compounds, cycloxogenase inhibitors and opiod analgesics.

The compounds of the present invention may be used in combination with other pharmaceutically active compounds. It is noted that the term "pharmaceutically active compounds" can include biologics, such as proteins, antibodies and peptibodies.

Since one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes and bags. Typically, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing physician or veterinarian.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a compound of the present invention can consist of one tablet or capsule, while a daily dose of the second compound can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of the present invention and other pharmaceutically active compounds, if desired, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. All methods that are used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and non-aqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents.

Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. They may also contain opacifying agents, and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferable suppositories, which can be prepared by mixing the compounds of the present invention with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

Dosage forms for topical administration of a compound of the present invention include ointments, powders, sprays and inhalants. The active compound or fit compounds are admixed under sterile condition with a physiologically acceptable carrier, and any preservatives, buffers, or propellants that may be required. Opthalmic formulations, eye ointments, powders, and solutions are also contemplated as being within the scope of this invention.

The compounds of the present invention can be administered to a patient at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that can be used depends on a number of factors, including the requirements of the patient, the severity of the condition or disease being treated, and the pharmacological activity of the compound being administered. The determination of dosage ranges and optimal dosages for a particular patient is within the ordinary skill in the art.

The compounds of the present invention can be administered as pharmaceutically acceptable salts, esters, amides or prodrugs. The term "salts" refers to inorganic and organic salts of compounds of the present invention. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," J Pharm Sci, 66: 1-19 (1977).

Examples of pharmaceutically acceptable esters of the compounds of the present invention include $C_1$-$C_8$ alkyl esters. Acceptable esters also include $C_5$-$C_7$ cycloalkyl esters, as well as arylalkyl esters such as benzyl. $C_1$-$C_4$ alkyl esters are commonly used. Esters of compounds of the present invention may be prepared according to methods that are well known in the art.

Examples of pharmaceutically acceptable amides of the compounds of the present invention include amides derived from ammonia, primary $C_1$-$C_8$ alkyl amines, and secondary $C_1$-$C_8$ dialkyl amines. In the case of secondary amines, the amine may also be in the form of a 5 or 6 membered heterocycloalkyl group containing at least one nitrogen atom. Amides derived from ammonia, $C_1$-$C_3$ primary alkyl amines and $C_1$-$C_2$ dialkyl secondary amines are commonly used. Amides of the compounds of the present invention may be prepared according to methods well known to those skilled in the art.

The term "prodrug" means compounds that are transformed in vivo to yield a compound of the present invention. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

To illustrate, if the compound of the invention contains a carboxylic acid functional group, a prodrug can comprise an ester formed by the replacement of the hydrogen atom of the acid group with a group such as ($C_1$-$C_8$ alkyl, ($C_2$-$C_{12}$)alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)aminomethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_{2-3}$)alkyl.

Similarly, if a compound of the present invention comprises an alcohol functional group, a prodrug can be formed by the replacement of the hydrogen atom of the alcohol group with a group such as ($C_1$-$C_6$)alkanoyloxymethyl, 1-(($C_1$-$C_6$) alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanoyl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_1$-$C_6$)alkyl)$_2$ or glycosyl (the radical resulting from the removal of a hydroxyl group of the hemiacetal form of a carbohydrate).

In addition, if a compound of the present invention comprises a sulfonamide moiety, a prodrug can be formed by replacement of the sulfonamide N(H) with a group such as —CH$_2$P(O)(O($C_1$-$C_6$)alkyl)$_2$ or —CH$_2$OC(O)($C_1$-$C_6$)alkyl.

The compounds of the present invention also include tautomeric forms of prodrugs.

The compounds of the present invention may contain asymmetric or chiral centers, and therefore, exist in different stereoisomeric forms. It is contemplated that all stereoisomeric forms of the compounds as well as mixtures thereof, including racemic mixtures, form part of the present invention. In addition, the present invention contemplates all geometric and positional isomers. For example, if the compound contains a double bond, both the cis and trans forms (designated as S and E, respectively), as well as mixtures, are contemplated.

Mixture of stereoisomers, such as diastereomeric mixtures, can be separated into their individual stereochemical components on the basis of their physical chemical differences by known methods such as chromatography and/or fractional crystallization. Enantiomers can also be separated by converting the enantiomeric mixture into a diasteromeric mixture by reaction with an appropriate optically active compound (e.g., an alcohol), separating the diastereomers and converting (e.g., hydrolyzing) the individual diastereomers to the corresponding pure enantiomers. Also, some compounds may be atropisomers (e.g., substituted biaryls).

The compounds of the present invention may exist in unsolvated as well as solvated forms with pharmaceutically acceptable solvents such as water (hydrate), ethanol, and the like. The present invention contemplates and encompasses both the solvated and unsolvated forms.

It is also possible that compounds of the present invention may exist in different tautomeric forms. All tautomers of compounds of the present invention are contemplated. For example, all of the tautomeric forms of the tetrazole moiety are included in this invention. Also, for example, all keto-enol or imine-enamine forms of the compounds are included in this invention. Another example of tautomerism is as follows:

Those skilled in the art will recognize that the compound names and structures contained herein may be based on a particular tautomer of a compound. While the name or structure for only a particular tautomer may be used, it is intended that all tautomers are encompassed by the present invention, unless stated otherwise.

It is also intended that the present invention encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{16}O$, $^{17}O$, $^{31}P$, $^{32}P$, $^{35}S$, $^{18}F$, and $^{36}Cl$. In another aspect, the compounds of the present invention contain one or more deuterium atoms (2H) in place of one or more hydrogen atoms.

Compounds of the present invention that contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detection. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of this invention can generally be prepared by substituting a readily available isotopically labelled reagent for a non-isotopically labelled reagent.

The compounds of the present invention may exist in various solid states including crystalline states and as an amorphous state. The different crystalline states, also called polymorphs, and the amorphous states of the present compounds are contemplated as part of this invention.

In synthesizing compounds of the present invention, it may be desirable to use certain leaving groups. The term "leaving groups" ("LG") generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxysuccinimide, N-hydroxybenzotriazole, and the like. Examples of nucleophiles include, but are not limited to, amines, thiols, alcohols, Grignard reagents, anionic species (e.g., alkoxides, amides, carbanions) and the like.

All patents and other publications recited herein are hereby incorporated by reference in their entirety.

The examples presented below illustrate specific embodiments of the present invention. These examples are meant to be representative and are not intended to limit the scope of the claims in any manner It is noted that when a percent (%) is used with regard to a liquid, it is a percent by volume with respect to the solution. When used with a solid, it is the percent with regard to the solid composition. Materials obtained from commercial suppliers were typically used without further purification. Reactions involving air or moisture sensitive reagents were typically performed under a nitrogen or argon atmosphere. Purity was measured using high performance liquid chromatography (HPLC) system with UV detection at 254 nm and 215 nm (System A: Agilent Zorbax Eclipse XDB-C8 4.6×150 mm, 5 micron, 5 to 100% $CH_3CN$ in $H_2O$ with 0.1% TFA for 15 min at 1.5 mL/min; System B: Zorbax SB-C8, 4.6×75 mm, 10 to 90% $CH_3CN$ in $H_2O$ with 0.1% formic acid for 12 min at 1.0 mL/min) (Agilent Technologies, Santa Clara, Calif.). Silica gel chromatography was generally performed with prepacked silica gel cartidges (Biotage, Uppsala, Sweden or Teledyne-Isco, Lincoln, Nebr.). $^{1}H$ NMR spectra were recorded on a Bruker AV-400 (400 MHz) spectrometer (Bruker Corporation, Madison, Wis.) or a Varian (Agilent Technologies, Santa Clara, Calif.) 400 MHz spectrometer at ambient temperature. All observed protons are reported as parts per million (ppm) downfield from tetramethylsilane (TMS) or other internal reference in the appropriate solvent indicated. Data are reported as follows: chemical shift, multiplicity (s=singlet, d=doublet, t=triplet, q=quartet, br=broad, m=multiplet), coupling constants, and number of protons. Low-resolution mass spectral (MS) data were determined on an Agilent 1100 Series (Agilent Technologies, Santa Clara, Calif.) LCMS with UV detection at 254 nm and 215 nm and a low resonance electrospray mode (ESI).

The following abbreviations may be used herein:
AmPhos 4-(di-tert-butylphosphino)-N,N-dimethylaniline
AcCl acetyl chloride
AcOH acetic acid
BOC or Boc tert-butyloxycarbonyl
DCM dichloromethane
DMAP 4-dimethylaminopyridine
DME dimethoxyethane
DMF N,N-dimethylformamide
DMSO dimethyl sulfoxide
Dppf or DPPF 1,1'-bis(diphenylphosphino)ferrocene
ESI or ES electrospray ionization
Et ethyl
$Et_2O$ diethyl ether
$Et_3N$ triethylamine
EtOAc ethyl acetate
g grams
h hour
HPLC high pressure liquid chromatography
iPr isopropyl
$iPr_2NEt$ N-ethyl diisopropylamine (Hunig's base)
KOAc potassium acetate
LC MS, LC-MS or LC/MS liquid chromatography mass spectroscopy
LHMDS or LiHMDS lithium hexamethyldisilazide
m/z mass divided by charge
Me methyl
MeOH methanol
MeCN or ACN acetonitrile
mg milligrams
min minutes
mL milliliters
MS mass spectra NBS N-bromosuccinimide
NCS N-chlorosuccinimide
n-BuLi n-butyllithium
NMR nuclear magnetic resonance
Pd$_2$(dba)$_3$ tris(dibenzylideneacetone)dipalladium(0)
RT or rt room temperature
SFC supercritical fluid chromatography
TBAF tetra-n-butylammonium fluoride
t-BuOH tert-butanol
TIPS-Cl triisopropylsilyl chloride
TFA trifluoroacetic acid
THF tetrahydrofuran
UV ultraviolet
X-Phos 2-dicyclohexylphosphino-2',4',6'-triisopropyl-1,1'-biphenyl

EXAMPLES

General Synthetic Schemes

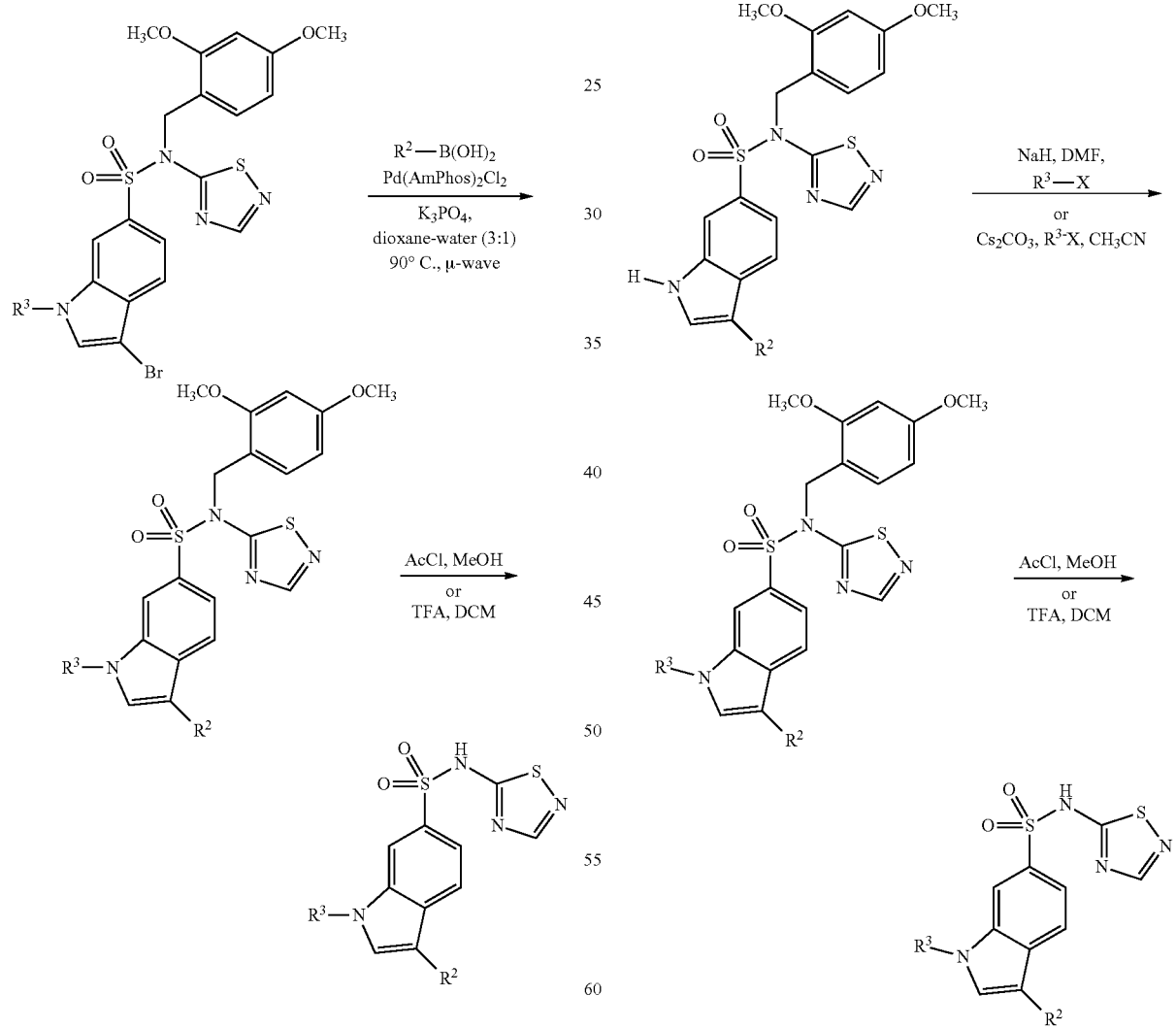

under a number of conditions, including: AcCl in methanol (to generate HCl in situ), neat TFA, a solution of TFA in DCM, and a solution of 4N HCl in 1,4-dioxane.

The Suzuki reaction with the bromoindole can be achieved using a variety of bases (such as Cs$_2$CO$_3$, K$_2$CO$_3$, K$_3$PO$_4$, or Na$_2$CO$_3$), catalysts (such as Pd-(AmPhos)$_2$Cl$_2$, Pd(dppf)Cl$_2$ or Pd(PPh$_3$)$_4$), and solvents (such as aqueous 1,4-dioxane, DME, EtOH, DMF, or t-BuOH). The removal of the dimethoxybenzyl protecting group can be accomplished The Suzuki reaction with the bromoindole can be achieved using a variety of bases (such as Cs$_2$CO$_3$, K$_2$CO$_3$, K$_3$PO$_4$, or Na$_2$CO$_3$), catalysts (such as Pd(AmPhos)$_2$Cl$_2$, Pd(dppf)Cl$_2$ or Pd(PPh$_3$)$_4$), and solvents (such as aqueous 1,4-dioxane, DME, EtOH, DMF, or t-BuOH). Alkylation of the indole nitrogen can be accomplished with a variety of bases (such as NaH or Cs$_2$CO$_3$, or LHMDS), solvents (such as DMF, THF, or acetonitrile), and electrophiles (such as alkyl halides or alkyl halide equivalents, acyl chlorides, sulfonyl chlorides, and carbamoyl chlorides). The removal of the dimethoxybenzyl protecting group can be accomplished under a number of conditions, including: AcCl in methanol (to generate HCl in situ), neat TFA, a solution of TFA in DCM, and a solution of 4N HCl in 1,4-dioxane.

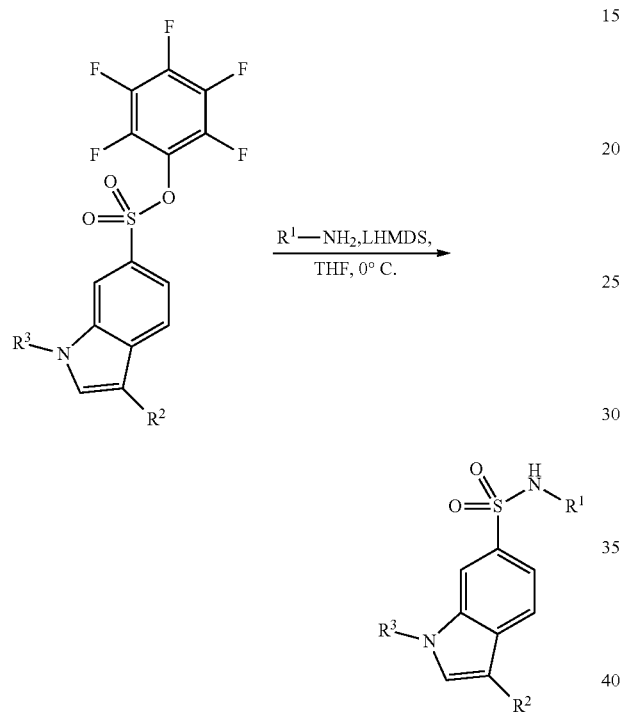

The installation of the aryl sulfonamide can be accomplished with a number of bases (such as LHMDS, LDA, or NaHMDS) in a number of solvents (such as THF or acetonitrile).

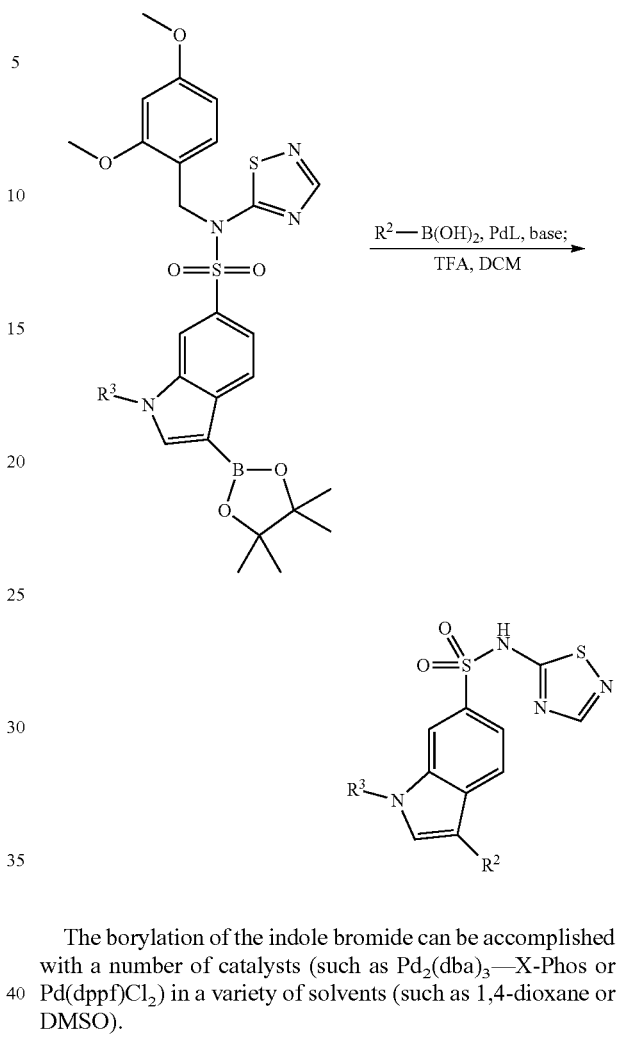

The borylation of the indole bromide can be accomplished with a number of catalysts (such as Pd$_2$(dba)$_3$—X-Phos or Pd(dppf)Cl$_2$) in a variety of solvents (such as 1,4-dioxane or DMSO).

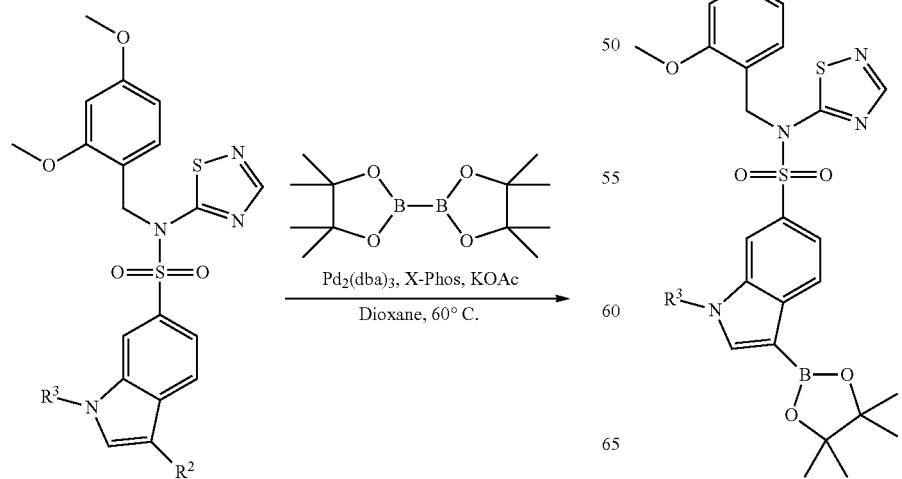

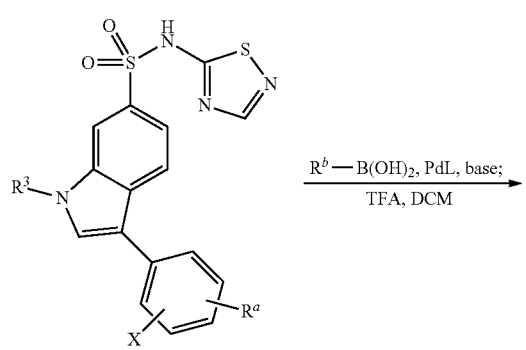

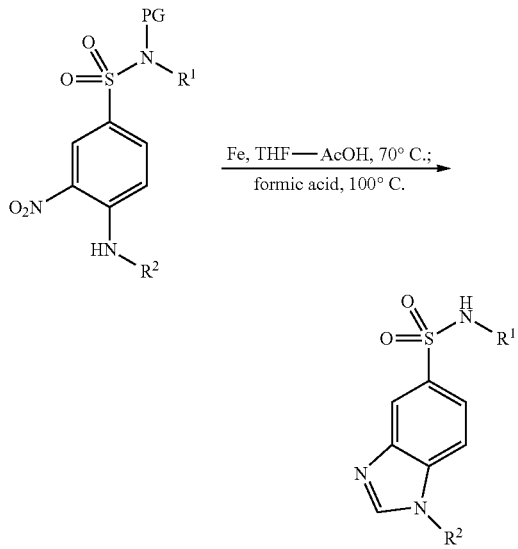

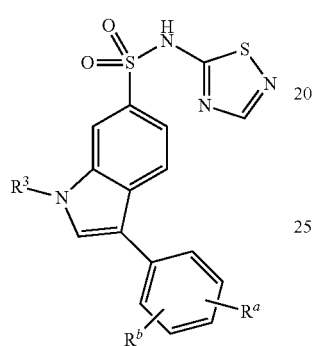

The Suzuki reaction with the aryl boronate can be achieved using a variety of bases (such as $Cs_2CO_3$, $K_2CO_3$, $K_3PO_4$, or $Na_2CO_3$), catalysts (such as $Pd(AmPhos)_2Cl_2$, $Pd(dppf)Cl_2$ or $Pd(PPh_3)_4$), and solvents (such as aqueous 1,4-dioxane, DME, EtOH, DMF, or t-BuOH). The subsequent Suzuki reaction with the remaining aryl halide can be accomplished under similar conditions. The removal of the dimethoxybenzyl protecting group can be accomplished under a number of conditions, including: AcCl in methanol (to generate HCl in situ), neat TFA, a solution of TFA in DCM, and a solution of 4N HCl in 1,4-dioxane.

The sulfonamide formation can be conducted with a variety of bases, depending upon the nature of the amine. For protected amines (PG is a protecting group), strong bases (such as LHMDS, LDA, NaH) are preferred. For unprotected amines, weaker bases (such as potassium carbonate, triethylamine) may be employed. Suitable protecting groups include 2,4-dimethoxybenzyl and 4-methoxybenzyl. The reduction of the nitro group can be accomplished using a number of reductants, such as iron in acidic media, palladium on carbon under an atmosphere of hydrogen, and $SnCl_2$. The benzimidazole formation can be accomplished with either formic acid or a trialkylorthoformate, such as trimethylorthoformate.

Intermediate A: 3-Bromo-N-(2,4-Dimethoxybenzyl)-N-(1,2,4-Thiadiazol-5-yl)-1H-Indole-6-Sulfonamide

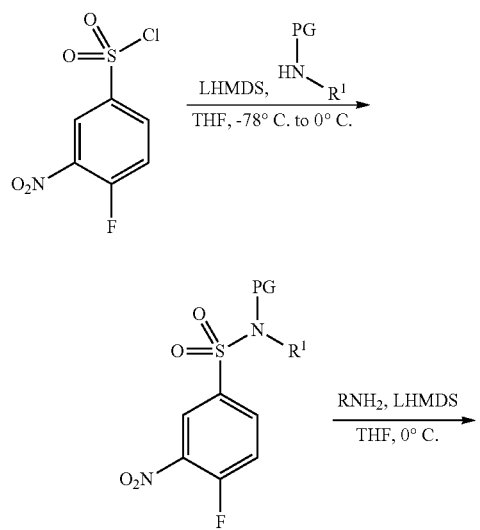

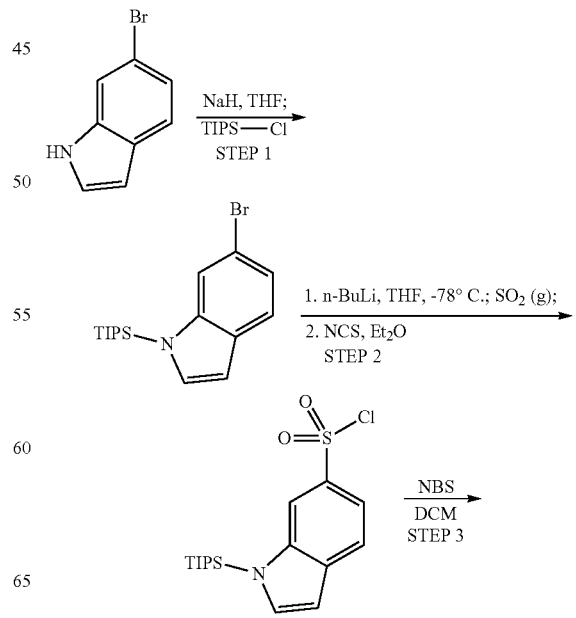

-continued

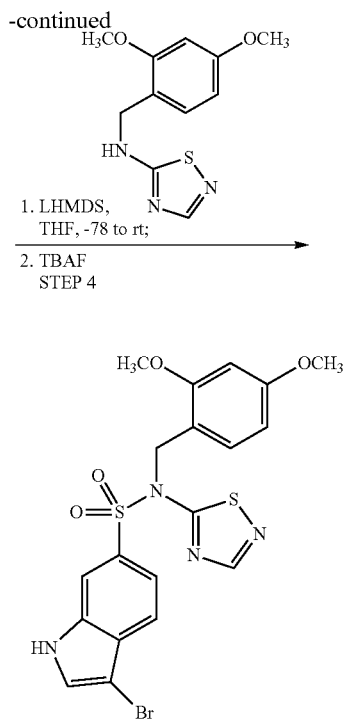

Step 1: 6-Bromo-1-(Triisopropylsilyl)-1H-Indole

A 500 mL 3-neck round-bottom flask was charged with 6-bromo-1H-indole (5.95 g, 30.4 mmol) and THF (60 ml) to give a deep red solution. The flask was fitted with a N₂ sweep, then cooled in an ice bath until an internal temperature of 2 to 5° C. was reached. At this time, sodium hydride (1.457 g, 36.4 mmol) was added portion-wise over 2 to 3 minutes such that the internal temperature was maintained below 10° C. The resulting mixture was stirred at this temperature for 20 minutes before triisopropylsilyl chloride (8.12 ml, 37.9 mmol) was added over 1 min. The cooling bath was removed, and the mixture was stirred for 15 min at room temperature. The volatiles were evaporated in vacuo, and the residue was taken up in saturated aq. sodium bicarbonate solution (150 mL). The mixture was extracted with DCM (2×250 mL), and the combined organic extracts were dried over sodium sulfate, filtered, and concentrated. The crude product was purified by chromatography on silica gel (0 to 10% EtOAc/Heptane) to give 6-bromo-1-(triisopropylsilyl)-1H-indole (7.33 g, 20.80 mmol, 68.5% yield) as a clear oil. ¹H NMR (400 MHz, CDCl₃) δ=8.22 (td, J=0.8, 1.5 Hz, 1 H), 7.85-7.70 (m, 2 H), 7.58 (d, J=3.1 Hz, 1 H), 6.78 (dd, J=1.0, 3.1 Hz, 1 H), 1.84-1.65 (m, 3 H), 1.17 (d, J=7.5 Hz, 18 H).

Step 2: 1-(Triisopropylsilyl)-1H-Indole-6-Sulfonyl Chloride

A 500-mL round-bottom flask was charged 6-bromo-1-(triisopropylsilyl)-1H-indole (4.108 g, 11.66 mmol) and THF (100 mL) to give a clear solution. The flask was cooled in a dry ice and actone bath for 10 min, then n-butyllithium (5.58 ml, 12.82 mmol) was added dropwise over 5 min. The resulting mixture was stirred for 15 min, then sulfur dioxide was added via a syringe. The gas was added for 20 min, then the mixture was warmed to room temperature and concentrated in vacuo. The residue was dissolved in diethyl ether (100 mL), and the resulting solution was cooled in an ice bath. n-Chlorosuccinimide (1.557 g, 11.66 mmol) was added, and the mixture was stirred for 20 min. The solids were removed by filtration of the mixture through Celite® (diatomaceous earth) and washed with diethyl ether (3×). The filtrates were combined, and the combined solution was concentrated in vacuo. The crude product was purified by chromatography on silica gel (0 to 20% EtOAc/Heptane) to give 1-(triisopropylsilyl)-1H-indole-6-sulfonyl chloride (3.028 g, 8.14 mmol, 69.8% yield) as a white solid. ¹H NMR (400 MHz, CDCl₃) δ=8.22 (td, J=0.8, 1.5 Hz, 1 H), 7.85-7.70 (m, 2 H), 7.58 (d, J=3.1 Hz, 1 H), 6.78 (dd, J=1.0, 3.1 Hz, 1 H), 1.84-1.65 (m, 3 H), 1.17 (d, J=7.5 Hz, 18 H).

Step 3: 3-Bromo-1-(Triisopropylsilyl)-1H-Indole-6-Sulfonyl Chloride

A 250-mL round-bottom flask was charged with 1-(triisopropylsilyl)-1H-indole-6-sulfonyl chloride (4.2 g, 11.29 mmol) and DCM (57 ml) to give a clear, maroon solution. n-Bromosuccinimide (2.210 g, 12.42 mmol) was added in one portion, and the resulting mixture was stirred overnight. Silica gel (10.6 g) was added, and the mixture was concentrated. The impregnated silica gel was eluted onto a silica gel column with 0 to 20% EtOAc/Heptane to give to give 3-bromo-1-(triisopropylsilyl)-1H-indole-6-sulfonyl chloride (3.809 g, 8.45 mmol, 74.8% yield) as a light-yellow solid. ¹H NMR (400 MHz, CDCl₃) δ=8.20 (dd, J=0.4, 1.6 Hz, 1 H), 7.89-7.71 (m, 2 H), 7.55 (s, 1 H), 1.72 (quin, J=7.5 Hz, 3 H), 1.18 (d, J=7.7 Hz, 18 H).

Step 4: 3-Bromo-N-(2,4-Dimethoxybenzyl)-N-(1,2,4-Thiadiazol-5-yl)-1H-Indole-6-Sulfonamide A 100-mL flask was charged with N-(2,4-dimethoxybenzyl)-1,2,4-thiadiazol-5-amine (2.160 g, 8.59 mmol) and THF (34 ml) to give a clear, pale-yellow solution. The flask was cooled in a dry ice and acetone bath for 10 min, then lithium bis(trimethylsilyl)amide (1M in THF) (8.59 ml, 8.59 mmol) was added over 30 seconds to give a suspension. The cooling bath was removed for 10 min, which led to the formation of a clear, orange-colored solution. The flask was returned to the dry ice and acetone cooling bath for 5 min to give a cloudy mixture, then a solution of 3-bromo-1-(triisopropylsilyl)-1H-indole-6-sulfonyl chloride (3.1 g, 6.88 mmol) in minimal THF was added dropwise over 1 min to give a clear, brown solution. Following the addition, the cooling bath was removed. When the mixture had reached room temperature, TBAF (8.25 mL of a 1.0 M solution in THF) (8.25 ml, 8.25 mmol) was added, and the reaction was stirred overnight. In the morning, the mixture was diluted with saturated aq. ammonium chloride and water, then extracted with EtOAc (2×). The combined organic extracts were dried over sodium sulfate, filtered, and concentrated. The crude residue was purified by chromatography on silica gel (0 to 50% EtOAc/Heptane). Fractions containing clean product were combined and concentrated to give 1.07 g of product. The remaining impure fractions were combined and concentrated. The residue was further purified by chromatography on silica gel (0 to 10% MeOH/DCM) to give an additional crop of product. The crops of product were combined to afford 3-bromo-N-(2,4-dimethoxybenzyl)-N-(1,2,4-thiadiazol-5-yl)-1H-indole-6-sulfonamide (2.04 g, 4.00 mmol, 58.2% yield). ¹H NMR (400 MHz, DMSO-d₆) δ=12.08 (br. s., 1 H), 8.35 (s, 1 H), 8.01 (dd, J=0.6, 1.7 Hz, 1 H), 7.95 (s, 1 H), 7.66-7.51 (m, 2 H), 6.93 (d, J=8.5 Hz, 1 H), 6.45 (d, J=2.3 Hz, 1 H), 6.36 (dd, J=2.3, 8.5 Hz, 1 H), 5.07 (s, 2 H), 3.73 (s, 3 H), 3.68 (s, 3 H). m/z (ESI) 531.0 (M+Na)$^+$.

Intermediate B: N-(2,4-Dimethoxybenzyl)-3-(2-(1-Methyl-1H-Pyrazol-5-yl)-4-(Trifluoromethyl)Phenyl)-N-(1,2,4-Thiadiazol-5-yl)-1H-Indole-6-Sulfonamide

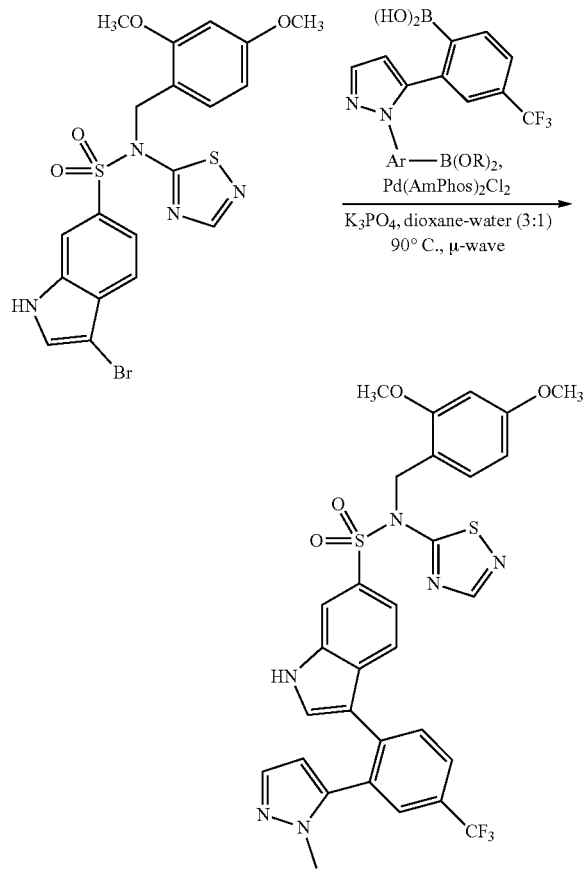

A vial was charged with 3-bromo-N-(2,4-dimethoxybenzyl)-N-(1,2,4-thiadiazol-5-yl)-1H-indole-6-sulfonamide (324 mg, 0.636 mmol), (2-(1-methyl-1H-pyrazol-5-yl)-4-(trifluoromethyl)phenyl)boronic acid (Intermediate G) (223 mg, 0.827 mmol), potassium phosphate (405 mg, 1.908 mmol), and Pd(AmPhos)$_2$Cl$_2$ (22.52 mg, 0.032 mmol), 1,4-dioxane (2.4 mL), and water (0.8 mL). The vial was flushed with Ar, sealed, and heated in a microwave reactor to 90° C. for 40 min. The reaction mixture was diluted with water and extracted with EtOAc (2×). The combined organic extracts were dried over sodium sulfate, filtered, and concentrated. The crude product was purified by chromatography on silica gel (50 to 100% EtOAc/Heptane) to afford N-(2,4-dimethoxybenzyl)-3-(2-(1-methyl-1H-pyrazol-5-yl)-4-(trifluoromethyl)phenyl)-N-(1,2,4-thiadiazol-5-yl)-1H-indole-6-sulfonamide (335.1 mg, 0.512 mmol, 80% yield) as a yellow foam that was about 90% pure as assessed by NMR. $^1$H NMR (400 MHz, DMSO-d$_6$) δ=11.92 (d, J=2.4 Hz, 1 H), 8.34 (s, 1 H), 8.00 (dd, J=0.4, 1.8 Hz, 1 H), 7.95-7.87 (m, 2 H), 7.79-7.76 (m, 1 H), 7.71 (d, J=8.6 Hz, 1 H), 7.49 (dd, J=1.9, 8.6 Hz, 1 H), 7.41 (d, J=1.9 Hz, 1 H), 7.20 (d, J=2.7 Hz, 1 H), 6.92 (d, J=8.4 Hz, 1 H), 6.45 (d, J=2.4 Hz, 1 H), 6.40-6.34 (m, 2H), 5.09 (s, 2 H), 3.72 (s, 3 H), 3.68 (s, 3 H), 3.19 (s, 3 H). m/z (ESI) 655.2 (M+H)$^+$.

Intermediate C:
3-Bromo-1-Methyl-1H-Indole-6-Sulfonyl Chloride

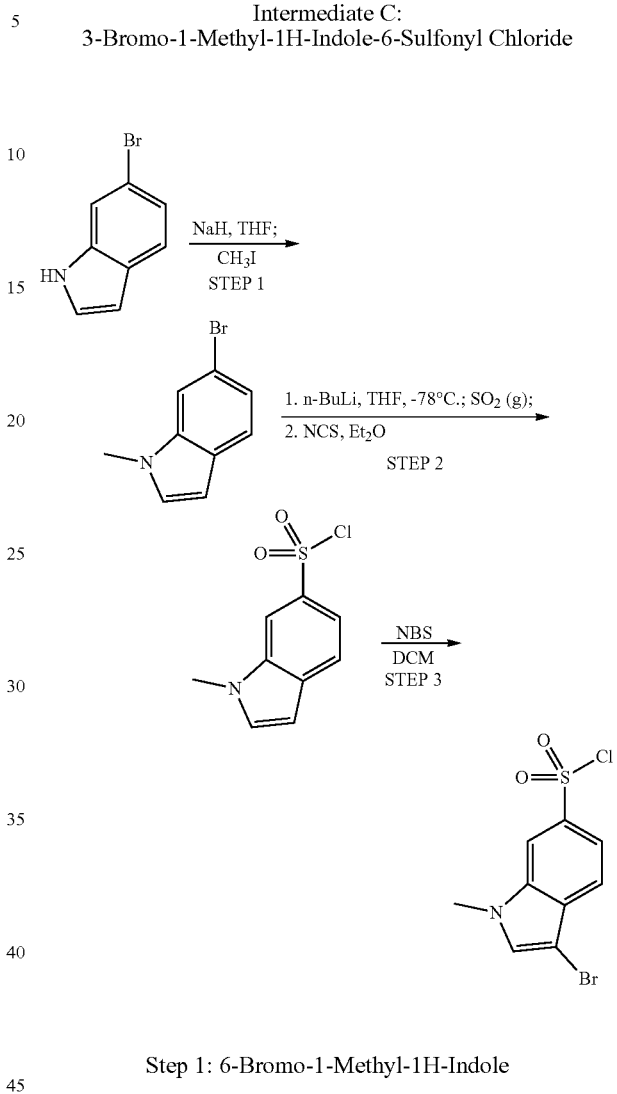

Step 1: 6-Bromo-1-Methyl-1H-Indole

A 1-round-bottom flask was charged with 6-bromo-1H-indole (14.88 g, 76 mmol) and THF (150 ml) to give a dark maroon solution. The flask was put under a N$_2$ sweep, and sodium hydride (60 wt %) (3.64 g, 91 mmol) was added in several portions over 15 min. The resulting mixture was stirred for 20 min, then iodomethane (5.94 ml, 95 mmol) was added via syringe. Within a few minutes, an exotherm was observed. After stirring for 20 min, the mixture was concentrated in vacuo, and the residue was taken up in saturated aq. sodium bicarbonate solution and extracted with DCM (3×). The combined organic extracts were dried over sodium sulfate, filtered, and concentrated. The crude product was purified by chromatography on silica gel (0 to 40% EtOAc/Heptane) to afford 6-bromo-1-methyl-1H-indole (14.44 g, 68.7 mmol, 91% yield) as a lightly colored oil. $^1$H NMR (400 MHz, CDCl$_3$) δ=7.51-7.46 (m, 2 H), 7.24-7.19 (m, 1 H), 7.03 (d, J=3.1 Hz, 1 H), 6.47 (dd, J=0.9, 3.1 Hz, 1 H), 3.77 (s, 3 H).

Step 2: 1-Methyl-1H-Indole-6-Sulfonyl Chloride

A 1-L round-bottom flask was charged 6-bromo-1-methyl-1H-indole (14.44 g, 68.7 mmol). The flask was flushed with Ar, then THF (300 mL) was added to give a clear solution. The flask was cooled in a dry ice and actone bath for 20 min, then n-butyllithium (36.0 ml, 76 mmol) was added dropwise over 10 min to give a white slurry. The mixture was stirred for 20 min, then sulfur dioxide (g) was added to the mixture via a needle for 15 min. The mixture was then warmed to 0° C. and concentrated in vacuo. The residue was suspended in diethyl ether (400 mL). The flask was rotated in a 50° C. oil bath (on the rotary evaporator) for a couple of minutes, leading to a finer solid. The mixture was cooled to 0° C., then n-chlorosuccinimide (9.18 g, 68.7 mmol) was added in one portion. The mixture was stirred for 15 min, then silica gel (20 g) was added, and the mixture was stirred for another 5 min at 0° C. before being filtered through a pad of Celite® (diatomaceous earth). The filter pad was washed twice with diethyl ether, and the filtrates were combined. The combined solution was concentrated, then taken up in diethyl ether. The suspension was placed in a 5° C. refrigerator overnight. In the morning, the mixture was filtered, and the collected solid was washed with ice-cold diethyl ether (3×) then air-dried for 5 min to give about 3.8 g of a yellow solid. The filtrate was concentrated, and the residue was purified by chromatography on silica gel (0 to 40% EtOAc/Heptane). The fractions containing product were combined with the solid described above, dissolved in DCM, and concentrated to give 1-methyl-1H-indole-6-sulfonyl chloride (9.59 g, 41.8 mmol, 60.7% yield) as a yellow solid. $^1$H NMR (400 MHz, CDCl$_3$) δ=8.08 (td, J=0.8, 1.6 Hz, 1 H), 7.82-7.72 (m, 2 H), 7.39 (d, J=3.0 Hz, 1 H), 3.93 (s, 3 H).

Step 3: 3-Bromo-1-Methyl-1H-Indole-6-Sulfonyl Chloride

A solution of 1-methyl-1H-indole-6-sulfonyl chloride (8.764 g, 38.2 mmol) in DCM (190 ml) was treated with n-bromosuccinimide (7.47 g, 42.0 mmol). The resulting mixture was stirred in the dark for 2.5 h, then filtered through a silica gel pad. The filter pad was washed with DCM (2×), and the filtrates were combined. The combined solution was concentrated to give 3-bromo-1-methyl-1H-indole-6-sulfonyl chloride (11.562 g, 37.5 mmol, 98% yield) as an orange solid. $^1$H NMR (400 MHz, CDCl$_3$) δ=8.08 (dd, J=0.4, 1.7 Hz, 1 H), 7.87-7.80 (m, 1 H), 7.79-7.70 (m, 1 H), 7.42 (s, 1 H), 3.93 (s, 3 H).

Intermediate D: 3-Bromo-N-(2,4-Dimethoxybenzyl)-1-Methyl-N-(1,2,4-Thiadiazol-5-yl)-1H-Indole-6-Sulfonamide

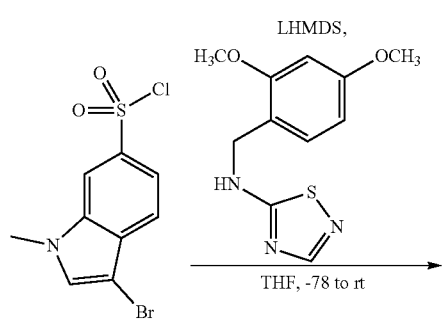

A 1 L round bottom flask was charged with N-(2,4-dimethoxybenzyl)-1,2,4-thiadiazol-5-amine (10.36 g, 41.2 mmol) and THF (190 ml) to give a clear, pale-yellow solution. The flask was cooled to −78° C. in a dry ice and acetone bath, then lithium bis(trimethylsilyl)amide (1M in THF) (43.1 ml, 43.1 mmol) was added dropwise. The cooling bath was removed for 10 min, which led to the formation of a clear, orange-colored solution. The flask was placed back in the cooling bath for 5 min, then a solution of 3-bromo-1-methyl-1H-indole-6-sulfonyl chloride (11.56 g, 37.5 mmol) in minimal THF was added dropwise via cannula. Following the addition, the cooling bath was removed and the reaction was stirred for two hours. The reaction mixture was diluted with a saturated aq. ammonium chloride solution and water, and extracted with EtOAc (2×). The aq. layer was filtered to give some desired product as a pink solid. The filtrate was again extracted with EtOAc, and the organic extracts were combined. The combined solution was dried over sodium sulfate, filtered, and concentrated. The residue was triturated with EtOAc, and the resulting solid was collected via filtration to give a second crop of desired product. The filtrate was absorbed onto silica gel, and the impregnated silica gel was eluted onto a silica gel column (0 to 100% EtOAc/Heptane). The material thus obtained was still impure, so it was further purified by chromatography on silica gel (0 to 10% EtOAc/DCM) to give a third crop of desired product. The three crops were combined to afford 3-bromo-N-(2,4-dimethoxybenzyl)-1-methyl-N-(1,2,4-thiadiazol-5-yl)-1H-indole-6-sulfonamide (16.47 g, 31.5 mmol, 84% yield) as a light pink solid. $^1$H NMR (400 MHz, DMSO-d$_6$) δ=8.34 (s, 1 H), 8.05 (dd, J=0.6, 1.6 Hz, 1 H), 7.95 (s, 1 H), 7.66-7.52 (m, 2 H), 6.95 (d, J=8.4 Hz, 1 H), 6.47-6.26 (m, 2 H), 5.12 (s, 2 H), 3.88 (s, 3 H), 3.69 (s, 3 H), 3.66 (s, 3 H). m/z (ESI) 545.0 (M+H)$^+$.

Intermediate E: Perfluorophenyl 1-Methyl-3-(2-(1-Methyl-1H-Pyrazol-5-yl)-4-(Trifluoromethyl)Phenyl)-1H-Indole-6-Sulfonate -continued

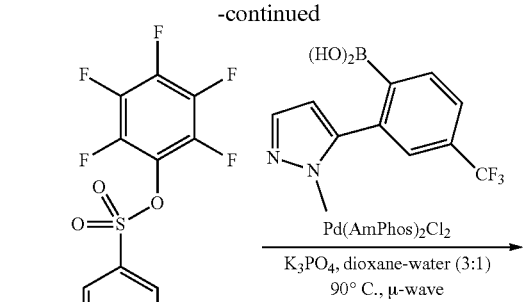

Step 1: Perfluorophenyl 3-Bromo-1-Methyl-1H-Indole-6-Sulfonate

A vial was charged with 3-bromo-1-methyl-1H-indole-6-sulfonyl chloride (505.0 mg, 1.637 mmol), pentafluorophenol (452 mg, 2.455 mmol), and DCM (8.1 mL) to give a clear, light-yellow solution. Triethylamine (342 μl, 2.455 mmol) was added dropwise, and the resulting mixture was stirred for 45 min before being concentrated in vacuo. The crude product was purified by chromatography on silica gel (40% EtOAc/Heptane) to give perfluorophenyl 3-bromo-1-methyl-1H-indole-6-sulfonate (712.3 mg, 1.561 mmol, 95% yield) as an off-white solid. $^1$H NMR (400 MHz, CHLOROFORM-d) δ=8.04 (t, J=1.1 Hz, 1 H), 7.82-7.67 (m, 2 H), 7.41 (s, 1 H), 3.91 (s, 3 H).

Step 2: Perfluorophenyl 1-Methyl-3-(2-(1-Methyl-1H-Pyrazol-5-yl)-4-(Trifluoromethyl)Phenyl)-1H-Indole-6-Sulfonate The following reaction was conducted in two separate vials, and the reaction mixtures were combined before purification: A vial was charged with perfluorophenyl 3-bromo-1-methyl-1H-indole-6-sulfonate (52.1 mg, 0.114 mmol), (2-(1-methyl-1H-pyrazol-5-yl)-4-(trifluoromethyl)phenyl)boronic acid (Intermediate G) (40.1 mg, 0.148 mmol), potassium phosphate (72.7 mg, 0.343 mmol), Pd(AmPhos)$_2$Cl$_2$ (4.04 mg, 5.71 μmol), 1,4-dioxane (428 μl), and water (143 μl). The vial was flushed with Ar, sealed, and heated in a microwave reactor to 90° C. for 30 min. A separate vial was charged with perfluorophenyl 3-bromo-1-methyl-1H-indole-6-sulfonate (180 mg, 0.395 mmol), (2-(1-methyl-1H-pyrazol-5-yl)-4-(trifluoromethyl)phenyl)boronic acid (139 mg, 0.513 mmol), potassium phosphate (251 mg, 1.184 mmol), Pd(AmPhos)$_2$Cl$_2$ (13.97 mg, 0.020 mmol), 1,4-dioxane (1480 μl), and water (493 μl). The vial was flushed with Ar, sealed, and heated in a reactor to 90° C. for 30 min. The reaction mixtures from both vials were combined, and the combined mixture was diluted with water and extracted with EtOAc (2×). The combined organic extracts were dried over sodium sulfate, filtered, and concentrated. The crude product was purified by chromatography on silica gel (10 to 60% EtOAc/Heptane) to give perfluorophenyl 1-methyl-3-(2-(1-methyl-1H-pyrazol-5-yl)-4-(trifluoromethyl)phenyl)-1H-indole-6-sulfonate (250.0 mg, 0.416 mmol, 82% yield) as a pink foam. $^1$H NMR (400 MHz, CDCl$_3$) δ=8.09-8.01 (m, 1 H), 7.91-7.81 (m, 3 H), 7.76-7.67 (m, 2 H), 7.53 (d, J=2.0 Hz, 1 H), 6.79 (s, 1 H), 6.38 (d, J=1.9 Hz, 1 H), 3.81 (s, 3 H), 3.23 (s, 3 H). m/z (ESI) 602.0 (M+H)$^+$.

Intermediate F: (4-Chloro-2-(1-Methyl-1H-Pyrazol-5-yl)Phenyl)Boronic Acid

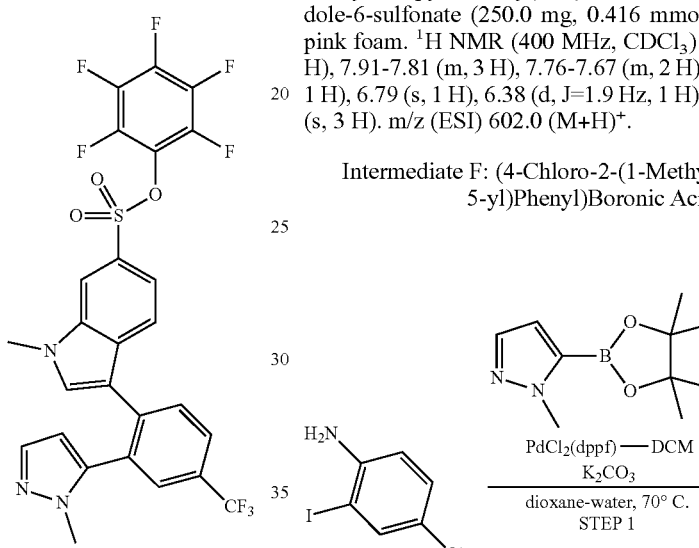

Step 1: 4-Chloro-2-(1-Methyl-1H-Pyrazol-5-yl)Aniline

A 250-mL round-bottom flask was charged with 4-chloro-2-iodoaniline (6.189 g, 24.42 mmol), 1-methyl-5-(4,4,5,5-tetramethyl-1,3,2-dioxaborolan-2-yl)-1H-pyrazole (7.62 g, 36.6 mmol), potassium carbonate (13.50 g, 98 mmol), and PdCl$_2$(dppf)-CH$_2$Cl$_2$ (0.997 g, 1.221 mmol). The flask was flushed with Ar, then 1,4-dioxane (61.0 ml) and water (20.35 ml) were added in sequence. A reflux condenser was attached, and the flask was heated to 70° C. for 4 h. After being cooled to room temperature, the mixture was diluted with water and EtOAc (a small amount of brine was added to clear the emulsion). The layers were separated, and the aq. layer was extracted with EtOAc (2×). The combined organic extracts were dried over sodium sulfate, filtered, and concentrated. The residue was partially purified by chromatography on silica gel (30 to 80% EtOAc/Heptane). The partially purified product was taken up in a boiling mixture of heptane (100-mL) and EtOAc (5 mL) to give an opaque solution. A 250-mL flask containing the solid was charged with heptane (100 mL). The mixture was cooled to room temperature after 3 h, then the solid was collected by filtration, washed with heptane (3×50 mL), and dried under a stream of $N_2$ for 20 min to give 4-chloro-2-(1-methyl-1H-pyrazol-5-yl)aniline (3.732 g, 17.97 mmol, 73.6% yield) as a light purple solid. $^1$H NMR (400 MHz, DMSO-$d_6$) δ=7.50 (d, J=1.9 Hz, 1 H), 7.16 (dd, J=2.6, 8.7 Hz, 1 H), 7.02 (d, J=2.5 Hz, 1 H), 6.78 (d, J=8.7 Hz, 1 H), 6.29 (d, J=1.8 Hz, 1 H), 5.07 (s, 2 H), 3.65 (s, 3 H). m/z (ESI) 208.2 (M+H)$^+$.

Step 2: 5-(2-Bromo-5-Chlorophenyl)-1-Methyl-1H-Pyrazole

A 100-mL flask was charged with copper(ii) bromide (2.472 g, 11.07 mmol) and acetonitrile (45 mL) to give a green suspension. 1,1-Dimethylethyl nitrite (1.462 ml, 11.07 mmol) was added, and the resulting dark green mixture was stirred for 20 min. The flask was cooled in an ice bath for 10 min, then a solution of 4-chloro-2-(1-methyl-1H-pyrazol-5-yl)aniline (1.149 g, 5.53 mmol) in acetonitrile (5 mL with a 2 mL flask/syringe wash) was added dropwise. The resulting mixture was stirred for 72 h at room temperature. The mixture was diluted with water and extracted with EtOAc (3×), and the combined organic extracts were dried over sodium sulfate, filtered, and concentrated. The residue was purified twice by chromatography on silica gel (0 to 100% EtOAc/Heptane) to give 5-(2-bromo-5-chlorophenyl)-1-methyl-1H-pyrazole (0.9923, 3.65 mmol, 66.0% yield) as a brown oil. m/z (ESI) 271.0 (M+H)$^+$.

Step 3: (4-Chloro-2-(1-Methyl-1H-Pyrazol-5-yl) Phenyl)Boronic Acid

A 50-mL round-bottom flask was charged with 5-(2-bromo-5-chlorophenyl)-1-methyl-1H-pyrazole (992.0 mg, 3.65 mmol), diethyl ether (18 mL), and triisopropyl borate (1 mL, 4.38 mmol). The flask was cooled in a dry ice-acetone bath for 10 min, then n-BuLi (1.91 mL, 4.38 mmol) was added dropwise over a couple of minutes. Following the addition, the cooling bath was removed, and the mixture was warmed to room temperature. An aq. 2N NaOH solution (20 mL, 40 mmol) was added, and the resulting mixture was stirred vigorously for 2 h. The mixture was diluted with water and diethyl ether. The layers were separated, and the ethereal layer was extracted with water (2×). The aq. layers were combined, and the combined aq. mixture as washed with diethyl ether. The etheral layer was back-extracted once more, and the aq. layers were all combined. The combined aq. solution was acidified to about pH 1 with 3N aq. HCl to give a clear solution. The aq. solution was extracted with EtOAc (3×), and the combined organic extracts were dried over sodium sulfate, filtered, and concentrated. The residue was taken up in DCM and concentrated in vacuo to give (4-chloro-2-(1-methyl-1H-pyrazol-5-yl)phenyl)boronic acid (660 mg, 2.79 mmol, 76% yield) as a light-yellow foam. m/z (ESI) 237.0 (M+H)$^+$.

Intermediate G: (2-(1-Methyl-1H-Pyrazol-5-yl)-4-(Trifluoromethyl)Phenyl)Boronic Acid

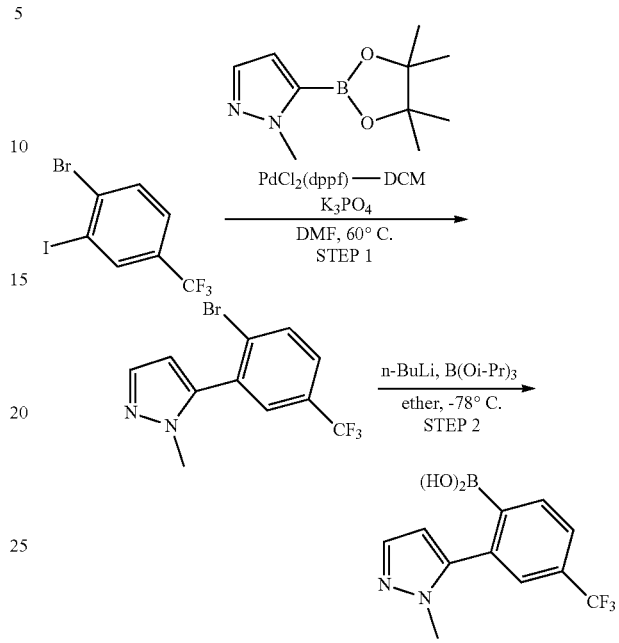

Step 1: 5-(2-Bromo-5-(Trifluoromethyl)Phenyl)-1-Methyl-1H-Pyrazole

A round-bottom flask was charged with 1-bromo-2-iodo-4-(trifluoromethyl)benzene (5.00 g, 14.25 mmol), 1-methyl-1h-pyrazole-5-boronic acid pinacol ester (3.41 g, 16.39 mmol), potassium phosphate (6.05 g, 28.5 mmol) and $PdCl_2$(dppf)-$CH_2Cl_2$ (1.164 g, 1.425 mmol). The flask was flushed with Ar, and DMF (47.5 ml) was then added. The flask was sealed, heated to 60° C. for 12 h, then stirred at room temperature for 48 h. The mixture was diluted with water and extracted with EtOAc (3×). The combined organics were washed with brine, dried, and concentrated in vacuo. The crude product was purified by chromatography on silica gel (0 to 100% EtOAc/Heptane) to yield 5-(2-bromo-5-(trifluoromethyl)phenyl)-1-methyl-1H-pyrazole (2.956 g, 9.69 mmol, 68.0% yield) as a brown solid. $^1$H NMR (400 MHz, DMSO-$d_6$) δ=8.06 (td, J=0.7, 8.1 Hz, 1 H), 7.86-7.73 (m, 2 H), 7.53 (d, J=2.0 Hz, 1 H), 6.41 (d, J=2.0 Hz, 1 H), 3.64 (s, 3 H). m/z (ESI) 305.0 (M+H)$^+$.

Step 2: (2-(1-Methyl-1H-Pyrazol-5-yl)-4-(Trifluoromethyl)Phenyl)Boronic Acid

An 250-mL round-bottom flask was charged with 5-(2-bromo-5-(trifluoromethyl)phenyl)-1-methyl-1H-pyrazole (2.956 g, 9.69 mmol), diethyl ether (74.5 ml), and triisopropyl borate (2.70 ml, 11.63 mmol). The flask was cooled to −78° C. for 10 minutes, after which butyllithium (2.5M in hexanes) (4.65 ml, 11.63 mmol) was added dropwise. The mixture was stirred for 30 min, then warmed to room temperature. A 2N aq. NaOH solution (100 mL), and the resulting biphasic mixture was stirred vigorously for 1 h. The mixture was diluted with water, and the layers separated. The ethereal layer was extracted with water (2×) and the water layers were combined, and washed with diethyl ether. The ether layers were back-extracted once more, and all aqueous layers combined and acidified to about pH 2 with 6N aq HCl to give a clear solution. The aqueous layer was extracted with ethyl acetate (2×), and the combined organics were dried over sodium sulfate, filtered and concentrated. The residue was concentrated from DCM to give (2-(1-methyl-1H-pyrazol-5-yl)-4-(trifluoromethyl)phenyl)boronic acid (2.36 g, 8.74 mmol, 90% yield) as a yellow solid. m/z (ESI) 271.2 (M+H)$^+$.

Intermediate H: N-(2,4-Dimethoxybenzyl)-1-Methyl-3-(4,4,5,5-Tetramethyl-1,3,2-Dioxaborolan-2-yl)-N-(1,2,4-Thiadiazol-5-yl)-1H-Indole-6-Sulfonamide stirred for 15 minutes. The solution was filtered and the solids were washed with ethyl acetate to afford clean N-(2,4-dimethoxybenzyl)-1-methyl-3-(4,4,5,5-tetramethyl-1,3,2-dioxaborolan-2-yl)-N-(1,2,4-thiadiazol-5-yl)-1H-indole-6-sulfonamide. The filtrate was concentrated and purified via column chromatography (RediSep Gold (Teledyne Isco, Lincoln, Nebr.) 80 g, gradient elution 0 to 5% EtOAc:DCM) and the clean fractions were combined with the previously isolated material to afford N-(2,4-dimethoxybenzyl)-1-methyl-3-(4,4,5,5-tetramethyl-1,3,2-dioxaborolan-2-yl)-N-(1,2,4-thiadiazol-5-yl)-1H-indole-6-sulfonamide as a light yellow solid.

Intermediate I: 3-(2-Bromo-4-(Trifluoromethyl)Phenyl)-N-(2,4-Dimethoxybenzyl)-1-Methyl-N-(1,2,4-Thiadiazol-5-yl)-1H-Indole-6-Sulfonamide

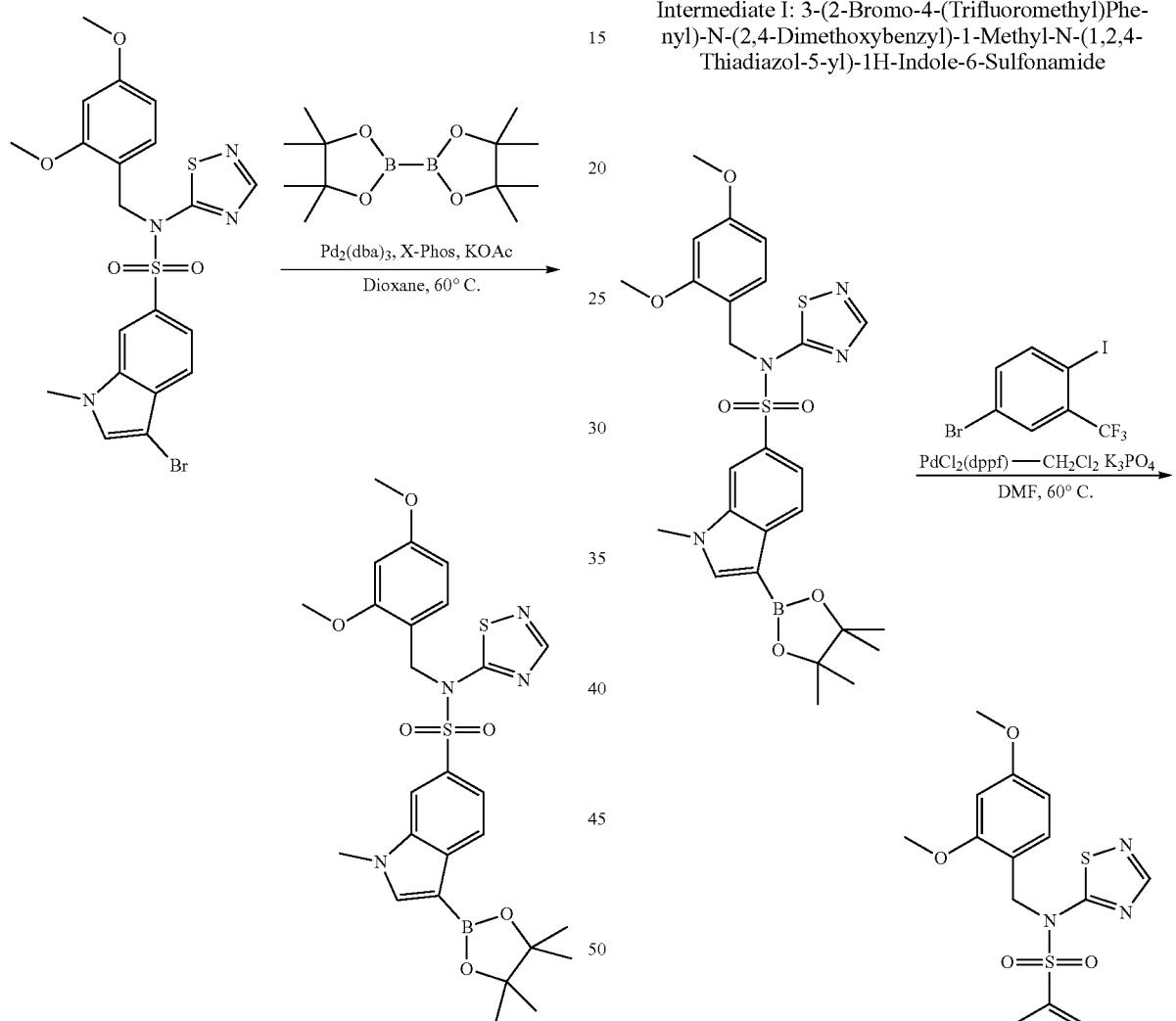

A 150 mL heavy-walled pressure flask with a threaded screw cap was charged with 3-bromo-N-(2,4-dimethoxybenzyl)-1-methyl-N-(1,2,4-thiadiazol-5-yl)-1H-indole-6-sulfonamide (4.00 g, 7.64 mmol), bis(pinacolato)diboron (5.82 g, 22.93 mmol), potassium acetate (3.00 g, 30.6 mmol), Pd$_2$(dba)$_3$ (0.700 g, 0.764 mmol), and X-Phos (0.729 g, 1.528 mmol). 1,4-Dioxane (50.9 ml) was added, the flask was flushed with Ar and sealed, and the reaction was heated to 60° C. and stirred for 18 hours. The reaction was diluted with ethyl acetate and washed with water. The aqueous layer was extracted with ethyl acetate, and the combined organic layers were dried over sodium sulfate, filtered, and concentrated. The isolated solid material was triturated in ethyl acetate and A vial was charged with N-(2,4-dimethoxybenzyl)-1-methyl-3-(4,4,5,5-tetramethyl-1,3,2-dioxaborolan-2-yl)-N-(1,2,4-thiadiazol-5-yl)-1H-indole-6-sulfonamide (0.500 g, 0.876 mmol), 2-bromo-1-iodo-4-(trifluoromethyl)benzene (0.769 g, 2.191 mmol), potassium phosphate (0.651 g, 3.07 mmol), and PdCl$_2$(dppf)-CH$_2$Cl$_2$ (0.072 g, 0.088 mmol). DMF (5.84 ml), and the vial was flushed with argon, sealed, and stirred at 60° C. for two hours. The reaction was diluted with ethyl acetate and washed with water. The aqueous layer was extracted with ethyl acetate, and the combined organic layers were washed with brine, dried with sodium sulfate, filtered, and concentrated. The material was purified via column chromatography (silica gel, gradient elution 0 to 100% EtOAc:Hexanes) to afford 3-(2-bromo-4-(trifluoromethyl)phenyl)-N-(2,4-dimethoxybenzyl)-1-methyl-N-(1,2,4-thiadiazol-5-yl)-1H-indole-6-sulfonamide (0.255 g, 0.382 mmol, 43.6% yield) as an off-white solid. m/z (ESI) 667.0 (M+H)$^+$.

Intermediate J: N-(2,4-Dimethoxybenzyl)-3-(2-(1-Methyl-1H-Pyrazol-5-yl)-4-(Trifluoromethyl)Phenyl)-N-(1,2,4-Thiadiazol-5-yl)-1H-Indole-6-Sulfonamide

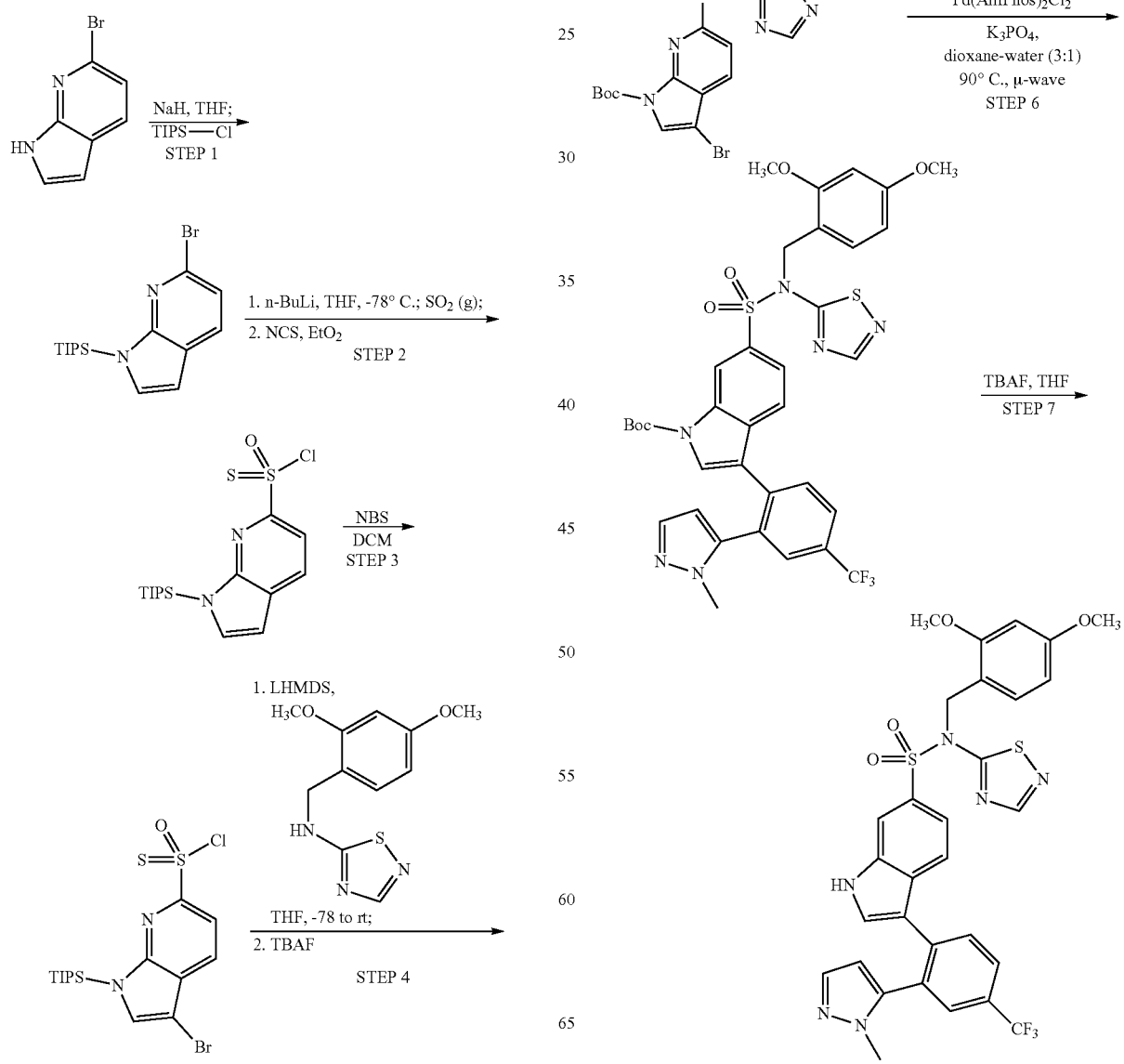

Step 1: 6-Bromo-1-(Triisopropylsilyl)-1H-Pyrrolo[2,3-B]Pyridine

A 200-mL round-bottom flask was charged with 6-bromo-1H-pyrrolo[2,3-b]pyridine (2.961 g, 15.03 mmol) and THF (30 ml) to give a yellow solution. The flask was fitted with an $N_2$ sweep, then sodium hydride (60% disperion in mineral oil) (0.721 g, 18.03 mmol) was added over 2 min, and the resulting mixture was stirred for 40 min. Triisopropylsilyl chloride (4.02 ml, 18.79 mmol) was added in one portion, and the mixture was stirred for 30 min before being concentrated in vacuo. The residue was taken up in saturated aq. sodium bicarbonate solution and extracted with DCM (3×). The combined organic extracts were dried over sodium sulfate, filtered, and concentrated. The crude product was purified by chromatography on silica gel (0 to 10% EtOAc/Heptane) to give 6-bromo-1-(triisopropylsilyl)-1H-pyrrolo[2,3-b]pyridine (2.952 g, 8.35 mmol, 55.6% yield) as a white solid. $^1$H NMR (400 MHz, CDCl$_3$) δ=7.72 (d, J=8.1 Hz, 1 H), 7.26 (d, J=3.5 Hz, 1 H), 7.18 (d, J=8.1 Hz, 1 H), 6.53 (d, J=3.5 Hz, 1 H), 1.81 (spt, J=7.5 Hz, 3 H), 1.13 (d, J=7.5 Hz, 18 H).

Step 2: 1-(Triisopropylsilyl)-1H-Pyrrolo[2,3-B]Pyridine-6-Sulfonyl Chloride

A 250-mL round-bottom flask was charged 6-bromo-1-(triisopropylsilyl)-1H-pyrrolo[2,3-b]pyridine (2.95 g, 8.35 mmol) and THF (80 ml) to give a clear solution. The flask was cooled in a dry ice and acetone bath for 20 min, then n-butyllithium (3.99 ml, 9.18 mmol) was added dropwise over 5 min. The resulting mixture was stirred for 20 min, then sulfur dioxide was added through a needle over 15 min. Following the addition, the mixture was warmed to room temperature, then concentrated in vacuo. The residue was taken up in diethyl ether (80 mL) to give an opaque mixture. The mixture was cooled in an ice bath for 10 min, then n-chlorosuccinimide (1.115 g, 8.35 mmol) was added in one portion at 11:15 am. The mixture was stirred for 20 min, stirred with Celite® (diatomaceous earth) for 10 min, then filtered through Celite® (diatomaceous earth) with the aid of diethyl ether. The filtrate was concentrated, and the crude product was purified by chromatography on silica gel (0 to 20% EtOAc/Heptane) to give 1-(triisopropylsilyl)-1H-pyrrolo[2,3-b]pyridine-6-sulfonyl chloride (2.113 g, 5.67 mmol, 67.9% yield) as a white, crystalline solid. $^1$H NMR (400 MHz, CDCl$_3$) δ=8.10 (d, J=8.2 Hz, 1 H), 7.87 (d, J=8.2 Hz, 1 H), 7.66 (d, J=3.5 Hz, 1 H), 6.76 (d, J=3.5 Hz, 1 H), 1.90 (quin, J=7.6 Hz, 3 H), 1.15 (d, J=7.5 Hz, 18 H).

Step 3: 3-Bromo-1-(Triisopropylsilyl)-1H-Pyrrolo[2,3-B]Pyridine-6-Sulfonyl Chloride A 100-mL recovery flask was charged with 1-(triisopropylsilyl)-1H-pyrrolo[2,3-b]pyridine-6-sulfonyl chloride (2.11 g, 5.66 mmol) and DCM (28 ml) to give a clear solution. n-Bromosuccinimide (1.108 g, 6.22 mmol) was added in one portion. The resulting mixture was stirred in the dark for 4 h, then an additional portion of n-bromosuccinimide (1.108 g, 6.22 mmol) was added. The mixture was stirred overnight. In the morning, silica gel was added, and the mixture was concentrated. The impregnated silica gel was loaded onto a column, and the column was eluted onto a silica gel column with 0 to 15% EtOAc/Heptane to give 3-bromo-1-(triisopropylsilyl)-1H-pyrrolo[2,3-b]pyridine-6-sulfonyl chloride (2.14 g, 4.74 mmol, 84% yield) as a light-yellow solid. $^1$H NMR (400 MHz, CDCl$_3$) δ=8.08 (d, J=8.3 Hz, 1 H), 7.95 (d, J=8.3 Hz, 1 H), 7.63 (s, 1 H), 1.88 (spt, J=7.5 Hz, 4 H), 1.15 (d, J=7.5 Hz, 18 H).

Step 4: 3-Bromo-N-(2,4-Dimethoxybenzyl)-N-(1,2,4-Thiadiazol-5-yl)-1H-Pyrrolo[2,3-B]Pyridine-6-Sulfonamide A 50-mL round-bottom flask was charged with N-(2,4-dimethoxybenzyl)-1,2,4-thiadiazol-5-amine (0.962 g, 3.83 mmol) and THF (17 mL) to give a clear, light-yellow solution. The flask was cooled in a dry ice-acetone bath for 5 min, then lithium bis(trimethylsilyl)amide (1M in THF) (3.83 ml, 3.83 mmol) was added dropwise.

Following the addition, the flask was removed from the bath for 10 min, then re-cooled in the bath for 10 min. A solution of 3-bromo-1-(triisopropylsilyl)-1H-pyrrolo[2,3-b]pyridine-6-sulfonyl chloride (1.573 g, 3.48 mmol) in THF (3 mL with a 1 mL syringe/vial wash) was added dropwise at over 2 min. The mixture was warmed to room temperature, then tetra-n-butylammonium fluoride (1M in THF) (3.66 ml, 3.66 mmol) was added. After stirring for an additional 2 h, the mixture was diluted with saturated aq. ammonium chloride and EtOAc. The organic layer was washed with water, then dried over sodium sulfate. The mixture was concentrated in vacuo, then was concentrated again from EtOAc. The residue was then taken up in EtOAc filtered. The collected solid was washed with EtOAc (2×), then dried under a stream of $N_2$ to give 3-bromo-N-(2,4-dimethoxybenzyl)-N-(1,2,4-thiadiazol-5-yl)-1H-pyrrolo[2,3-b]pyridine-6-sulfonamide (1.2452 g, 2.440 mmol, 70.1% yield) as a light-pink solid. $^1$H NMR (400 MHz, DMSO-d$_6$) δ=12.79 (br. s., 1 H), 8.36 (s, 1 H), 8.12-8.07 (m, 2 H), 7.80 (d, J=8.2 Hz, 1 H), 6.96 (d, J=8.4 Hz, 1 H), 6.40 (s, 1 H), 6.34 (dd, J=2.4, 8.5 Hz, 1 H), 5.17 (s, 2 H), 3.69 (s, 3 H), 3.68 (s, 3 H).

Step 5: Tert-Butyl 3-Bromo-6-(N-(2,4-Dimethoxybenzyl)-N-(1,2,4-Thiadiazol-5-yl)Sulfamoyl)-1H-Pyrrolo[2,3-B]Pyridine-1-Carboxylate A 15-mL round-bottom flask was charged with 3-bromo-N-(2,4-dimethoxybenzyl)-N-(1,2,4-thiadiazol-5-yl)-1H-pyrrolo[2,3-b]pyridine-6-sulfonamide (1.0424 g, 2.042 mmol), cesium fluoride (0.031 g, 0.204 mmol), and DMF (8 mL) to give a thick slurry. Di-tert-butyl dicarbonate (0.490 g, 2.247 mmol) was added, followed by an additional portion of cesium fluoride (0.031 g, 0.204 mmol). The resulting thick slurry was stirred for 3 h, at which time the solids had dissolved. The mixture was partitioned between water and EtOAc, with a small amount of brine to breakup an emulsion. The layers were separated, and the aq. layer was extracted with EtOAc. The organic extracts were combined, washed with brine, dried over sodium sulfate, filtered, and concentrated. The crude product was purified by chromatography on silica gel (0 to 50% EtOAc/Heptane) to give tert-butyl 3-bromo-6-(N-(2,4-dimethoxybenzyl)-N-(1,2,4-thiadiazol-5-yl)sulfamoyl)-1H-pyrrolo[2,3-b]pyridine-1-carboxylate (1.112 g, 1.821 mmol, 89% yield) as a white foam. $^1$H NMR (400 MHz, DMSO-d$_6$) δ=8.36 (d, J=7.9 Hz, 2 H), 8.19 (d, J=8.2 Hz, 1 H), 8.04 (d, J=8.2 Hz, 1 H), 6.99 (d, J=8.4 Hz, 1 H), 6.38 (d, J=2.3 Hz, 1 H), 6.33 (dd, J=2.4, 8.5 Hz, 1 H), 5.27 (s, 2 H), 3.69 (s, 3 H), 3.67 (s, 3 H), 1.57 (s, 9 H). m/z (ESI) 610.0 (M+H)$^+$.

Step 6: Tert-Butyl 6-(N-(2,4-Dimethoxybenzyl)-N-(1,2,4-Thiadiazol-5-yl)Sulfamoyl)-3-(2-(1-Methyl-1H-Pyrazol-5-yl)-4-(Trifluoromethyl)Phenyl)-1H-Pyrrolo[2,3-B]Pyridine-1-Carboxylate A vial was charged with tert-butyl 3-bromo-6-(N-(2,4-dimethoxybenzyl)-N-(1,2,4-thiadiazol-5-yl)sulfamoyl)-1H- pyrrolo[2,3-b]pyridine-1-carboxylate (531.8 mg, 0.871 mmol), (2-(1-methyl-1H-pyrazol-5-yl)-4-(trifluoromethyl)phenyl)boronic acid (306 mg, 1.132 mmol), potassium phosphate (555 mg, 2.61 mmol), and Pd(AmPhos)$_2$Cl$_2$ (30.8 mg, 0.044 mmol). 1,4-Dioxane (2178 µl) and water (726 µl) were added in sequence. The vial was sealed and heated in a microwave reactor for 30 min at 90° C. The organic layer was removed via pipette, and the aq. layer was extracted with EtOAc (2×). The combined organic extracts were concentrated in vacuo. The crude product was purified by chromatography on silica gel (0 to 50% EtOAc/Heptane) to give tert-butyl 6-(N-(2,4-dimethoxybenzyl)-N-(1,2,4-thiadiazol-5-yl)sulfamoyl)-3-(2-(1-methyl-1H-pyrazol-5-yl)-4-(trifluoromethyl)phenyl)-1H-pyrrolo[2,3-b]pyridine-1-carboxylate (469 mg, 0.621 mmol, 71.2% yield) as a white solid. m/z (ESI) 756.2 (M+H)$^+$.

Step 7: N-(2,4-Dimethoxybenzyl)-3-(2-(1-Methyl-1H-Pyrazol-5-yl)-4-(Trifluoromethyl)Phenyl)-N-(1,2,4-Thiadiazol-5-yl)-1H-Pyrrolo[2,3-B]Pyridine-6-Sulfonamide A 50-mL round-bottom flask was charged with tert-butyl 6-(N-(2,4-dimethoxybenzyl)-N-(1,2,4-thiadiazol-5-yl)sulfamoyl)-3-(2-(1-methyl-1H-pyrazol-5-yl)-4-(trifluoromethyl)phenyl)-1H-pyrrolo[2,3-b]pyridine-1-carboxylate (469 mg, 0.621 mmol) and THF (4 mL) to give a clear solution. Tetra-n-butylammonium fluoride (1M in THF) (3103 µl, 3.10 mmol) was added in one portion. The mixture was stirred for 3 h, then diluted with EtOAc. The organic solution was washed with a saturated aq. ammonium chloride solution, washed with water (2×), washed with brine, dried over sodium sulfate, filtered, and concentrated. The crude product was purified by chromatography on silica gel (10 to 60% EtOAc/Heptane) to give N-(2,4-dimethoxybenzyl)-3-(2-(1-methyl-1H-pyrazol-5-yl)-4-(trifluoromethyl)phenyl)-N-(1,2,4-thiadiazol-5-yl)-1H-pyrrolo[2,3-b]pyridine-6-sulfonamide (363.86 mg, 0.555 mmol, 89% yield) as an off-white foam. $^1$H NMR (400 MHz, DMSO-d$_6$) δ=12.68 (s, 1 H), 8.36 (s, 1 H), 8.09 (s, 1 H), 7.98-7.87 (m, 2 H), 7.83-7.79 (m, 1 H), 7.73 (d, J=8.3 Hz, 1 H), 7.43-7.36 (m, 2 H), 6.98 (s, 1 H), 6.46-6.31 (m, 3 H), 5.18 (s, 2 H), 3.70 (s, 3 H), 3.69 (s, 3 H), 3.26 (s, 3 H). m/z (ESI) 656.2 (M+H)$^+$.

Intermediate K: 3-Bromo-N-(4-Methoxybenzyl)-1,2,4-Thiadiazol-5-Amine

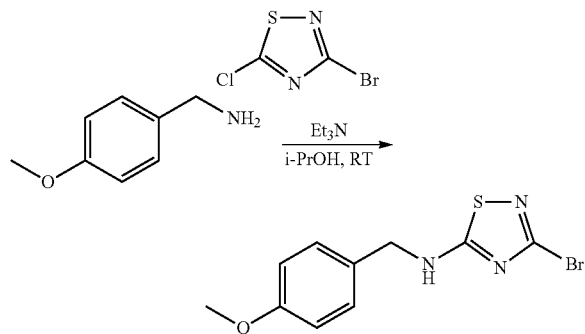

A round-bottom flask was charged with 3-bromo-5-chloro-1,2,4-thiadiazole (2.73 g, 13.69 mmol), i-PrOH (25 mL), and triethylamine (3.82 ml, 27.4 mmol) to give a clear solution. 4-Methoxybenzylamine (2.132 ml, 16.42 mmol) was added dropwise at room temperature, and the resulting mixture was stirred for 2 h before being diluted with EtOAc. The organic solution was washed with saturated aq. sodium bicarbonate solution, washed with water, washed with brine, dried over sodium sulfate, filtered, and concentrated. The crude product was purified by chromatography on silica gel (0 to 40% EtoAc/Heptane) to give a white solid. The solid was suspended in heptane, and the slurry was filtered. The collected solid was washed with heptane (3×), then dried under a stream of N$_2$ overnight to give 3-bromo-N-(4-methoxybenzyl)-1,2,4-thiadiazol-5-amine (2.774 g, 9.24 mmol, 67.5% yield) as a white, fluffy solid. $^1$H NMR (400 MHz, DMSO-d$_6$) δ=9.20 (br. s., 1 H), 7.33-7.20 (m, 2 H), 7.01-6.84 (m, 2 H), 4.43 (br. s., 2 H), 3.74 (s, 3 H). m/z (ESI) 300.0 (M+H)$^+$.

Intermediate L: 2-(1-Methyl-1H-Pyrazol-5-yl)-4-(Trifluoromethyl)Aniline

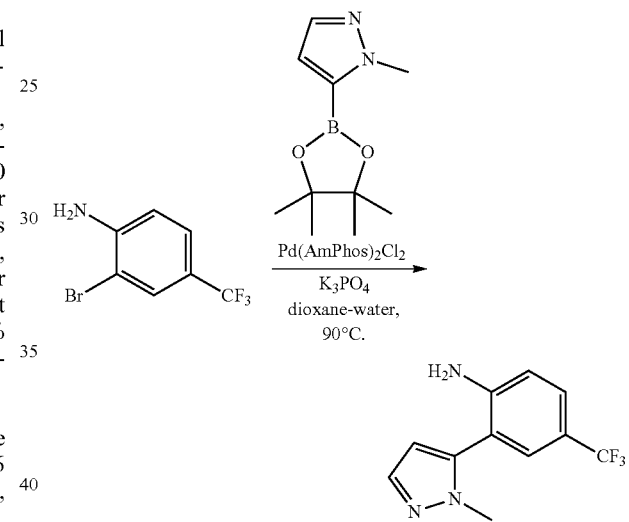

A round-bottom flask was charged with 2-bromo-4-(trifluoromethyl)aniline (4.115 g, 17.14 mmol), 1-methyl-5-(4,4,5,5-tetramethyl-1,3,2-dioxaborolan-2-yl)-1H-pyrazole (4.64 g, 22.29 mmol), potassium phosphate (10.92 g, 51.4 mmol), and Pd(AmPhos)$_2$Cl$_2$ (0.607 g, 0.857 mmol). Dioxane (30 mL) and water (10 mL) were added to give a thick suspension. The flask was fitted with a reflux condenser and placed in a 90° C. oil bath for 4 h. The mixture was removed from the heat, then diluted with water and extracted with EtOAc (3×). The combined organic extracts were dried over sodium sulfate, filtered and concentrated. The residue was partially purified twice by chromatography on silica gel, first with 25 to 75% EtOAc/Heptane, then with 20 to 70% EtOAc/Heptane. The partially purified material thus obtained was dissolved in methanol and loaded onto a 10 g SCX-2 ion exchange column. The column was eluted with methanol, then with 2N ammonia in methanol. The basic fractions were combined and concentrated to give 2-(1-methyl-1H-pyrazol-5-yl)-4-(trifluoromethyl)aniline (0.5526 g, 2.291 mmol, 13.36% yield) as a tan solid. $^1$H NMR (400 MHz, DMSO-d$_6$) δ=7.52 (d, J=1.9 Hz, 1 H), 7.43 (ddd, J=0.5, 2.3, 8.6 Hz, 1 H), 7.26 (d, J=1.9 Hz, 1 H), 6.88 (d, J=8.5 Hz, 1 H), 6.32 (d, J=1.9 Hz, 1 H), 5.62 (s, 2 H), 3.64 (s, 3 H). m/z (ESI) 242.2 (M+H)$^+$.

Intermediate M: N-(2,4-Dimethoxybenzyl)-4-Fluoro-3-Nitro-N-(1,2,4-Thiadiazol-5-yl)Benzenesulfonamide

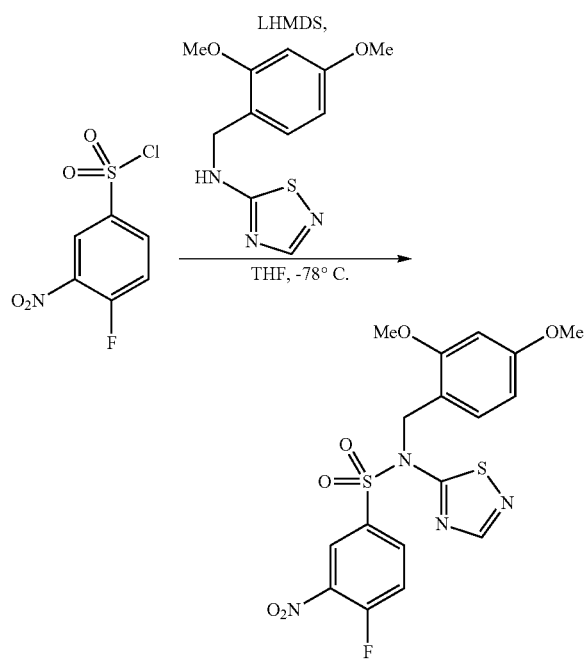

A round-bottom flask was charged with N-(2,4-dimethoxybenzyl)-1,2,4-thiadiazol-5-amine (851 mg, 3.39 mmol) and THF (10 mL) to give a clear, light yellow solution. The flask was cooled in a dry ice and acetone bath for 10 min, then lithium bis(trimethylsilyl)amide (1M in THF) (3387 μl, 3.39 mmol) was added dropwise over 1 minute to give a suspension. The flask was removed from the cooling bath for 10 min, then re-cooled for 5 min. A solution of 4-fluoro-3-nitrobenzene-1-sulfonyl chloride (737.72 mg, 3.08 mmol) in THF (3 mL with a 1 mL flask/syringe wash) was added dropwise over 2 min. The mixture was stirred for another 5 min, then the mixture was warmed to room temperature. The reaction mixture was diluted with water and extracted with EtOAc (3×). The combined organic extract was dried over sodium sulfate, filtered and concentrated. The crude product was purified by chromatography on silica gel (0 to 30% EtOAc/heptane) to give N-(2,4-dimethoxybenzyl)-4-fluoro-3-nitro-N-(1,2,4-thiadiazol-5-yl)benzenesulfonamide (758 mg, 1.668 mmol, 54.2% yield) as a yellow solid. $^1$H NMR (400 MHz, CHLOROFORM-d) δ=8.24 (s, 1 H), 8.18 (dd, J=2.4, 6.7 Hz, 1 H), 7.99 (ddd, J=2.4, 3.9, 8.8 Hz, 1 H), 7.33-7.28 (m, 1 H), 7.09 (d, J=8.4 Hz, 1 H), 6.32 (dd, J=2.3, 8.4 Hz, 1 H), 6.21 (d, J=2.4 Hz, 1 H), 5.37 (s, 2 H), 3.76 (s, 3 H), 3.63 (s, 3 H). m/z (ESI) 477.0 (M+H)$^+$.

Intermediate N: Tert-Butyl 4-(2-(4,4,5,5-Tetramethyl-1,3,2-Dioxaborolan-2-yl)-5-(Trifluoromethyl)Phenyl)-5,6-Dihydropyridine-1(2H)-Carboxylate

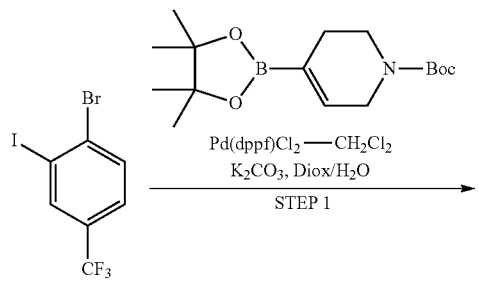

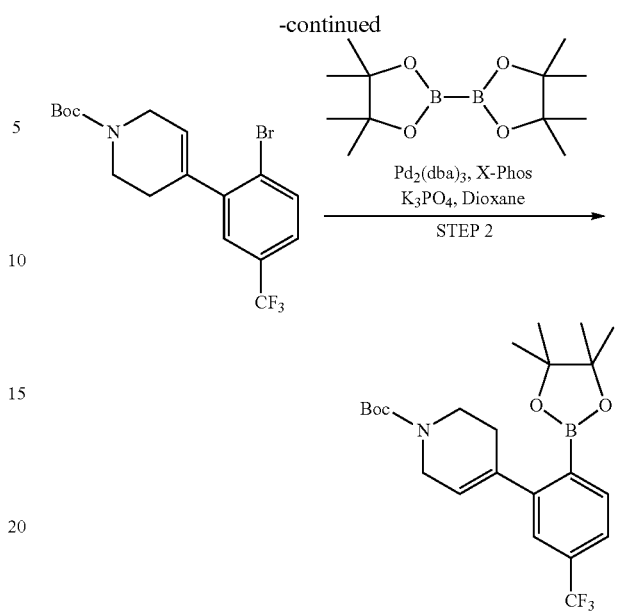

Step 1: Tert-Butyl 4-(2-Bromo-5-(Trifluoromethyl)Phenyl)-5,6-Dihydropyridine-1(2H)-Carboxylate A solution of 1-bromo-2-iodo-4-(trifluoromethyl)benzene (1.598 ml, 9.70 mmol), tert-butyl 4-(4,4,5,5-tetramethyl-1,3,2-dioxaborolan-2-yl)-5,6-dihydropyridine-1(2H)-carboxylate (3.00 g, 9.70 mmol), Pd(dppf)-CH$_2$Cl$_2$ adduct (0.396 g, 0.485 mmol), and potassium carbonate (2.329 g, 38.8 mmol) in 1,4-dioxane (36.4 ml) and water (12.13 ml) was stirred at 70° C. for 18 hours. The reaction was diluted with ethyl acetate and washed with water. The aqueous layer was extracted with ethyl acetate, and the combined organic layers were dried with sodium sulfate, filtered, and concentrated. The material was purified via column chromatography (RediSep Gold 80 g silica gel column (Teledyne Isco, Lincoln, Nebr.), gradient elution 0 to 100% Et$_2$O:Heptane) to afford tert-butyl 4-(2-bromo-5-(trifluoromethyl)phenyl)-5,6-dihydropyridine-1(2H)-carboxylate as a light yellow oil. m/z (ESI) 428.1 (M+Na)$^+$.

Step 2: Tert-Butyl 4-(2-(4,4,5,5-Tetramethyl-1,3,2-Dioxaborolan-2-yl)-5-(Trifluoromethyl)Phenyl)-5,6-Dihydropyridine-1(2H)-Carboxylate A round bottom flask was charged with tert-butyl 4-(2-bromo-5-(trifluoromethyl)phenyl)-5,6-dihydropyridine-1(2H)-carboxylate (2.32 g, 5.71 mmol), bis(pinacolato)diboron (2.90 g, 11.42 mmol), potassium phosphate (3.64 g, 17.13 mmol), pd2(dba)$_3$ (0.261 g, 0.286 mmol), and X-Phos (0.272 g, 0.571 mmol). 1,4-Dioxane (28.6 ml) was added, the flask was fitted with a reflux condenser, and the reaction was heated to 90° C. and stirred for four hours. The reaction was cooled to room temperature, filtered through diatomaceous earth, and washed with ethyl acetate. The filtrate was concentrated and purified via column chromatography (RediSep Gold 80 g silica gel column (Teledyne Isco, Lincoln, Nebr.), gradient elution 0 to 25% ether:heptane) to afford tert-butyl 4-(2-(4,4,5,5-tetramethyl-1,3,2-dioxaborolan-2-yl)-5-(trifluoromethyl)phenyl)-5,6-dihydropyridine-1(2H)-carboxylate as a yellow oil. m/z (ESI) 354.4 (M+H)$^+$.

Intermediate O: Tert-Butyl 4-(2-(1-Methyl-6-((Perfluorophenoxy)Sulfonyl)-1H-Indol-3-yl)-5-(Trifluoromethyl)Phenyl)-5,6-Dihydropyridine-1(2H)-Carboxylate

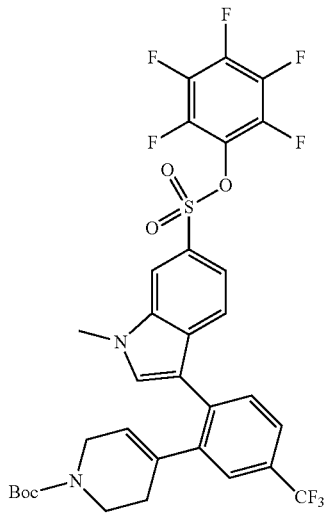 [SMILES: Cn1cc(-c2ccc(C(F)(F)F)cc2C2=CCN(C(=O)OC(C)(C)C)CC2)c2ccc(S(=O)(=O)Oc3c(F)c(F)c(F)c(F)c3F)cc21]

The title compound was prepared in an analogous manner to that described in Intermediate E using perfluorophenyl 3-bromo-1-methyl-1H-indole-6-sulfonate and tert-butyl 4-(2-(4,4,5,5-tetramethyl-1,3,2-dioxaborolan-2-yl)-5-(trifluoromethyl)phenyl)-5,6-dihydropyridine-1(2H)-carboxylate (INTERMEDIATE N) as the coupling partners to afford tert-butyl 4-(2-(1-methyl-6-((perfluorophenoxy)sulfonyl)-1H-indol-3-yl)-5-(trifluoromethyl)phenyl)-5,6-dihydropyridine-1(2H)-carboxylate as an orange oily solid. m/z (ESI) 726.3 (M+Na)$^+$. $^1$H NMR (400 MHz, DMSO-d$_6$) δ ppm=8.26 (d, J=1.5 Hz, 1 H), 7.95 (s, 1 H), 7.77-7.73 (m, 1 H), 7.72 (d, J=8.5 Hz, 1 H), 7.66 (d, J=8.0 Hz, 1 H), 7.63 (d, J=1.9 Hz, 1 H), 7.59 (dd, J=1.8, 8.6 Hz, 1 H), 5.82 (br. s., 1 H), 3.99 (s, 3 H), 3.84 (br. s., 2 H), 3.10 (t, J=5.5 Hz, 2 H), 1.89 (br. s., 2 H), 1.38-1.29 (m, 9 H).

Example 1

3-(4-Chloro-2-(1-Methyl-1H-Pyrazol-5-yl)Phenyl)-N-(1,2,4-Thiadiazol-5-yl)-1H-Indole-6-Sulfonamide

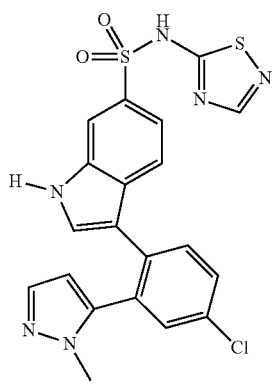 [SMILES: Cn1nccc1-c1cc(Cl)ccc1-c1c[nH]c2cc(S(=O)(=O)Nc3ncns3)ccc12]

Step 1: 3-(4-Chloro-2-(1-Methyl-1H-Pyrazol-5-yl)Phenyl)-N-(2,4-Dimethoxybenzyl)-N-(1,2,4-Thiadiazol-5-yl)-1H-Indole-6-Sulfonamide A microwave vial was charged with 3-bromo-N-(2,4-dimethoxybenzyl)-N-(1,2,4-thiadiazol-5-yl)-1H-indole-6-sulfonamide (83.6 mg, 0.164 mmol), (4-chloro-2-(1-methyl-1H-pyrazol-5-yl)phenyl)boronic acid (Intermediate F) (50.4 mg, 0.213 mmol), potassium phosphate (105 mg, 0.492 mmol), and Pd(AmPhos)$_2$Cl$_2$ (5.81 mg, 8.21 μmol). The vial was flushed with Ar, then dioxane (0.6 mL) and water (0.2 mL) were added. The vial was sealed and heated in a microwave reactor for 20 min at 90° C. The mixture was extracted with EtOAc (3×), and the combined organic extracts were concentrated. The crude product was purified by chromatography on silica gel (0 to 100% EtOAc/Heptane) to give 3-(4-chloro-2-(1-methyl-1H-pyrazol-5-yl)phenyl)-N-(2,4-dimethoxybenzyl)-N-(1,2,4-thiadiazol-5-yl)-1H-indole-6-sulfonamide (74 mg, 0.119 mmol, 72.6% yield) as an off-white foam. $^1$H NMR (400 MHz, DMSO-d$_6$) δ=11.81 (s, 1 H), 8.34 (s, 1 H), 8.01-7.94 (m, 1 H), 7.70-7.58 (m, 3 H), 7.55-7.51 (m, 1 H), 7.45 (dd, J=1.9, 8.6 Hz, 1 H), 7.36 (d, J=1.9 Hz, 1 H), 7.16 (s, 1 H), 6.91 (d, J=8.4 Hz, 1 H), 6.45 (d, J=2.4 Hz, 1 H), 6.37 (dd, J=2.4, 8.5 Hz, 1 H), 6.28 (d, J=1.9 Hz, 1 H), 5.08 (s, 2 H), 3.72 (s, 3 H), 3.68 (s, 3 H), 3.21 (s, 3 H). m/z (ESI) 621.0 (M+H)$^+$.

Step 2: 3-(4-Chloro-2-(1-Methyl-1H-Pyrazol-5-yl)Phenyl)-N-(1,2,4-Thiadiazol-5-yl)-1H-Indole-6-Sulfonamide A vial was charged with 3-(4-chloro-2-(1-methyl-1H-pyrazol-5-yl)phenyl)-N-(2,4-dimethoxybenzyl)-N-(1,2,4-thiadiazol-5-yl)-1H-indole-6-sulfonamide (Intermediate A) (28.44 mg, 0.046 mmol) in methanol (0.5 mL). Hydrogen chloride (4M in 1,4-dioxane) (114 μl, 0.458 mmol) was added, and the resulting mixture was stirred for 30 min. The mixture was diluted with DCM and concentrated in vacuo. The residue was suspended in MeOH, then filtered through Celite® (diatomaceous earth). The filtrate was concentrated, and the residue was dissolved in methanol and loaded onto a 500 mg SCX-2 ion exchange column. The column was eluted with methanol, then with a solution of 2N ammonia in methanol. The basic fractions were concentrated to give 3-(4-chloro-2-(1-methyl-1H-pyrazol-5-yl)phenyl)-N-(1,2,4-thiadiazol-5-yl)-1H-indole-6-sulfonamide 3-(4-chloro-2-(1-methyl-1H-pyrazol-3-yl)phenyl)-N-(1,2,4-thiadiazol-5-yl)-1H-indole-6-sulfonamide (19.36 mg, 0.041 mmol, 90% yield) as a light-yellow solid. $^1$H NMR (400 MHz, DMSO-d$_6$) δ=11.57 (br. s., 1 H), 8.05 (s, 1 H), 7.85 (dd, J=0.5, 1.6 Hz, 1 H), 7.71-7.58 (m, 2 H), 7.54 (d, J=8.5 Hz, 1 H), 7.49 (d, J=2.2 Hz, 1 H), 7.43-7.33 (m, 2 H), 7.23-7.04 (m, 1 H), 6.93 (d, J=2.6 Hz, 1 H), 6.30 (d, J=1.9 Hz, 1 H), 3.19 (br. s., 1 H). m/z (ESI) 471.0 (M+H)$^+$.

Example 2

3-(4-Chloro-2-(1-Methyl-1H-Pyrazol-5-yl)Phenyl)-1-Methyl-N-(1,2,4-Thiadiazol-5-yl)-1H-Indole-6-Sulfonamide

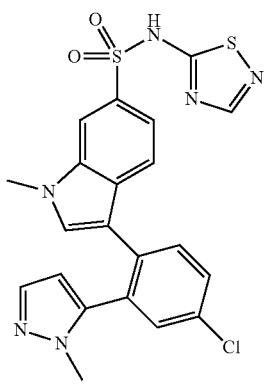 [SMILES: Cn1nccc1-c1cc(Cl)ccc1-c1cn(C)c2cc(S(=O)(=O)Nc3ncns3)ccc12]

Step 1: N-(2,4-Dimethoxybenzyl)-1-Methyl-3-(2-(1-Methyl-1H-Pyrazol-5-yl)-4-(Trifluoromethyl)Phenyl)-N-(1,2,4-Thiadiazol-5-yl)-1H-Indole-6-Sulfonamide A 10-mL round-bottom flask was charged with 3-(4-chloro-2-(1-methyl-1H-pyrazol-5-yl)phenyl)-N-(2,4-dimethoxybenzyl)-N-(1,2,4-thiadiazol-5-yl)-1H-indole-6-sulfonamide (prepared in Step 1 of Example 1) (41.46 mg, 0.067 mmol) in THF (1 mL). The flask was cooled in an ice bath for 5 min, then lithium bis(trimethylsilyl)amide (1M in THF) (80 μl, 0.080 mmol) was added dropwise to give a bright-yellow solution. After 10 min, iodomethane (5.01 μl, 0.080 mmol) was added, and the cooling bath was removed. The mixture was stirred overnight. In the morning, additional portions of lithium bis(trimethylsilyl)amide (1M in THF) (80 μl, 0.080 mmol) and iodomethane (0.010 mL) were added in sequence. The vial was sealed and placed in a 60° C. oil bath for 45 min. The reaction mixture was cooled to room temperature and subjected directly to chromatography on silica gel (0 to 100% EtOAc/Heptane) to give N-(2,4-dimethoxybenzyl)-1-methyl-3-(2-(1-methyl-1H-pyrazol-5-yl)-4-(trifluoromethyl)phenyl)-N-(1,2,4-thiadiazol-5-yl)-1H-indole-6-sulfonamide (35.79 mg, 0.056 mmol, 84% yield) as a white solid. m/z (ESI) 635.2 (M+H)$^+$.

Step 2: 3-(4-Chloro-2-(1-Methyl-1H-Pyrazol-5-yl)Phenyl)-1-Methyl-N-(1,2,4-Thiadiazol-5-yl)-1H-Indole-6-Sulfonamide A 10-mL round-bottom flask was charged with N-(2,4-dimethoxybenzyl)-1-methyl-3-(2-(1-methyl-1H-pyrazol-5-yl)-4-(trifluoromethyl)phenyl)-N-(1,2,4-thiadiazol-5-yl)-1H-indole-6-sulfonamide (35.79 mg, 0.056 mmol) and methanol (1 mL). Hydrogen chloride (4M in 1,4-dioxane) (141 μl, 0.563 mmol) was added, and the resulting solution was stirred for 45 min. The reaction mixture was loaded onto a 500 mg SCX-2 ion exchange column (Silicycle, Quebec City, Canada). The column was eluted with methanol, then with a solution of 2N ammonia in methanol. The basic fractions were combined and concentrated. The residue was purified further by chromatography on silica gel (0 to 10% MeOH/DCM) to give 3-(4-chloro-2-(1-methyl-1H-pyrazol-5-yl)phenyl)-1-methyl-N-(1,2,4-thiadiazol-5-yl)-1H-indole-6-sulfonamide (12.05 mg, 0.025 mmol, 44.1% yield) as a cream colored solid. $^1$H NMR (400 MHz, DMSO-d$_6$) δ=8.35 (br. s., 1 H), 7.90 (d, J=1.1 Hz, 1 H), 7.62 (d, J=1.3 Hz, 2 H), 7.56-7.31 (m, 4 H), 7.12 (s, 1 H), 6.27 (d, J=1.9 Hz, 1 H), 3.79 (s, 3 H), 3.23 (s, 3 H). m/z (ESI) 485.1 (M+H)$^+$.

Example 3

1-Isopropyl-3-(2-(1-Methyl-1H-Pyrazol-5-yl)-4-(Trifluoromethyl)Phenyl)-N-(1,2,4-Thiadiazol-5-yl)-1H-Indole-6-Sulfonamide

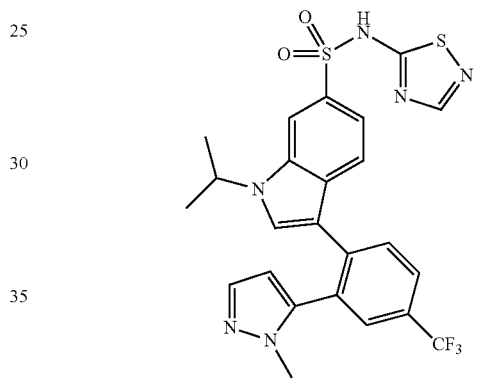

A vial was charged with N-(2,4-dimethoxybenzyl)-3-(2-(1-methyl-1H-pyrazol-5-yl)-4-(trifluoromethyl)phenyl)-N-(1,2,4-thiadiazol-5-yl)-1H-indole-6-sulfonamide (Intermediate B) (57.4 mg, 0.088 mmol), cesium carbonate (86 mg, 0.263 mmol), acetonitrile (0.5 mL), and 2-iodopropane (26.3 μl, 0.263 mmol). The vial was sealed and heated to 70° C. for 1 h. The mixture was cooled to room temperature, diluted with water, and extracted with EtOAc (2×). The combined organic extracts were dried over sodium sulfate, filtered, and concentrated. The residue was taken up on in MeOH (1 mL), then acetyl chloride (31.2 μl, 0.438 mmol) was added. After stirring for 1 h, the mixture was concentrated in vacuo. The residue was taken up in a solution of 2N ammonia in methanol, and the resulting slurry was concentrated in vacuo. The crude product was purified by chromatography on silica gel (0 to 10% MeOH/DCM) to give 1-isopropyl-3-(2-(1-methyl-1H-pyrazol-5-yl)-4-(trifluoromethyl)phenyl)-N-(1,2,4-thiadiazol-5-yl)-1H-indole-6-sulfonamide (38.52 mg, 0.070 mmol, 80% yield) as a light-yellow solid. $^1$H NMR (400 MHz, DMSO-d$_6$) δ=8.36 (s, 1 H), 8.00 (d, J=1.5 Hz, 1 H), 7.96-7.89 (m, 2 H), 7.79-7.75 (m, 1H), 7.70 (d, J=8.5 Hz, 1 H), 7.48 (dd, J=1.7, 8.5 Hz, 1 H), 7.44 (d, J=1.9 Hz, 1 H), 7.09 (s, 1 H), 6.42 (d, J=1.9 Hz, 1 H), 4.86 (td, J=6.5, 13.2 Hz, 1 H), 1.33 (d, J=6.6 Hz, 6 H). m/z (ESI) 547.2 (M+H)$^+$.

Example 4

1-Acetyl-3-(2-(1-Methyl-1H-Pyrazol-5-yl)-4-(Trifluoromethyl)Phenyl)-N-(1,2,4-Thiadiazol-5-yl)-1H-Indole-6-Sulfonamide

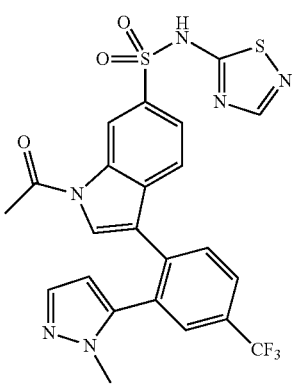 [SMILES: CC(C)n1cc(-c2ccc(C(F)(F)F)cc2-c2ccnn2C)c2ccc(S(=O)(=O)Nc3ncns3)cc21]

A 10-mL round-bottom flask was charged with N-(2,4-dimethoxybenzyl)-3-(2-(1-methyl-1H-pyrazol-5-yl)-4-(trifluoromethyl)phenyl)-N-(1,2,4-thiadiazol-5-yl)-1H-indole-6-sulfonamide (Intermediate B) (85.95 mg, 0.131 mmol) and DMF (1.3 mL) to give a clear, light-yellow solution. Sodium hydride (60% in mineral oil) (7.88 mg, 0.197 mmol) was added, and the resulting mixture was stirred for 15 min. Acetic anhydride (24.77 μl, 0.263 mmol) was added dropwise to give a thick slurry. After 15 min of stirring, the mixture was diluted with water, EtOAc, and a small amount of brine. The layers were separated, and the aq. layer was extracted with EtOAc. The organic extracts were combined, dried over sodium sulfate, and concentrated. The residue was dissolved in MeOH (1 mL) and treated dropwise with acetyl chloride (46.7 μl, 0.656 mmol) for 1.5 h. The reaction mixture was concentrated in vacuo, and the residue was suspended in DCM (2 mL) and triethylamine (0.5 mL). The resulting solution was again concentrated, and the crude product was purified by chromatography on silica gel (0 to 10% MeOH/DCM) to give 1-acetyl-3-(2-(1-methyl-1H-pyrazol-5-yl)-4-(trifluoromethyl)phenyl)-N-(1,2,4-thiadiazol-5-yl)-1H-indole-6-sulfonamide (48.77 mg, 0.089 mmol, 68.0% yield) as a yellow solid. $^1$H NMR (400 MHz, DMSO-$d_6$) δ=8.82 (dd, J=0.5, 1.7 Hz, 1 H), 8.42 (s, 1 H), 8.06-7.97 (m, 1 H), 7.93-7.85 (m, 3 H), 7.60 (dd, J=1.8, 8.4 Hz, 1 H), 7.41 (d, J=8.4 Hz, 1 H), 7.33 (s, 1 H), 6.31 (d, J=1.9 Hz, 1 H), 3.43 (s, 3 H), 2.59 (s, 3 H). m/z (ESI) 547.2 (M+H)$^+$.

Example 5

3-(2-(1-Methyl-1H-Pyrazol-5-yl)-4-(Trifluoromethyl)Phenyl)-N-(1,2,4-Thiadiazol-5-yl)-1H-Indole-6-Sulfonamide

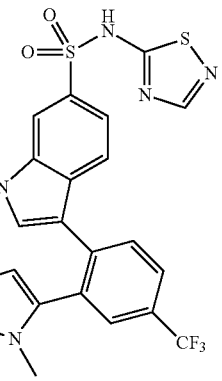

The title compound was prepared in an analogous manner to Example 4, except that the triethylamine quench of the deprotection reaction was replaced with 2N ammonia in methanol. This resulted in deacylation to give the 3-(2-(1-methyl-1H-pyrazol-5-yl)-4-(trifluoromethyl)phenyl)-N-(1,2,4-thiadiazol-5-yl)-1H-indole-6-sulfonamide as an off-white solid. $^1$H NMR (400 MHz, DMSO-$d_6$) δ=11.75 (d, J=2.3 Hz, 1 H), 8.25 (s, 1 H), 7.95-7.86 (m, 3 H), 7.75 (s, 1 H), 7.63 (d, J=8.5 Hz, 1 H), 7.46-7.35 (m, 2 H), 7.05 (d, J=2.7 Hz, 1 H), 6.38 (d, J=1.9 Hz, 1 H), 3.17 (s, 3 H). m/z (ESI) 505.0 (M+H)$^+$.

Example 6

Methyl 6-(N-(1,2,4-Thiadiazol-5-yl)Sulfamoyl)-3-(2-(1-Methyl-1H-Pyrazol-5-yl)-4-(Trifluoromethyl)Phenyl)-1H-Indole-1-Carboxylate

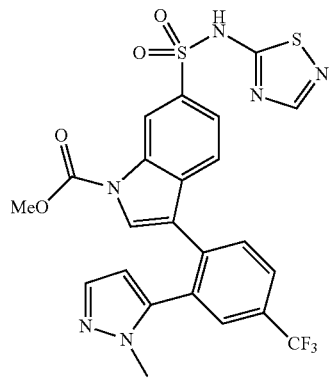 [SMILES: COC(=O)n1cc(-c2ccc(C(F)(F)F)cc2-c2ccnn2C)c2ccc(S(=O)(=O)Nc3ncns3)cc21]

The title compound was prepared in an analogous manner to that described in Example 4 using methyl chloroformate instead of acetic anhydride, and the desired product, methyl 6-(N-(1,2,4-thiadiazol-5-yl)sulfamoyl)-3-(2-(1-methyl-1H-pyrazol-5-yl)-4-(trifluoromethyl)phenyl)-1H-indole-1-carboxylate, was isolated as a yellow solid. $^1$H NMR (400 MHz, DMSO-$d_6$) δ=8.59 (d, J=1.2 Hz, 1 H), 8.41 (s, 1 H), 8.01-7.94 (m, 1 H), 7.90-7.86 (m, 2 H), 7.70 (s, 1 H), 7.62 (dd, J=1.7, 8.4

Hz, 1 H), 7.48 (d, J=8.4 Hz, 1 H), 7.33 (d, J=1.9 Hz, 1 H), 6.30 (d, J=1.9 Hz, 1 H), 4.01 (s, 3 H), 3.39 (s, 3H). m/z (ESI) 563.0 (M+H)$^+$.

Example 7

3-(2-(1-Methyl-1H-Pyrazol-5-yl)-4-(Trifluoromethyl)Phenyl)-1-(Methylsulfonyl)-N-(1,2,4-Thiadiazol-5-yl)-1H-Indole-6-Sulfonamide

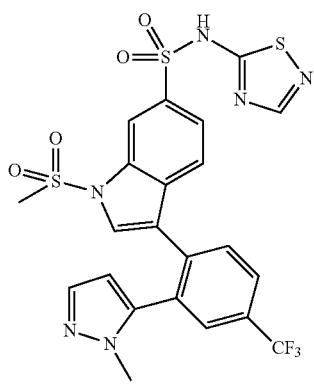 [SMILES: Cn1nccc1-c1cc(C(F)(F)F)ccc1-c1cn(S(C)(=O)=O)c2cc(S(=O)(=O)Nc3ncns3)ccc12]

The title compound was prepared in an analogous manner to that described in Example 4 using methanesulfonyl chloride instead of acetic anhydride, and the desired product, 3-(2-(1-methyl-1H-pyrazol-5-yl)-4-(trifluoromethyl)phenyl)-1-(methylsulfonyl)-N-(1,2,4-thiadiazol-5-yl)-1H-indole-6-sulfonamide was isolated as a cream colored solid. $^1$H NMR (400 MHz, DMSO-d$_6$) δ=8.40-8.25 (m, 2 H), 8.02-7.92 (m, 2 H), 7.89 (s, 1 H), 7.70-7.64 (m, 1 H), 7.60-7.56 (m, 1 H), 7.46 (s, 1 H), 7.37 (d, J=2.0 Hz, 1 H), 6.34 (d, J=2.0 Hz, 1 H), 3.44 (s, 3 H), 3.35 (s, 3 H). m/z (ESI) 583.0 (M+H)$^+$.

Example 8

1-Methyl-3-(2-(1-Methyl-1H-Pyrazol-5-yl)-4-(Trifluoromethyl)Phenyl)-N-(1,2,4-Thiadiazol-5-yl)-1H-Indole-6-Sulfonamide

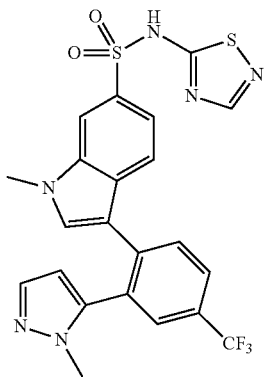

A microwave vial was charged with 3-bromo-N-(2,4-dimethoxybenzyl)-1-methyl-N-(1,2,4-thiadiazol-5-yl)-1H-indole-6-sulfonamide (Intermediate D) (48.17 mg, 0.092 mmol), (2-(1-methyl-1H-pyrazol-5-yl)-4-(trifluoromethyl)phenyl)boronic acid (Intermediate G) (32.3 mg, 0.120 mmol), potassium phosphate (58.6 mg, 0.276 mmol), and Pd(AmPhos)$_2$Cl$_2$ (3.26 mg, 4.60 µmol). The vial was flushed with Ar, then 1,4-dioxane (0.4 mL) and water (0.125 mL) were added in sequence. The vial was sealed and heated in a microwave reactor at 90° C. for 20 min. The mixture was diluted with water, then extracted with EtOAc (3×). The combined organic extracts were concentrated. The residue was taken up in MeOH (1 mL), and cooled in an ice bath for 5 min. Acetyl chloride (65.4 µl, 0.920 mmol) was added dropwise, and the resulting mixture was stirred for 2 h. The mixture was concentrated under vacuum to remove excess HCl, and the residue was taken up in 2N ammonia in methanol. The resulting mixture was again concentrated under vacuum. The crude product was purified by chromatography on silica gel (0 to 10% MeOH/DCM) to give 1-methyl-3-(2-(1-methyl-1H-pyrazol-5-yl)-4-(trifluoromethyl)phenyl)-N-(1,2,4-thiadiazol-5-yl)-1H-indole-6-sulfonamide (35.38 mg, 0.068 mmol, 74.1% yield) as a light-yellow solid. $^1$H NMR (400 MHz, DMSO-d$_6$) δ=8.37 (s, 1 H), 7.97-7.83 (m, 3 H), 7.77 (d, J=1.9 Hz, 1 H), 7.60-7.53 (m, 1 H), 7.47-7.36 (m, 2 H), 7.17 (s, 1 H), 6.35 (d, J=1.9 Hz, 1 H), 3.81 (s, 3 H), 3.22 (s, 3 H). m/z (ESI) 519.2 (M+H)$^+$.

Example 9

1-Methyl-3-(Pyridin-3-yl)-N-(1,2,4-Thiadiazol-5-yl)-1H-Indole-6-Sulfonamide

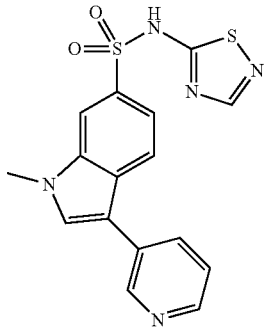 [SMILES: Cn1cc(-c2cccnc2)c2ccc(S(=O)(=O)Nc3ncns3)cc21]

The title compound was prepared in an analogous manner to that described for Example 8 using pyridin-3-ylboronic acid, and the desired product, 1-methyl-3-(pyridin-3-yl)-N-(1,2,4-thiadiazol-5-yl)-1H-indole-6-sulfonamide, was isolated as a light-yellow solid. $^1$H NMR (400 MHz, DMSO-d$_6$) δ=8.90 (dd, J=0.8, 2.3 Hz, 1 H), 8.47 (dd, J=1.6, 4.7 Hz, 1 H), 8.27 (s, 1 H), 8.11-7.91 (m, 4 H), 7.56 (dd, J=1.7, 8.5 Hz, 1 H), 7.47 (ddd, J=0.9, 4.8, 7.9 Hz, 1 H), 3.94 (s, 3 H). m/z (ESI) 372.2 (M+H)$^+$.

Example 10

3-(2,5-Difluorophenyl)-1-Methyl-N-(1,2,4-Thiadiazol-5-yl)-1H-Indole-6-Sulfonamide

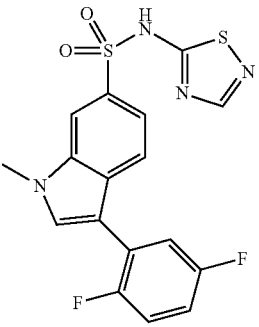 [SMILES: Cn1cc(-c2cc(F)ccc2F)c2ccc(S(=O)(=O)Nc3ncns3)cc21]

The title compound was prepared in an analogous manner to that described for Example 8 using (2,5-difluorophenyl)boronic acid, and the desired product, 3-(2,5-difluorophenyl)-1-methyl-N-(1,2,4-thiadiazol-5-yl)-1H-indole-6-sulfonamide, was isolated as a light-yellow solid. $^1$H NMR (400 MHz, DMSO-d$_6$) δ=8.41 (s, 1 H), 7.99 (dd, J=1.5, 12.2 Hz, 2 H), 7.84 (dd, J=1.5, 8.6 Hz, 1 H), 7.56 (dd, J=1.7, 8.5 Hz, 1 H), 7.49 (ddd, J=3.2, 6.0, 9.3 Hz, 1 H), 7.39 (ddd, J=4.8, 9.1, 10.1 Hz, 1 H), 7.23-7.12 (m, 1 H), 3.96 (s, 3 H). m/z (ESI) 407.0 (M+H)$^+$.

Example 11

1-Methyl-3-(2-(1-Methyl-1H-Pyrazol-5-yl)-4-(Trifluoromethyl)Phenyl)-N-(Thiazol-2-yl)-1H-Indole-6-Sulfonamide

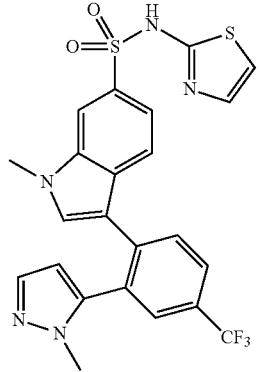 [SMILES: Cn1nccc1-c1cc(C(F)(F)F)ccc1-c1cn(C)c2cc(S(=O)(=O)Nc3nccs3)ccc12]

A vial was charged with perfluorophenyl 1-methyl-3-(2-(1-methyl-1H-pyrazol-5-yl)-4-(trifluoromethyl)phenyl)-1H-indole-6-sulfonate (Intermediate E) (32.98 mg, 0.055 mmol), thiazol-2-amine (7.14 mg, 0.071 mmol), and THF (0.4 mL) to give a clear solution. Lithium bis(trimethylsilyl)amide (1M in THF) (137 µl, 0.137 mmol) was added dropwise over 5 min, and the resulting solution was stirred overnight. In the morning, acetic acid (0.03 mL) was added, resulting in a viscous mixture. The mixture was diluted with DCM/MeOH, transferred to a flask, and concentrated in vacuo. The crude product was purified by chromatography on silica gel (0 to 5% MeOH/DCM) to give 1-methyl-3-(2-(1-methyl-1H-pyrazol-5-yl)-4-(trifluoromethyl)phenyl)-N-(thiazol-2-yl)-1H-indole-6-sulfonamide (20.6 mg, 0.040 mmol, 72.6% yield) as a tan solid. $^1$H NMR (400 MHz, DMSO-d$_6$) δ=7.96-7.83 (m, 3 H), 7.78-7.71 (m, 1 H), 7.60-7.43 (m, 2 H), 7.40 (d, J=1.9 Hz, 1 H), 7.21 (s, 1 H), 7.12 (s, 1 H), 6.79 (d, J=4.6 Hz, 1 H), 6.36 (s, 1 H), 3.80 (s, 3 H), 3.22 (s, 3 H). m/z (ESI) 518.2 (M+H)$^+$.

Example 12

1-Methyl-3-(2-(1-Methyl-1H-Pyrazol-5-yl)-4-(Trifluoromethyl)Phenyl)-N-(Pyrimidin-4-yl)-1H-Indole-6-Sulfonamide

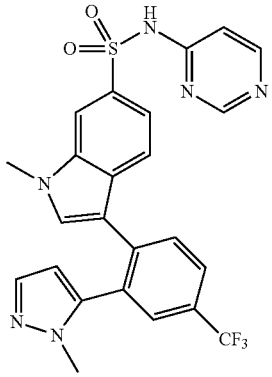 [SMILES: Cn1nccc1-c1cc(C(F)(F)F)ccc1-c1cn(C)c2cc(S(=O)(=O)Nc3ccncn3)ccc12]

The title compound was prepared in an analogous manner to that described for Example 11, except that pyrimidin-4-amine was used in place of 2-aminothiazole, and the reaction was run at 0° C. instead of room temperature. The desired product, 1-methyl-3-(2-(1-methyl-1H-pyrazol-5-yl)-4-(trifluoromethyl)phenyl)-N-(pyrimidin-4-yl)-1H-indole-6-sulfonamide, was isolated as a white solid. $^1$H NMR (400 MHz, DMSO-d$_6$) δ=12.17 (br. s., 1 H), 8.62 (s, 1 H), 8.33 (d, J=5.5 Hz, 1 H), 8.11 (s, 1 H), 7.95-7.83 (m, 2 H), 7.77 (s, 1 H), 7.62-7.49 (m, 2 H), 7.38 (d, J=1.9 Hz, 1 H), 7.18 (s, 1 H), 7.08 (d, J=6.0 Hz, 1 H), 6.34 (d, J=1.9 Hz, 1 H), 3.83 (s, 3 H), 3.22 (s, 3 H). m/z (ESI) 513.2 (M+H)$^+$.

Example 13

1-Methyl-3-(2-(1-Methyl-1H-Pyrazol-5-yl)-4-(Trifluoromethyl)Phenyl)-N-(1,3,4-Thiadiazol-2-yl)-1H-Indole-6-Sulfonamide

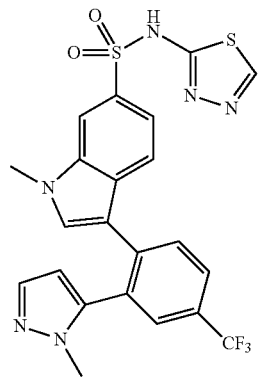 [SMILES: Cn1nccc1-c1cc(C(F)(F)F)ccc1-c1cn(C)c2cc(S(=O)(=O)Nc3nncs3)ccc12]

The title compound was prepared in an analogous manner to that described for Example 11, except that 1,3,4-thiadiazol-2-amine was used in place of 2-aminothiazole, and the reaction was run at 0° C. instead of room temperature. The desired product, 1-methyl-3-(2-(1-methyl-1H-pyrazol-5-yl)-4-(trifluoromethyl)phenyl)-N-(1,3,4-thiadiazol-2-yl)-1H-indole-6-sulfonamide, was isolated as a white solid. $^1$H NMR (400 MHz, DMSO-d$_6$) δ=14.20 (br. s., 1 H), 8.73 (s, 1 H), 7.96-7.84 (m, 3 H), 7.77 (s, 1 H), 7.58 (s, 1 H), 7.48-7.35 (m, 2 H), 7.17 (s, 1 H), 6.36 (d, J=1.9 Hz, 1 H), 3.82 (s, 3 H), 3.22 (s, 3 H). m/z (ESI) 519.1 (M+H)$^+$.

Example 14

1-Methyl-3-(5-(Prop-1-Yn-1-yl)Pyridin-3-yl)-N-(1,2,4-Thiadiazol-5-yl)-1H-Indole-6-Sulfonamide

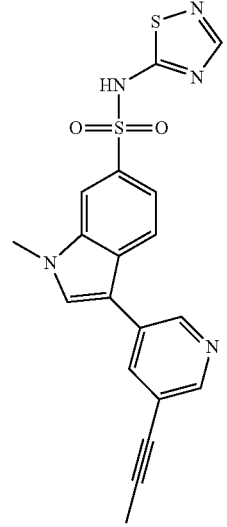 [SMILES: CC#Cc1cncc(-c2cn(C)c3cc(S(=O)(=O)Nc4ncns4)ccc23)c1]

The title compound was prepared in an analogous manner to that described in Example 8 using (5-(prop-1-yn-1-yl)pyridin-3-yl)boronic acid (prepared as described in PCT patent application publication no. WO201102407A1). The desired product, 1-methyl-3-(5-(prop-1-yn-1-yl)pyridin-3-yl)-N-(1,2,4-thiadiazol-5-yl)-1H-indole-6-sulfonamide, was isolated as a yellow solid. $^1$H NMR (400 MHz, DMSO-$d_6$) δ=8.83 (d, J=2.2 Hz, 4 H), 8.45 (d, J=2.0 Hz, 4 H), 8.04 (s, 1 H), 8.01 (d, J=4.1 Hz, 1 H), 7.94-7.87 (m, 3 H), 7.60-7.53 (m, 1 H), 3.90 (s, 3 H), 2.11 (s, 3 H). m/z (ESI) 410.2 (M+H)$^+$.

Example 15

1-Methyl-3-(3-(Pyridin-4-yl)-5-(Trifluoromethyl)Phenyl)-N-(1,2,4-Thiadiazol-5-yl)-1H-Indole-6-Sulfonamide

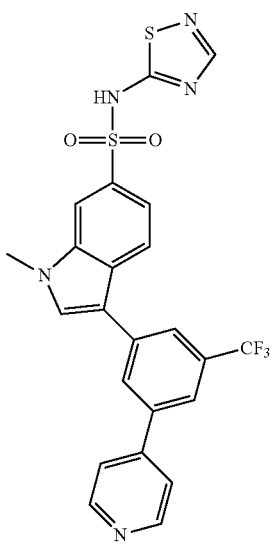 [SMILES: Cn1cc(-c2cc(-c3ccncc3)cc(C(F)(F)F)c2)c2ccc(S(=O)(=O)Nc3ncns3)cc21]

Step 1: 3-(3-BROMO-5-(TRIFLUOROMETHYL)PHENYL)-N-(2,4-Dimethoxybenzyl)-1-Methyl-N-(1,2,4-thiadiazol-5-yl)-1H-Indole-6-Sulfonamide A vial was charged with N-(2,4-dimethoxybenzyl)-1-methyl-3-(4,4,5,5-tetramethyl-1,3,2-dioxaborolan-2-yl)-N-(1,2,4-thiadiazol-5-yl)-1H-indole-6-sulfonamide (0.200 g, 0.351 mmol), potassium phosphate (0.260 g, 1.227 mmol), and PdCl$_2$(dppf)-CH$_2$Cl$_2$ (0.029 g, 0.035 mmol). DMF (0.150 mL) was added, followed by 1,3-dibromo-5-(trifluoromethyl)benzene (0.166 ml, 1.052 mmol). The vial was flushed with argon, sealed, and stirred at 85° C. for two hours. The reaction was diluted with ethyl acetate and washed with water. The aqueous layer was extracted with ethyl acetate, and the combined organic layers were washed with brine, dried with sodium sulfate, filtered, and concentrated. The material was purified via column chromatography (silica gel, gradient elution 0 to 75% EtOAc:Hexane) to afford 3-(3-bromo-5-(trifluoromethyl)phenyl)-N-(2,4-dimethoxybenzyl)-1-methyl-N-(1,2,4-thiadiazol-5-yl)-1H-indole-6-sulfonamide (0.081 g, 0.121 mmol, 34.6% yield) as a white solid. m/z (ESI) 668.0 (M+H)$^+$.

Step 2: N-(2,4-Dimethoxybenzyl)-1-Methyl-3-(3-(Pyridin-4-yl)-5-(Trifluoromethyl)Phenyl)-N-(1,2,4-Thiadiazol-5-yl)-1H-Indole-6-Sulfonamide A microwave vial was charged with 3-(3-bromo-5-(trifluoromethyl)phenyl)-N-(2,4-dimethoxybenzyl)-1-methyl-N-(1,2,4-thiadiazol-5-yl)-1H-indole-6-sulfonamide (0.050 g, 0.075 mmol), pyridin-4-ylboronic acid (0.018 g, 0.150 mmol), potassium phosphate (0.056 g, 0.262 mmol), and Pd(AmPhos)$_2$Cl$_2$ (5.30 mg, 7.49 µmol). The vial was flushed with Ar, then dioxane (0.375 ml) and water (0.125 ml) were added in sequence. The vial was sealed and microwaved at 100° C. for 30 minutes. The reaction was diluted with ethyl acetate and washed with water. The aqueous layer was extracted with ethyl acetate, and the combined organic layers were washed with brine, dried with sodium sulfate, filtered and concentrated. The material was purified via column chromatography (silica gel, gradient elution 0 to 100% EtOAc/Heptane) to afford N-(2,4-dimethoxybenzyl)-1-methyl-3-(3-(pyridin-4-yl)-5-(trifluoromethyl)phenyl)-N-(1,2,4-thiadiazol-5-yl)-1H-indole-6-sulfonamide as a yellow solid. m/z (ESI) 666.2 (M+H)$^+$.

Step 3: 1-Methyl-3-(3-(Pyridin-4-yl)-5-(Trifluoromethyl)Phenyl)-N-(1,2,4-Thiadiazol-5-yl)-1H-Indole-6-Sulfonamide N-(2,4-dimethoxybenzyl)-1-methyl-3-(3-(pyridin-4-yl)-5-(trifluoromethyl)phenyl)-N-(1,2,4-thiadiazol-5-yl)-1H-indole-6-sulfonamide (0.050 g, 0.075 mmol) was dissolved in 0.5 mL of DCM and TFA (0.5 ml, 6.49 mmol) was added. The reaction was stirred for 15 minutes at room temperature. The reaction was concentrated, dissolved in acetonitrile, and passed through a PEAX ion exchange column (purchased from Biotage, LLC, Charlotte, N.C.). The column was flushed several times with acetonitrile, then the product was liberated by flushing several times with an 1M HCl solution in 15% MeOH/EtOAc. The solution was concentrated to afford 1-methyl-3-(3-(pyridin-4-yl)-5-(trifluoromethyl)phenyl)-N-(1,2,4-thiadiazol-5-yl)-1H-indole-6-sulfonamide (0.029 g, 0.056 mmol, 75% yield) as a yellow solid. $^1$H NMR (400 MHz, DMSO-$d_6$) δ=8.94-8.84 (m, 2 H), 8.46 (s, 1 H), 8.41 (s, 1 H), 8.32 (s, 1 H), 8.30 (d, J=6.1 Hz, 2 H), 8.14-8.09 (m, 3 H), 8.05 (d, J=1.3 Hz, 1 H), 7.62 (dd, J=1.6, 8.6 Hz, 1 H), 3.98 (s, 3 H). m/z (ESI). 516.0 (M+H)$^+$.

Example 16

3-(2-Cyano-4-(Trifluoromethyl)Phenyl)-1-Methyl-N-(1,2,4-Thiadiazol-5-yl)-1H-Indole-6-Sulfonamide

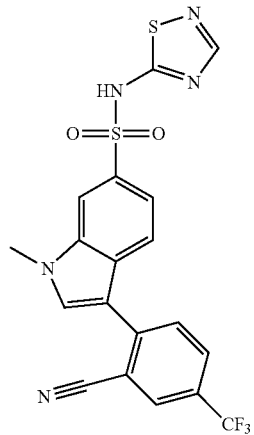 [SMILES: Cn1cc(-c2ccc(C(F)(F)F)cc2C#N)c2ccc(S(=O)(=O)Nc3ncns3)cc21]

A vial was charged with N-(2,4-dimethoxybenzyl)-1-methyl-3-(4,4,5,5-tetramethyl-1,3,2-dioxaborolan-2-yl)-N-(1,2,4-thiadiazol-5-yl)-1H-indole-6-sulfonamide (0.075 g, 0.131 mmol), 2-bromo-5-(trifluoromethyl)benzonitrile (0.082 g, 0.329 mmol). potassium phosphate (0.098 g, 0.460 mmol), and PdCl$_2$(dppf)-CH$_2$Cl$_2$ (10.74 mg, 0.013 mmol). DMF (0.876 ml) was added, and the vial was flushed with Ar, sealed, and heated to 85° C. for two hours. The reaction was diluted with ethyl acetate and washed with water. The aqueous layer was extracted with ethyl acetate, and the combined organic layers were washed with brine, dried with sodium sulfate, filtered and concentrated. The material was purified via column chromatography (0 to 100% EtOAc/Heptane) to give 3-(2-cyano-4-(trifluoromethyl)phenyl)-N-(2,4-dimethoxybenzyl)-1-methyl-N-(1,2,4-thiadiazol-5-yl)-1H-indole-6-sulfonamide as a light yellow solid. The solid was dissolved in DCM (0.5 ml) and TFA (0.5 ml, 6.49 mmol), and the resulting mixture was stirred for 15 min. The mixture was concentrated in vacuo. The residue was dissolved in acetonitrile, and passed through a PEAX ion exchange column. The column was flushed several times with acetonitrile, then the product was liberated by flushing several times with an 1M HCl solution in 15% MeOH/EtOAc. The solution was concentrated to afford 3-(2-cyano-4-(trifluoromethyl)phenyl)-1-methyl-N-(1,2,4-thiadiazol-5-yl)-1H-indole-6-sulfonamide (0.022 g, 0.047 mmol, 36.1% yield) as a pink solid. $^1$H NMR (400 MHz, DMSO-d$_6$) δ=8.44 (s, 1 H), 8.42 (s, 1 H), 8.17 (s, 1 H), 8.14-8.10 (m, 1 H), 8.07 (d, J=1.2 Hz, 1 H), 7.95 (d, J=8.1 Hz, 1 H), 7.83 (d, J=8.5 Hz, 1 H), 7.60 (dd, J=1.6, 8.5 Hz, 1 H), 4.01 (s, 3 H). m/z (ESI) 464.0 (M+H)$^+$.

Example 17

3-(3-Bromo-5-(Trifluoromethyl)Phenyl)-1-Methyl-N-(1,2,4-Thiadiazol-5-yl)-1H-Indole-6-Sulfonamide

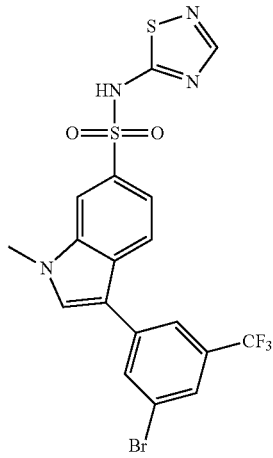 [SMILES: Cn1cc(-c2cc(Br)cc(C(F)(F)F)c2)c2ccc(S(=O)(=O)Nc3ncns3)cc21]

The title compound was prepared in an analogous manner to that described in Example 16 using 1,3-dibromo-5-(trifluoromethyl)benzene. The desired product, 3-(3-bromo-5-(trifluoromethyl)phenyl)-1-methyl-N-(1,2,4-thiadiazol-5-yl)-1H-indole-6-sulfonamide, was isolated as a purple solid. $^1$H NMR (400 MHz, DMSO-d$_6$) δ=8.44 (s, 8 H), 8.26 (s, 1 H), 8.14 (s, 1 H), 8.03-7.99 (m, J=5.3 Hz, 2 H), 7.96 (s, 1 H), 7.82 (s, 1 H), 7.66-7.57 (m, 1 H), 3.95 (s, 3 H). m/z (ESI) 517.0 (M+H)$^+$.

Example 18

1-Methyl-3-(2-(Pyridin-4-yl)-4-(Trifluoromethyl)Phenyl)-N-(1,2,4-Thiadiazol-5-yl)-1H-Indole-6-Sulfonamide

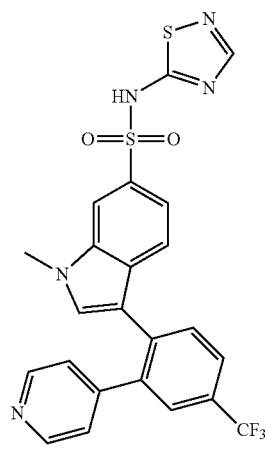 [SMILES: Cn1cc(-c2ccc(C(F)(F)F)cc2-c2ccncc2)c2ccc(S(=O)(=O)Nc3ncns3)cc21]

A microwave vial was charged with 3-(2-bromo-4-(trifluoromethyl)phenyl)-N-(2,4-dimethoxybenzyl)-1-methyl-N-(1,2,4-thiadiazol-5-yl)-1H-indole-6-sulfonamide (0.050 g, 0.075 mmol), pyridin-4-ylboronic acid (0.018 g, 0.150 mmol), potassium phosphate (0.056 g, 0.262 mmol), and Pd(AmPhos)$_2$Cl$_2$ (5.30 mg, 7.49 μmol). The vial was flushed with Ar, then 1,4-dioxane (0.375 ml) and water (0.125 ml) were added in sequence. The vial was sealed and microwaved at 100° C. for 30 minutes. The reaction was diluted with ethyl acetate and washed with water. The aqueous layer was extracted with ethyl acetate, and the combined organic layers were washed with brine, dried with sodium sulfate, filtered and concentrated. The material was purified via column chromatography (Redi-Sep Gold (Teledyne Isco, Lincoln, Nebr.) 12-g, gradient elution 0 to 100% EtOAc/Heptane) to afford N-(2,4-dimethoxybenzyl)-1-methyl-3-(2-(pyridin-4-yl)-4-(trifluoromethyl)phenyl)-N-(1,2,4-thiadiazol-5-yl)-1H-indole-6-sulfonamide as a yellow solid. The solid was dissolved in DCM (0.5 ml) and TFA (0.5 ml, 6.49 mmol), and the resulting mixture was stirred for 15 min. The mixture was concentrated in vacuo. The residue was dissolved in acetonitrile, and passed through a PEAX ion exchange column. The column was flushed several times with acetonitrile, then the product was liberated by flushing several times with an 1M HCl solution in 15% MeOH/EtOAc. The solution was concentrated to afford 1-methyl-3-(2-(pyridin-4-yl)-4-(trifluoromethyl)phenyl)-N-(1,2,4-thiadiazol-5-yl)-1H-indole-6-sulfonamide as a yellow solid. $^1$H NMR (400 MHz, DMSO-d$_6$) δ=8.55 (d, J=6.1 Hz, 2 H), 8.44 (s, 1 H), 7.97-7.90 (m, 2 H), 7.87 (s, 1 H), 7.80 (d, J=8.0 Hz, 1 H), 7.56-7.49 (m, 3 H), 7.34 (d, J=1.5 Hz, 2 H), 3.85 (s, 3 H). m/z (ESI) 516.0 (M+H)$^+$.

Example 19

3-(2-(1-(Azetidin-3-yl)-1H-Pyrazol-3-yl)-4-(Trifluoromethyl)Phenyl)-1-Methyl-N-(1,2,4-Thiadiazol-5-yl)-1H-Indole-6-Sulfonamide Hydrochloride

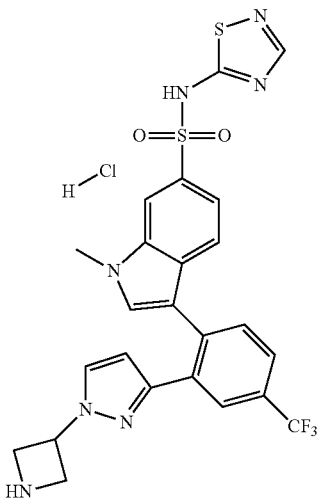

The title compound was prepared in an analogous manner to that described in Example 18 using tert-butyl 3-(3-(4,4,5,5-tetramethyl-1,3,2-dioxaborolan-2-yl)-1H-pyrazol-1-yl)azetidine-1-carboxylate as the coupling partner to afford 3-(2-(1-(azetidin-3-yl)-1H-pyrazol-3-yl)-4-(trifluoromethyl)phenyl)-1-methyl-N-(1,2,4-thiadiazol-5-yl)-1H-indole-6-sulfonamide hydrochloride as a light pink solid. $^1$H NMR (400 MHz, DMSO-$d_6$) δ=9.16-8.87 (m, 2 H), 8.43 (s, 1 H), 7.96 (d, J=1.1 Hz, 1 H), 7.83 (d, J=0.7 Hz, 2 H), 7.70 (s, 1 H), 7.68 (d, J=1.5 Hz, 1 H), 7.64-7.58 (m, 1 H), 7.38 (s, 1 H), 7.32 (dd, J=1.7, 8.5 Hz, 1 H), 7.14 (d, J=8.6 Hz, 1 H), 5.22 (quin, J=7.6 Hz, 1 H), 4.31-4.20 (m, 2 H), 4.17-4.07 (m, 2 H), 3.93 (s, 3 H) m/z (ESI) 560.2 (M+H)$^+$.

Example 20

1-Methyl-3-(2-(1-Methyl-1H-Pyrazol-5-yl)-4-(Trifluoromethyl)Phenyl)-N-(5-Methyl-4-(Trifluoromethyl)Thiazol-2-yl)-1H-Indole-6-Sulfonamide

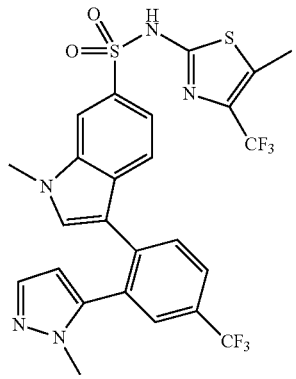

A flask was charged with perfluorophenyl 1-methyl-3-(2-(1-methyl-1H-pyrazol-5-yl)-4-(trifluoromethyl)-phenyl)-1H-indole-6-sulfonate (INTERMEDIATE E) (44.48 mg, 0.074 mmol), 5-methyl-4-(trifluoromethyl)thiazol-2-amine (17.51 mg, 0.096 mmol) and THF (0.5 mL). The flask was cooled in an ice bath for 5 min, then lithium bis(trimethylsilyl)amide (1M in THF) (185 µl, 0.185 mmol) was added dropwise to give an orange solution. The mixture was stirred for 1 h, then an additional portion of the base solution (0.08 mL) was added. After 20 min, the cooling bath was removed. The mixture was stirred for an additional 20 min, then an additional portion of 5-methyl-4-(trifluoromethyl)thiazol-2-amine (10 mg) was added. The mixture was stirred for 20 min, then was quenched with AcOH (0.1 mL) and concentrated from MeOH/DCM. The crude product was purified by chromatography on silica gel (0 to 5% MeOH/DCM) to give 1-methyl-3-(2-(1-methyl-1H-pyrazol-5-yl)-4-(trifluoromethyl)phenyl)-N-(5-methyl-4-(trifluoromethyl)thiazol-2-yl)-1H-indole-6-sulfonamide (12.27 mg, 0.020 mmol, 27.7% yield) as a tan solid. $^1$H NMR (400 MHz, DMSO-$d_6$) δ=8.01 (d, J=1.5 Hz, 1 H), 7.94-7.82 (m, 2 H), 7.77 (d, J=0.9 Hz, 1 H), 7.61 (d, J=8.5 Hz, 1 H), 7.50 (dd, J=1.7, 8.5 Hz, 1 H), 7.37 (d, J=1.9 Hz, 1 H), 7.24 (s, 1 H), 6.34 (d, J=1.9 Hz, 1 H), 3.82 (s, 3 H), 3.24 (s, 3 H), 2.40-2.35 (m, 3 H). m/z (ESI) 600.2 (M+H)$^+$.

Example 21

3-(2-(1H-Pyrazol-4-yl)-4-(Trifluoromethyl)Phenyl)-1-Methyl-N-(1,2,4-Thiadiazol-5-yl)-1H-Indole-6-Sulfonamide

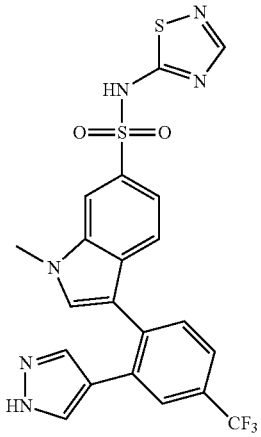 [SMILES: Cn1cc(-c2ccc(C(F)(F)F)cc2-c2cn[nH]c2)c2ccc(S(=O)(=O)Nc3ncns3)cc21]

The title compound was prepared in an analogous manner to that described in Example 18 using tert-butyl 4-(4,4,5,5-tetramethyl-1,3,2-dioxaborolan-2-yl)-1H-pyrazole-1-carboxylate as the coupling partner to afford 3-(2-(1H-pyrazol-4-yl)-4-(trifluoromethyl)phenyl)-1-methyl-N-(1,2,4-thiadiazol-5-yl)-1H-indole-6-sulfonamide as a pink solid. $^1$H NMR (400 MHz, DMSO-$d_6$) δ=8.43 (s, 1 H), 7.95 (d, J=1.2 Hz, 1 H), 7.85 (d, J=1.4 Hz, 1 H), 7.68 (s, 1 H), 7.66-7.61 (m, 1 H), 7.58-7.53 (m, 1 H), 7.42 (s, 2 H), 7.31 (dd, J=1.6, 8.5 Hz, 1 H), 7.14 (d, J=8.4 Hz, 1 H), 3.93 (s, 3 H). m/z (ESI) 505.1 (M+H)$^+$.

Example 22

1-Methyl-3-(2-(1,2,3,6-Tetrahydropyridin-4-yl)-4-(Trifluoromethyl)Phenyl)-N-(1,2,4-Thiadiazol-5-yl)-1H-Indole-6-Sulfonamide

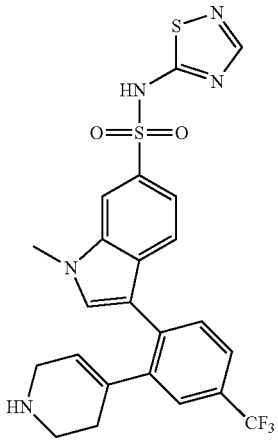 [SMILES: Cn1cc(-c2ccc(C(F)(F)F)cc2C2=CCNCC2)c2ccc(S(=O)(=O)Nc3ncns3)cc21]

The title compound was prepared in an analogous manner to that described in Example 18 using tert-butyl 4-(4,4,5,5-tetramethyl-1,3,2-dioxaborolan-2-yl)-5,6-dihydropyridine-1(2H)-carboxylate as coupling partner. Additionally, after passing the material through the ion exchange column the solution was concentrated and purified via column chromatography (silica gel, gradient elution 0 to 10% MeOH/DCM) to afford 1-methyl-3-(2-(1,2,3,6-tetrahydropyridin-4-yl)-4-(trifluoromethyl)phenyl)-N-(1,2,4-thiadiazol-5-yl)-1H-indole-6-sulfonamide as a white solid. $^1$H NMR (400 MHz, DMSO-d$_6$) δ=8.73 (br. s., 2 H), 8.33 (s, 1 H), 8.00 (d, J=1.3 Hz, 1 H), 7.81-7.76 (m, 1 H), 7.75-7.68 (m, 3 H), 7.55 (dt, J=1.6, 4.2 Hz, 2 H), 5.89 (s, 1 H), 3.96 (s, 3 H), 3.71 (br. s., 2 H), 2.98 (br. s., 2 H), 2.12 (br. s., 2 H). m/z (ESI) 520.1 (M+H)$^+$.

Example 23

3-(2-Chloro-4-(Trifluoromethyl)Phenyl)-1-Methyl-N-(1,2,4-Thiadiazol-5-yl)-1H-Indole-6-Sulfonamide

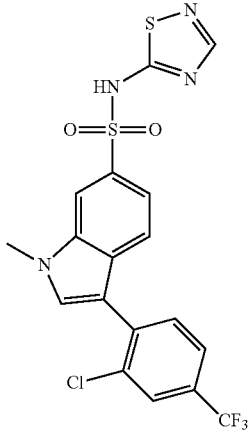 [SMILES: Cn1cc(-c2ccc(C(F)(F)F)cc2Cl)c2ccc(S(=O)(=O)Nc3ncns3)cc21]

Step 1: 3-(2-Chloro-4-(Trifluoromethyl)Phenyl)-N-(2,4-Dimethoxybenzyl)-1-Methyl-N-(1,2,4-Thiadiazol-5-yl)-1H-Indole-6-Sulfonamide A vial was charged with N-(2,4-dimethoxybenzyl)-1-methyl-3-(4,4,5,5-tetramethyl-1,3,2-dioxaborolan-2-yl)-N-(1,2,4-thiadiazol-5-yl)-1H-indole-6-sulfonamide (0.500 g, 0.876 mmol), potassium phosphate (0.651 g, 3.07 mmol), and bis(tri-t-butylphosphine)palladium(0) (0.045 g, 0.088 mmol). The vial was flushed with Ar, then 1,4-dioxane (6.57 ml) and water (2.191 ml) were added in sequence, followed by 2-chloro-1-iodo-4-(trifluoromethyl)benzene (0.426 ml, 2.63 mmol). The vial was sealed and stirred at room temperature for two hours. The reaction was diluted with ethyl acetate and washed with water. The aqueous layer was extracted with ethyl acetate, and the combined organic layers were washed with brine, dried with sodium sulfate, filtered and concentrated. The material was purified via column chromatography (RediSep Gold (Teledyne Isco, Lincoln, Nebr.) 40 g, gradient elution 0-100% EtOAc/Heptane) to afford 3-(2-chloro-4-(trifluoromethyl)phenyl)-N-(2,4-dimethoxybenzyl)-1-methyl-N-(1,2,4-thiadiazol-5-yl)-1H-indole-6-sulfonamide (0.405 g, 0.650 mmol, 74.2% yield) as a light yellow solid. m/z (ESI) 624.0 (M+H)$^+$.

Step 2: 3-(2-Chloro-4-(Trifluoromethyl)Phenyl)-1-Methyl-N-(1,2,4-Thiadiazol-5-yl)-1H-Indole-6-Sulfonamide 3-(2-chloro-4-(trifluoromethyl)phenyl)-N-(2,4-dimethoxybenzyl)-1-methyl-N-(1,2,4-thiadiazol-5-yl)-1H-indole-6-sulfonamide (0.020 g, 0.032 mmol) was dissolved in 0.5 mL of DCM, and TFA (0.5 ml, 6.49 mmol) was added. The reaction was stirred for 15 minutes. The reaction was concentrated, dissolved in acetonitrile, and passed through a PEAX ion exchange column. The column was flushed several times with acetonitrile, then the product was liberated by flushing several times with an 1M HCl solution in 15% MeOH/EtOAc. The solution was concentrated to afford 3-(2-chloro-4-(trifluoromethyl)phenyl)-1-methyl-N-(1,2,4-thiadiazol-5-yl)-1H-indole-6-sulfonamide (0.016 g) as a tan solid. (M+H)$^+$. $^1$H NMR (400 MHz, DMSO-d$_6$) δ=8.43 (s, 7 H), 8.03 (s, 1 H), 8.01-7.97 (m, 2 H), 7.79 (d, J=1.1 Hz, 2 H), 7.67 (d, J=8.6 Hz, 4 H), 7.55 (dd, J=1.7, 8.5 Hz, 1 H), 3.98 (s, 3 H). m/z (ESI) 473.1 (M+H)$^+$.

EXAMPLE 24

3-(3-Chloro-4-(Trifluoromethyl)Phenyl)-1-Methyl-N-(1,2,4-Thiadiazol-5-yl)-1H-Indole-6-Sulfonamide

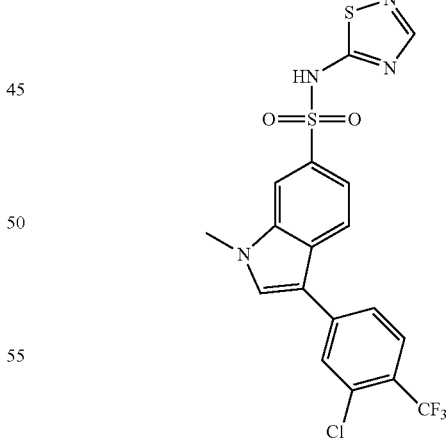

The title compound was prepared in an analogous manner to that described in Example 23 using 4-bromo-2-chloro-1-(trifluoromethyl)benzene as the coupling partner to afford 3-(3-chloro-4-(trifluoromethyl)phenyl)-1-methyl-N-(1,2,4-thiadiazol-5-yl)-1H-indole-6-sulfonamide as a pink solid. $^1$H NMR (400 MHz, DMSO-d$_6$) δ=8.43 (s, 1 H), 8.27 (s, 1 H), 8.09 (dd, J=0.4, 8.7 Hz, 1 H), 8.02 (d, J=1.2 Hz, 1 H), 7.97 (s, 1 H), 7.91-7.84 (m, 2 H), 7.61 (dd, J=1.7, 8.5 Hz, 1 H), 3.96 (s, 3 H). m/z (ESI) 472.0 (M+H)$^+$.

Example 25

3-(2-(1-Methyl-1H-Pyrazol-5-yl)-4-(Trifluoromethyl)Phenyl)-N-(1,2,4-Thiadiazol-5-yl)-1H-Pyrrolo[2,3-B]Pyridine-6-Sulfonamide

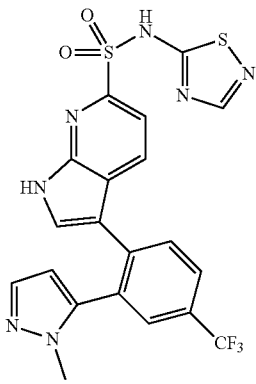 [SMILES: Cn1nccc1-c1cc(C(F)(F)F)ccc1-c1c[nH]c2nc(S(=O)(=O)Nc3ncns3)ccc12]

A vial was charged with N-(2,4-dimethoxybenzyl)-3-(2-(1-methyl-1H-pyrazol-5-yl)-4-(trifluoromethyl)phenyl)-N-(1,2,4-thiadiazol-5-yl)-1H-pyrrolo[2,3-b]pyridine-6-sulfonamide (Intermediate J) (46.47 mg, 0.071 mmol) and DCM (0.5 mL) to give a clear solution. TFA (0.1 mL) was added dropwise, and the resulting mixture was stirred for 30 min. The mixture was diluted with methanol, then filtered through Celite® (diatomaceous earth). The filtrate was concentrated, and the residue was triturated with diethyl ether to give a white solid. The diethyl ether was decanted, and the solid was put under vacuum again for 10 min. Diethyl ether was added, and the suspension was sonicated for 1 min to give a fine white precipitate. The mixture was filtered on a membrane filter, and the collected solid was washed with diethyl ether (3×), then dried under a stream of $N_2$ to give 3-(2-(1-methyl-1H-pyrazol-5-yl)-4-(trifluoromethyl)phenyl)-N-(1,2,4-thiadiazol-5-yl)-1H-pyrrolo[2,3-b]pyridine-6-sulfonamide (18.02 mg, 0.036 mmol, 50.3% yield) as a white solid. $^1$H NMR (400 MHz, DMSO-$d_6$) δ=12.49 (d, J=2.4 Hz, 1 H), 8.45 (s, 1 H), 8.01 (s, 1 H), 7.94-7.88 (m, 2 H), 7.79 (s, 1 H), 7.65 (d, J=8.3 Hz, 1 H), 7.40 (s, 1 H), 7.35 (d, J=2.7 Hz, 1 H), 6.37 (d, J=1.9 Hz, 1 H), 3.23 (s, 3 H). m/z (ESI) 506.0 (M+H)$^+$.

Example 26

1-Methyl-3-(2-(1-Methyl-1H-Pyrazol-5-yl)-4-(Trifluoromethyl)Phenyl)-N-(1,2,4-Thiadiazol-5-yl)-1H-Pyrrolo[2,3-B]Pyridine-6-Sulfonamide

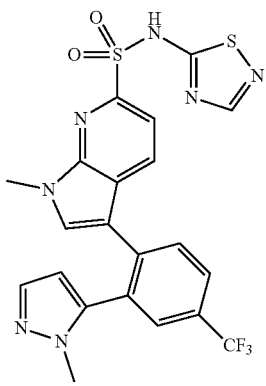 [SMILES: Cn1nccc1-c1cc(C(F)(F)F)ccc1-c1cn(C)c2nc(S(=O)(=O)Nc3ncns3)ccc12]

A vial was charged with N-(2,4-dimethoxybenzyl)-3-(2-(1-methyl-1H-pyrazol-5-yl)-4-(trifluoromethyl)phenyl)-N-(1,2,4-thiadiazol-5-yl)-1H-pyrrolo[2,3-b]pyridine-6-sulfonamide (Intermediate J) (77.2 mg, 0.118 mmol) and DMF (1 mL) to give a clear solution. Sodium hydride (60% in mineral oil) (7.06 mg, 0.177 mmol) was added in one portion to give a bright yellow mixture. The mixture was stirred for 45 min, then iodomethane (14.72 μl, 0.235 mmol) was added. After stirring for an additional 1 h, the mixture was diluted with water and extracted with EtOAc (2×). The combined organic extracts were dried over sodium sulfate, filtered, and concentrated. The residue was taken up in DCM (0.9 mL) and TFA (0.18 mL), and the resulting mixture was stirred for 1.5 h. The mixture was diluted with MeOH (5 mL), then filtered through Celite® (diatomaceous earth) with the aid of methanol. The filtrate was concentrated, and the crude product was purified by chromatography on silica gel (0 to 10% MeOH/DCM) to afford 1-methyl-3-(2-(1-methyl-1H-pyrazol-5-yl)-4-(trifluoromethyl)phenyl)-N-(1,2,4-thiadiazol-5-yl)-1H-pyrrolo[2,3-b]pyridine-6-sulfonamide (51.42 mg, 0.099 mmol, 84% yield) as a white foam. $^1$H NMR (400 MHz, DMSO-$d_6$) δ=8.48 (s, 1 H), 7.97-7.85 (m, 3 H), 7.83-7.78 (m, 1 H), 7.61 (d, J=8.3 Hz, 1 H), 7.53 (s, 1 H), 7.38 (d, J=1.9 Hz, 1 H), 6.35 (d, J=1.9 Hz, 1 H), 3.75 (s, 3 H), 3.28 (s, 3 H). m/z (ESI) 520.1 (M+H)$^+$.

Example 27

1-Acetyl-3-(2-(1-Methyl-1H-Pyrazol-5-yl)-4-(Trifluoromethyl)Phenyl)-N-(1,2,4-Thiadiazol-5-yl)-1H-Pyrrolo [2,3-B]Pyridine-6-Sulfonamide

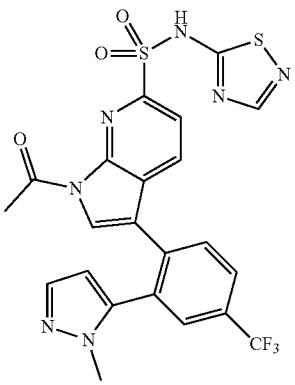 [SMILES: CC(=O)n1cc(-c2ccc(C(F)(F)F)cc2-c2ccnn2C)c2ccc(S(=O)(=O)Nc3ncns3)nc21]

The title compound was prepared in an analogous manner to that described in Example 26, except that acetic anhydride was used in place of iodomethane, and the desired product 1-acetyl-3-(2-(1-methyl-1h-pyrazol-5-yl)-4-(trifluoromethyl)phenyl)-n-(1,2,4-thiadiazol-5-yl)-1h-pyrrolo[2,3-b]pyridine-6-sulfonamide, was isolated as a white foam. $^1$H NMR (400 MHz, DMSO-$d_6$) δ=8.51 (s, 1 H), 8.02 (s, 1 H), 8.01-7.86 (m, 4 H), 7.79 (d, J=8.2 Hz, 1 H), 7.35 (d, J=1.9 Hz, 1 H), 6.35 (d, J=1.9 Hz, 1 H), 3.40 (s, 3 H), 2.75 (s, 3 H). m/z (ESI) 548.0 (M+H)$^+$.

Example 28

3-(4-FLUORO-2-METHOXYPHENYL)-1-METHYL-N-(1,2,4-Thiadiazol-5-yl)-1H-Indole-6-Sulfonamide

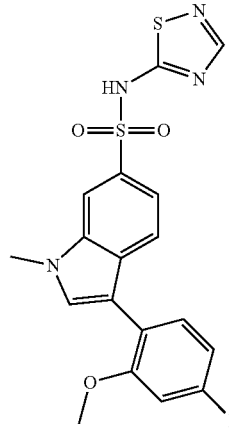

To a vial containing 4-fluoro-2-methoxyphenylboronic acid (0.075 g, 0.450 mmol) was added a solution of 3-bromo-N-(2,4-dimethoxybenzyl)-1-methyl-N-(1,2,4-thiadiazol-5-yl)-1H-indole-6-sulfonamide (Intermediate D) (0.100 g, 0.191 mmol) and Pd(AmPhos)$_2$Cl$_2$ (0.014 g, 0.019 mmol) in 1 mL of dioxane. A solution of tripotassium phosphate (0.142 g, 0.669 mmol) in 318 µL of water was added, and the vial was sealed and placed in a heated shaker block. The vial was shaken for 2 hours at 100° C. The vial was uncapped and the reaction was concentrated. The resulting solid was dissolved in a solution of trifluoroacetic acid (0.293 mL, 3.82 mmol) in 1 mL of dichloromethane. The reaction was shaken at room temperature for 1 hour. The solution was filtered and the solids were washed with DCM and methanol. The filtrate was concentrated and purified via reverse phase HPLC (8 min gradient elution 15 to 75% ACN/H$_2$O, 0.1% TFA modifier) to afford 3-(4-fluoro-2-methoxyphenyl)-1-methyl-N-(1,2,4-thiadiazol-5-yl)-1H-indole-6-sulfonamide as an off-white solid. $^1$H NMR (500 MHz, DMSO-d$_6$) δ ppm 3.79 (s, 3 H) 3.87 (s, 3 H) 6.83 (td, J=8.42, 2.52 Hz, 1 H) 7.01 (d, J=2.52 Hz, 1 H) 6.99 (d, J=2.52 Hz, 1 H) 7.43-7.48 (m, 2 H) 7.56 (d, J=8.48 Hz, 1 H) 7.65 (s, 1 H) 7.84-7.90 (m, 2 H). m/z (ESI) 418.1 (M+H)$^+$.

Example 29

3-(3,5-Dimethoxyphenyl)-1-Methyl-N-(1,2,4-Thiadiazol-5-yl)-1H-Indole-6-Sulfonamide

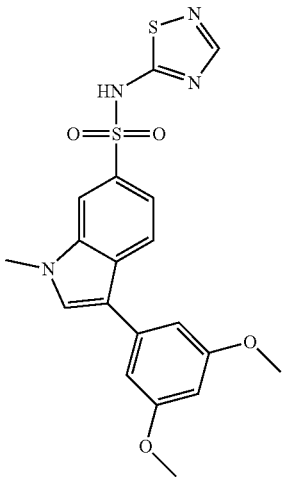

The title compound was prepared in an analogous manner to that described in Example 28 using (3,5-dimethoxyphenyl)boronic acid and 3-bromo-N-(2,4-dimethoxybenzyl)-1-methyl-N-(1,2,4-thiadiazol-5-yl)-1H-indole-6-sulfonamide, and the desired product, 3-(3,5-dimethoxyphenyl)-1-methyl-N-(1,2,4-thiadiazol-5-yl)-1H-indole-6-sulfonamide, was isolated as an off-white solid. $^1$H NMR (500 MHz, DMSO-d$_6$) δ ppm 3.78-3.88 (m, 9 H) 6.39 (t, J=2.23 Hz, 1 H) 6.77 (d, J=2.29 Hz, 2 H) 7.52 (dd, J=8.42, 1.55 Hz, 1 H) 7.75-7.89 (m, 4 H). m/z (ESI) 430.1 (M+H)$^+$.

Example 30

3-(3-Cyano-4-Fluorophenyl)-1-Methyl-N-(1,2,4-Thiadiazol-5-yl)-1H-Indole-6-Sulfonamide

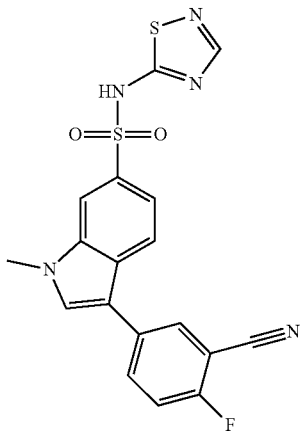 [SMILES: Cn1cc(-c2ccc(F)c(C#N)c2)c2ccc(S(=O)(=O)Nc3ncns3)cc21]

The title compound was prepared in an analogous manner to that described in Example 28 using (3-cyano-4-fluorophenyl)boronic acid and 3-bromo-N-(2,4-dimethoxybenzyl)-1-methyl-N-(1,2,4-thiadiazol-5-yl)-1H-indole-6-sulfonamide, and the desired product, 3-(3-cyano-4-fluorophenyl)-1-methyl-N-(1,2,4-thiadiazol-5-yl)-1H-indole-6-sulfonamide, was isolated as an off-white solid. $^1$H NMR (500 MHz, DMSO-d$_6$) δ ppm 3.90 (s, 3 H) 7.54-7.60 (m, 2 H) 7.91-8.07 (m, 5 H) 8.13 (dd, J=6.13, 2.35 Hz, 1H). m/z (ESI) 413.0 (M+H)$^+$.

Example 31

3-(4-Cyano-3-Fluorophenyl)-1-Methyl-N-(1,2,4-Thiadiazol-5-yl)-1H-Indole-6-Sulfonamide

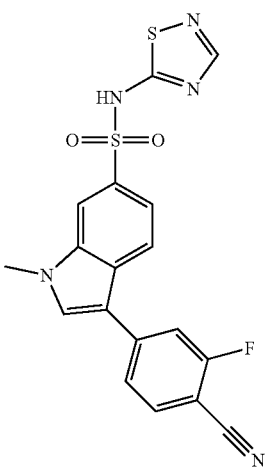 [SMILES: Cn1cc(-c2ccc(C#N)c(F)c2)c2ccc(S(=O)(=O)Nc3ncns3)cc21]

The title compound was prepared in an analogous manner to that described in Example 28 using (4-cyano-3-fluorophenyl)boronic acid and 3-bromo-N-(2,4-dimethoxybenzyl)-1-methyl-N-(1,2,4-thiadiazol-5-yl)-1H-indole-6-sulfonamide, and the desired product, 3-(4-cyano-3-fluorophenyl)-1-methyl-N-(1,2,4-thiadiazol-5-yl)-1H-indole-6-sulfonamide, was isolated as an off-white solid. $^1$H NMR (500 MHz, DMSO-d$_6$) δ ppm 3.92 (s, 3 H) 7.60 (dd, J=8.53, 1.55 Hz, 1 H) 7.73-7.80 (m, 2 H) 7.87-7.97 (m, 2 H) 8.02-8.10 (m, 2 H) 8.23 (s, 1 H). m/z (ESI) 413.0 (M+H)$^+$.

Example 32

1-Methyl-N-(1,2,4-Thiadiazol-5-yl)-3-(4-(Trifluoromethoxy)Phenyl)-1H-Indole-6-Sulfonamide

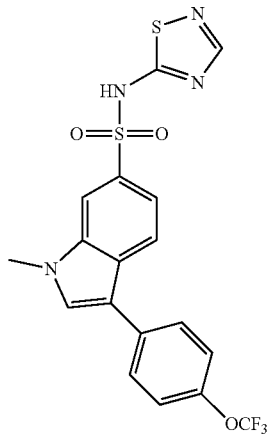 [SMILES: Cn1cc(-c2ccc(OC(F)(F)F)cc2)c2ccc(S(=O)(=O)Nc3ncns3)cc21]

The title compound was prepared in an analogous manner to that described in Example 28 using (4-(trifluoromethoxy)phenyl)boronic acid and 3-bromo-N-(2,4-dimethoxybenzyl)-1-methyl-N-(1,2,4-thiadiazol-5-yl)-1H-indole-6-sulfonamide, and the desired product, 1-methyl-N-(1,2,4-thiadiazol-5-yl)-3-(4-(trifluoromethoxy)phenyl)-1H-indole-6-sulfonamide, was isolated as an off-white solid. $^1$H NMR (500 MHz, DMSO-d$_6$) δ ppm 3.90 (s, 3 H) 7.41 (m, J=8.13 Hz, 2 H) 7.52-7.58 (m, 1 H) 7.74-7.79 (m, 2 H) 7.88-8.00 (m, 4 H). m/z (ESI) 454.0 (M+H)$^+$.

Example 33

1-Methyl-N-(1,2,4-Thiadiazol-5-yl)-3-(3-(Trifluoromethoxy)Phenyl)-1H-Indole-6-Sulfonamide

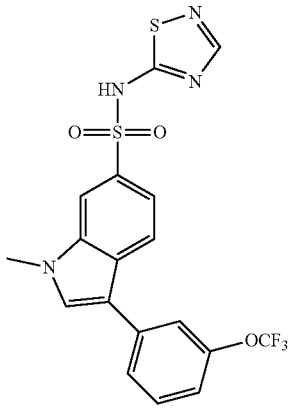 [SMILES: Cn1cc(-c2cccc(OC(F)(F)F)c2)c2ccc(S(=O)(=O)Nc3ncns3)cc21]

The title compound was prepared in an analogous manner to that described in Example 28 using (3-(trifluoromethoxy)phenyl)boronic acid and 3-bromo-N-(2,4-dimethoxybenzyl)-1-methyl-N-(1,2,4-thiadiazol-5-yl)-1H-indole-6-sulfonamide, and the desired product, 1-methyl-N-(1,2,4-thiadiazol-5-yl)-3-(3-(trifluoromethoxy)phenyl)-1H-indole-6-sulfonamide, was isolated as an off-white solid. $^1$H NMR (500 MHz, DMSO-d$_6$) δ ppm 3.89 (s, 3 H) 7.22 (d, J=8.25 Hz, 1 H) 7.54-7.58 (m, 3 H) 7.71 (d, J=8.02 Hz, 1 H) 7.87-7.92 (m, 3 H) 7.98 (s, 1 H). m/z (ESI) 454.0 (M+H)$^+$.

Example 34

3-(3-Cyanophenyl)-1-Methyl-N-(1,2,4-Thiadiazol-5-yl)-1H-Indole-6-Sulfonamide

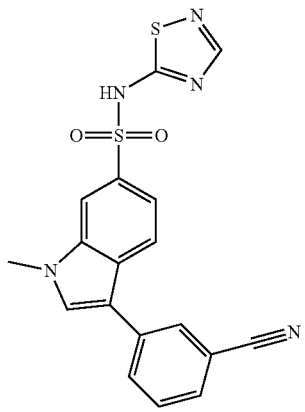 [SMILES: Cn1cc(-c2cccc(C#N)c2)c2ccc(S(=O)(=O)Nc3ncns3)cc21]

The title compound was prepared in an analogous manner to that described in Example 28 using (3-cyanophenyl)boronic acid and 3-bromo-N-(2,4-dimethoxybenzyl)-1-methyl-N-(1,2,4-thiadiazol-5-yl)-1H-indole-6-sulfonamide, and the desired product, 3-(3-cyanophenyl)-1-methyl-N-(1,2,4-thiadiazol-5-yl)-1H-indole-6-sulfonamide, was isolated as an off-white solid. $^1$H NMR (500 MHz, DMSO-d$_6$) δ ppm 3.90 (s, 3 H) 7.56 (dd, J=8.48, 1.60 Hz, 1 H) 7.61-7.69 (m, 2 H) 7.86-7.92 (m, 2 H) 7.94-8.07 (m, 4 H). m/z (ESI) 395.1 (M+H)$^+$.

Example 35

1-Methyl-3-Phenyl-N-(1,2,4-Thiadiazol-5-yl)-1H-Indole-6-Sulfonamide

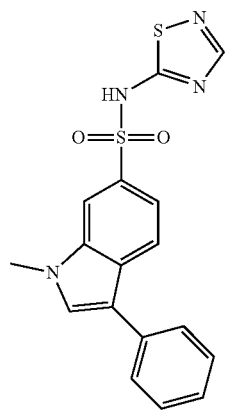 [SMILES: Cn1cc(-c2ccccc2)c2ccc(S(=O)(=O)Nc3ncns3)cc21]

The title compound was prepared in an analogous manner to that described in Example 28 using phenylboronic acid and 3-bromo-N-(2,4-dimethoxybenzyl)-1-methyl-N-(1,2,4-thiadiazol-5-yl)-1H-indole-6-sulfonamide, and the desired product, 1-methyl-3-phenyl-N-(1,2,4-thiadiazol-5-yl)-1H-indole-6-sulfonamide, was isolated as an off-white solid. $^1$H NMR (500 MHz, DMSO-d$_6$) δ ppm 3.88 (s, 3 H) 7.15-7.30

(m, 1 H) 7.43 (t, J=7.73 Hz, 2 H) 7.48-7.55 (m, 1 H) 7.61-7.68 (m, 2 H) 7.81 (d, J=4.47 Hz, 2 H) 7.85-7.89 (m, 2 H). m/z (ESI) 370.1 (M+H)+.

Example 36

3-(2,4-Dimethoxyphenyl)-1-Methyl-N-(1,2,4-Thiadiazol-5-yl)-1H-Indole-6-Sulfonamide

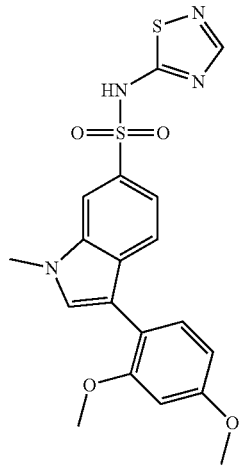 [SMILES: COc1ccc(-c2cn(C)c3cc(S(=O)(=O)Nc4ncns4)ccc23)c(OC)c1]

The title compound was prepared in an analogous manner to that described in Example 28 using (2,4-dimethoxyphenyl)boronic acid and 3-bromo-N-(2,4-dimethoxybenzyl)-1-methyl-N-(1,2,4-thiadiazol-5-yl)-1H-indole-6-sulfonamide, and the desired product, 3-(2,4-dimethoxyphenyl)-1-methyl-N-(1,2,4-thiadiazol-5-yl)-1H-indole-6-sulfonamide, was isolated as an off-white solid. $^1$H NMR (500 MHz, DMSO-d$_6$) δ ppm 3.76 (s, 3H) 3.80 (s, 3H) 3.87 (s, 3H) 6.59-6.68 (m, 2 H) 7.35 (d, J=8.25 Hz, 1 H) 7.43 (dd, J=8.42, 1.43 Hz, 1 H) 7.52-7.60 (m, 1 H) 7.85 (s, 1 H) 7.94 (br. s., 1 H). m/z (ESI) 430.1 (M+H)+.

Example 37

1-Methyl-3-(Naphthalen-1-yl)-N-(1,2,4-Thiadiazol-5-yl)-1H-Indole-6-Sulfonamide

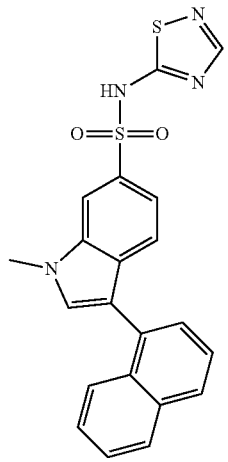 [SMILES: Cn1cc(-c2cccc3ccccc23)c2ccc(S(=O)(=O)Nc3ncns3)cc21]

The title compound was prepared in an analogous manner to that described in Example 28 using naphthalen-1-ylboronic acid and 3-bromo-N-(2,4-dimethoxybenzyl)-1-methyl-N-(1,2,4-thiadiazol-5-yl)-1H-indole-6-sulfonamide, and the desired product, 1-methyl-3-(naphthalen-1-yl)-N-(1,2,4-thiadiazol-5-yl)-1H-indole-6-sulfonamide, was isolated as an off-white solid. $^1$H NMR (500 MHz, DMSO-d$_6$) δ ppm 3.98 (s, 3 H) 7.37 (d, J=8.36 Hz, 1 H) 7.44-7.48 (m, 2 H) 7.51-7.62 (m, 3 H) 7.80 (s, 1 H) 7.93 (dd, J=8.19, 4.64 Hz, 2 H) 7.97-8.03 (m, 2 H) 8.08 (s, 1 H). m/z (ESI) 420.1 (M+H)+.

Example 38

1-Methyl-3-(Quinolin-5-yl)-N-(1,2,4-Thiadiazol-5-yl)-1H-Indole-6-Sulfonamide

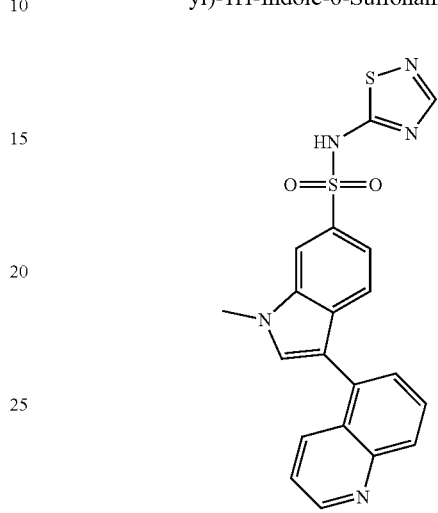

The title compound was prepared in an analogous manner to that described in Example 28 using quinolin-5-ylboronic acid and 3-bromo-N-(2,4-dimethoxybenzyl)-1-methyl-N-(1,2,4-thiadiazol-5-yl)-1H-indole-6-sulfonamide, and the desired product, 1-methyl-3-(quinolin-5-yl)-N-(1,2,4-thiadiazol-5-yl)-1H-indole-6-sulfonamide, was isolated as an off-white solid. $^1$H NMR (500 MHz, DMSO-d$_6$) δ ppm 3.99 (s, 3 H) 7.43-7.51 (m, 3 H) 7.64-7.68 (m, 1 H) 7.82-7.89 (m, 2 H) 8.01-8.05 (m, 2 H) 8.20 (s, 1 H) 8.33 (d, J=8.02 Hz, 1 H) 8.93 (dd, J=4.12, 1.60 Hz, 1 H). m/z (ESI) 421.1 (M+H)+.

Example 39

1-Methyl-3-(3-(Methylsulfonyl)Phenyl)-N-(1,2,4-Thiadiazol-5-yl)-1H-Indole-6-Sulfonamide

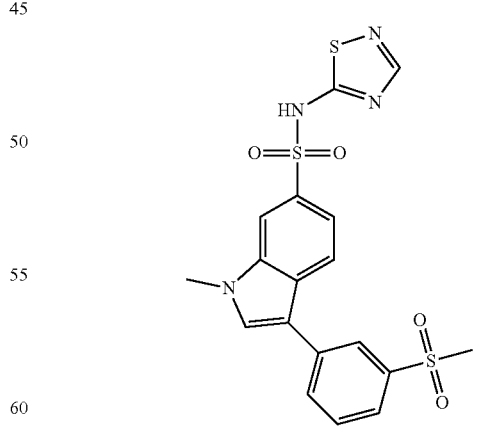

The title compound was prepared in an analogous manner to that described in Example 28 using (3-(methylsulfonyl)phenyl)boronic acid and 3-bromo-N-(2,4-dimethoxybenzyl)-1-methyl-N-(1,2,4-thiadiazol-5-yl)-1H-indole-6-sulfonamide, and the desired product, 1-methyl-3-(3-(methylsulfonyl)phenyl)-N-(1,2,4-thiadiazol-5-yl)-1H- indole-6-sulfonamide, was isolated as an off-white solid. $^1$H NMR (500 MHz, DMSO-d$_6$) δ ppm 3.91 (s, 3 H) 7.57 (dd, J=8.48, 1.49 Hz, 1 H) 7.71 (t, J=7.73 Hz, 1 H) 7.77 (d, J=8.02 Hz, 1 H) 7.84-7.95 (m, 3 H) 8.02 (d, J=7.90 Hz, 2 H) 8.05 (s, 1 H) 8.13 (s, 1 H). m/z (ESI) 448.0 (M+H)$^+$.

Example 40

3-(4-Methoxynaphthalen-1-yl)-1-Methyl-N-(1,2,4-Thiadiazol-5-yl)-1H-Indole-6-Sulfonamide

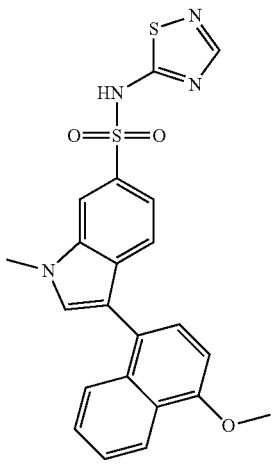

The title compound was prepared in an analogous manner to that described in Example 28 using (4-methoxynaphthalen-1-yl)boronic acid and 3-bromo-N-(2,4-dimethoxybenzyl)-1-methyl-N-(1,2,4-thiadiazol-5-yl)-1H-indole-6-sulfonamide, and the desired product, 3-(4-methoxynaphthalen-1-yl)-1-methyl-N-(1,2,4-thiadiazol-5-yl)-1H-indole-6-sulfonamide, was isolated as an off-white solid. $^1$H NMR (500 MHz, DMSO-d$_6$) δ ppm 3.96 (s, 3 H) 4.02 (s, 3 H) 7.06 (d, J=8.02 Hz, 1 H) 7.32 (d, J=8.36 Hz, 1 H) 7.37-7.48 (m, 3 H) 7.51 (d, J=8.25 Hz, 1 H) 7.72 (s, 1 H) 7.84 (d, J=8.59 Hz, 1 H) 7.97 (s, 1 H) 8.13 (s, 1 H) 8.24 (d, J=8.36 Hz, 1 H). m/z (ESI) 450.1 (M+H)$^+$.

Example 41

3-(2-Chloro-4-Methoxyphenyl)-1-Methyl-N-(1,2,4-Thiadiazol-5-yl)-1H-Indole-6-Sulfonamide

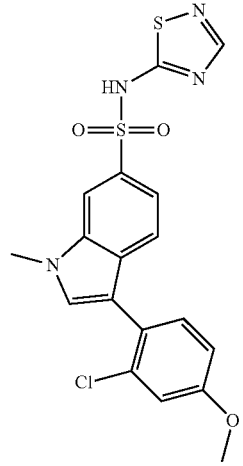 [SMILES: COc1ccc(-c2cn(C)c3cc(S(=O)(=O)Nc4ncns4)ccc23)c(Cl)c1]

The title compound was prepared in an analogous manner to that described in Example 28 using (2-chloro-4-methoxyphenyl)boronic acid and 3-bromo-N-(2,4-dimethoxybenzyl)-1-methyl-N-(1,2,4-thiadiazol-5-yl)-1H-indole-6-sulfonamide, and the desired product, 3-(2-chloro-4-methoxyphenyl)-1-methyl-N-(1,2,4-thiadiazol-5-yl)-1H-indole-6-sulfonamide, was isolated as an off-white solid. $^1$H NMR (500 MHz, DMSO-d$_6$) δ ppm 3.82 (s, 3 H) 3.92 (s, 3 H) 6.96-7.04 (m, 1 H) 7.17 (d, J=2.63 Hz, 1 H) 7.42 (d, J=8.59 Hz, 1 H) 7.45-7.53 (m, 2 H) 7.71 (s, 1 H) 7.93 (s, 1 H) 8.19 (s, 1 H). m/z (ESI) 434.0 (M+H)$^+$.

Example 42

3-(3,5-Dimethylisoxazol-4-yl)-1-Methyl-N-(1,2,4-Thiadiazol-5-yl)-1H-Indole-6-Sulfonamide

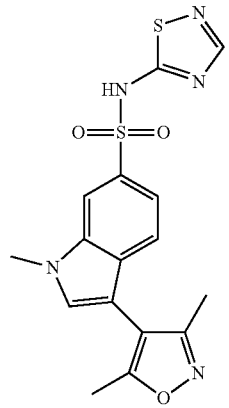 [SMILES: Cc1noc(C)c1-c1cn(C)c2cc(S(=O)(=O)Nc3ncns3)ccc12]

The title compound was prepared in an analogous manner to that described in Example 28 using (3,5-dimethylisoxazol-4-yl)boronic acid and 3-bromo-N-(2,4-dimethoxybenzyl)-1-methyl-N-(1,2,4-thiadiazol-5-yl)-1H-indole-6-sulfonamide, and the desired product, 3-(3,5-dimethylisoxazol-4-yl)-1-methyl-N-(1,2,4-thiadiazol-5-yl)-1H-indole-6-sulfonamide, was isolated as an off-white solid. $^1$H NMR (500 MHz, DMSO-d$_6$) δ ppm 2.13 (s, 3 H) 2.31 (s, 3 H) 3.89 (s, 3 H) 7.41-7.49 (m, 2 H) 7.64 (s, 1 H) 7.90-7.93 (m, 1 H) 7.98 (s, 1 H). m/z (ESI) 389.1 (M+H)$^+$.

Example 43

3-(4-Bromo-2-(Trifluoromethyl)Phenyl)-1-Methyl-N-(1,2,4-Thiadiazol-5-yl)-1H-Indole-6-Sulfonamide

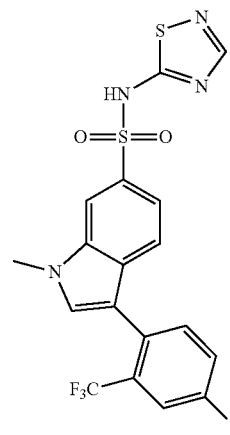

A vial containing 4-bromo-1-iodo-2-(trifluoromethyl)benzene was charged with potassium phosphate (0.130 g, 0.614 mmol), followed by a solution of N-(2,4-dimethoxybenzyl)-1-methyl-3-(4,4,5,5-tetramethyl-1,3,2-dioxaborolan-2-yl)-N-(1,2,4-thiadiazol-5-yl)-1H-indole-6-sulfonamide (Intermediate H) (0.100 g, 0.175 mmol) and PdCl$_2$(dppf)-CH$_2$Cl$_2$ (0.014 g, 0.018 mmol) in 1 mL of DMF. The vial was sealed and placed in a shaker block. The block was shaken for three hours at 85° C. The solution was filtered, washed with DMF and concentrated. The resulting solid was treated with a solution of TFA (0.270 mL, 3.51 mmol) in 1 mL of DCM. The vial was shaken at room temperature for two hours. The solution was concentrated and purified via reverse phase HPLC (8 min gradient elution 15 to 75% ACN/H$_2$O, 0.1% TFA modifier) to afford 3-(4-bromo-2-(trifluoromethyl)phenyl)-1-methyl-N-(1,2,4-thiadiazol-5-yl)-1H-indole-6-sulfonamide as an off-white solid. $^1$H NMR (500 MHz, DMSO-d$_6$) δ 3.95 (s, 3 H) 7.40-7.51 (m, 3 H) 7.69 (s, 1 H) 7.92-8.00 (m, 2 H) 8.03 (d, J=1.95 Hz, 1 H) 8.40 (s, 1 H). m/z (ESI) 515.9 (M+H)$^+$.

Example 44

1-Methyl-N-(1,2,4-Thiadiazol-5-yl)-3-(2-(Trifluoromethyl)Phenyl)-1H-Indole-6-Sulfonamide

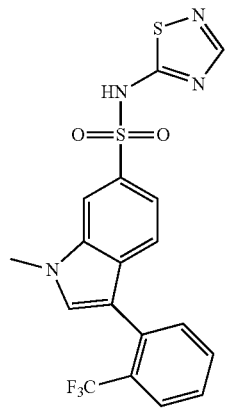 [SMILES: Cn1cc(-c2ccccc2C(F)(F)F)c2ccc(S(=O)(=O)Nc3ncns3)cc21]

The title compound was prepared in an analogous manner to that described in Example 43 using 1-bromo-2-(trifluoromethyl)benzene and the desired product, 1-methyl-N-(1,2,4-thiadiazol-5-yl)-3-(2-(trifluoromethyl)phenyl)-1H-indole-6-sulfonamide, was isolated as an off-white solid. $^1$H NMR (500 MHz, DMSO-d$_6$) δ ppm 3.95 (s, 3 H) 7.44-7.56 (m, 2 H) 7.56-7.63 (m, 1 H) 7.67 (s, 1 H) 7.74 (t, J=7.45 Hz, 1 H) 7.87 (d, J=7.90 Hz, 1 H) 7.99 (s, 1 H) 8.42 (s, 1 H). m/z (ESI) 438.0 (M+H)$^+$.

Example 45

3-(2-Amino-5-Methylpyridin-3-yl)-1-Methyl-N-(1,2,4-Thiadiazol-5-yl)-1H-Indole-6-Sulfonamide

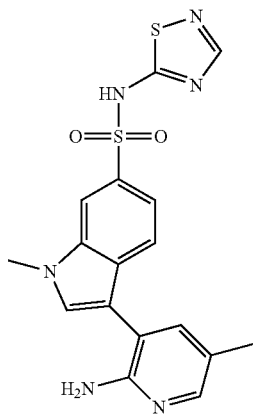

The title compound was prepared in an analogous manner to that described in Example 43 using 3-bromo-5-methylpyridin-2-amine and the desired product, 3-(2-amino-5-methylpyridin-3-yl)-1-methyl-N-(1,2,4-thiadiazol-5-yl)-1H-indole-6-sulfonamide, was isolated as an off-white solid. $^1$H NMR (500 MHz, DMSO-d$_6$) δ ppm=2.23 (s, 3 H) 3.95 (s, 3 H) 7.43 (br. s., 2 H) 7.55 (dd, J=8.42, 1.55 Hz, 1 H) 7.63 (d, J=8.48 Hz, 1 H) 7.78-7.93 (m, 3 H) 8.04 (s, 1 H) 8.40 (s, 1 H). m/z (ESI) 400.0 (M+H)$^+$.

EXAMPLE 46

3-(4-Cyano-2-Methylphenyl)-1-Methyl-N-(1,2,4-Thiadiazol-5-yl)-1H-Indole-6-Sulfonamide

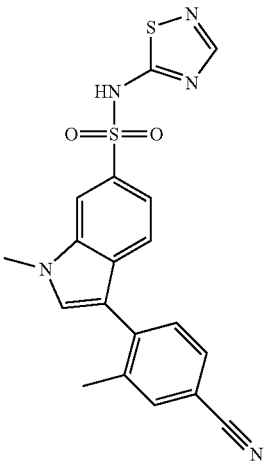 [SMILES: Cc1cc(C#N)ccc1-c1cn(C)c2cc(S(=O)(=O)Nc3ncns3)ccc12]

The title compound was prepared in an analogous manner to that described in Example 43 using 4-bromo-3-methylbenzonitrile and the desired product, 3-(4-cyano-2-methylphenyl)-1-methyl-N-(1,2,4-thiadiazol-5-yl)-1H-indole-6-sulfonamide, was isolated as an off-white solid. $^1$H NMR (500 MHz, DMSO-d$_6$) δ ppm=2.34 (s, 3 H) 3.96 (s, 3 H) 7.51-7.65 (m, 3 H) 7.71 (d, J=8.02 Hz, 1 H) 7.82 (s, 1 H) 7.88 (s, 1 H) 8.01 (s, 1 H) 8.42 (s, 1 H). m/z (ESI) 409.0 (M+H)$^+$.

EXAMPLE 47

3-(3-(Dimethylamino)Phenyl)-1-Methyl-N-(1,2,4-Thiadiazol-5-yl)-1H-Indole-6-Sulfonamide

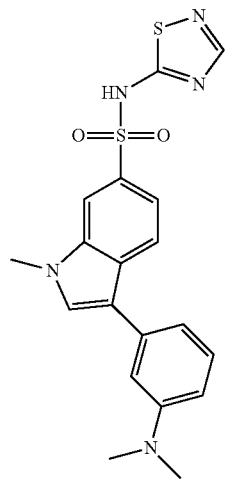 [SMILES: CN(C)c1cccc(-c2cn(C)c3cc(S(=O)(=O)Nc4ncns4)ccc23)c1]

The title compound was prepared in an analogous manner to that described in Example 43 using 3-bromo-N,N-dimethylaniline and the desired product, 3-(3-dimethylamino)phenyl)-1-methyl-N-(1,2,4-thiadiazol-5-yl)-1H-indole-6-sulfonamide, was isolated as an off-white solid. $^1$H NMR (500 MHz, DMSO-d$_6$) δ ppm=2.98 (s, 6 H) 3.93 (s, 3 H) 6.73 (m, 1 H) 6.97-7.04 (m, 2 H) 7.28 (t, J=7.68 Hz, 1 H) 7.53 (dd, J=8.48, 1.60 Hz, 1 H) 7.92 (s, 1 H) 7.96-8.04 (m, 2 H) 8.44 (s, 1 H). m/z (ESI) 413.1 (M+H)+.

Example 48

1-Methyl-N-(1,2,4-Thiadiazol-5-yl)-3-(3-(Trifluoromethyl)Phenyl)-1H-Indole-6-Sulfonamide

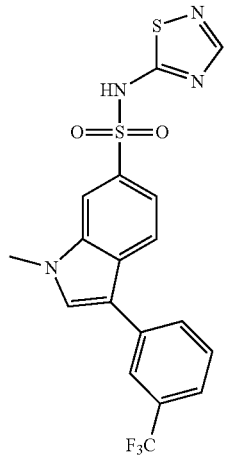 [SMILES: Cn1cc(-c2cccc(C(F)(F)F)c2)c2ccc(S(=O)(=O)Nc3ncns3)cc21]

The title compound was prepared in an analogous manner to that described in Example 43 using 1-iodo-3-(trifluoromethyl)benzene and the desired product, 1-methyl-N-(1,2,4-thiadiazol-5-yl)-3-(3-(trifluoromethyl)phenyl)-1H-indole-6-sulfonamide, was isolated as an off-white solid. $^1$H NMR (500 MHz, DMSO-$d_6$) δ ppm=3.95 (s, 3 H) 7.50-7.65 (m, 2 H) 7.69 (t, J=7.79 Hz, 1 H) 7.93 (s, 1 H) 7.98-8.10 (m, 3 H) 8.15 (s, 1 H) 8.43 (s, 1 H). m/z (ESI) 438.0 (M+H)+.

Example 49

3-(4-Methoxy-3-(Trifluoromethyl)Phenyl)-1-Methyl-N-(1,2,4-Thiadiazol-5-Yl)-1H-Indole-6-Sulfonamide

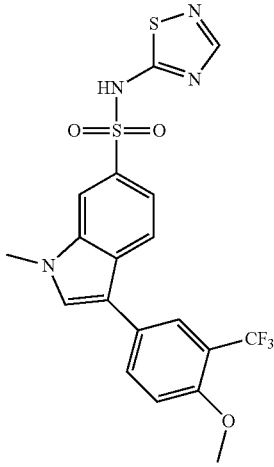 [SMILES: COc1ccc(-c2cn(C)c3cc(S(=O)(=O)Nc4ncns4)ccc23)cc1C(F)(F)F]

The title compound was prepared in an analogous manner to that described in Example 43 using 4-bromo-1-methoxy-2-(trifluoromethyl)benzene and the desired product, 3-(4-methoxy-3-(trifluoromethyl)phenyl)-1-methyl-N-(1,2,4-thiadiazol-5-yl)-1H-indole-6-sulfonamide, was isolated as an off-white solid. $^1$H NMR (500 MHz, DMSO-$d_6$) δ ppm=3.95 (s, 3 H) 7.59 (dd, J=8.53, 1.55 Hz, 1 H) 7.78 (d, J=8.36 Hz, 2 H) 7.90 (d, J=8.13 Hz, 2 H) 8.01 (d, J=1.38 Hz, 1 H) 8.07 (d, J=8.59 Hz, 1 H) 8.14 (s, 1 H) 8.43 (s, 1 H). m/z (ESI) 438.0 (M+H)+.

Example 50

N-(3-Bromo-1,2,4-Thiadiazol-5-Yl)-1-Methyl-3-(2-(1-Methyl-1H-Pyrazol-5-Yl)-4-(Trifluoromethyl)Phenyl)-1H-Indole-6-Sulfonamide

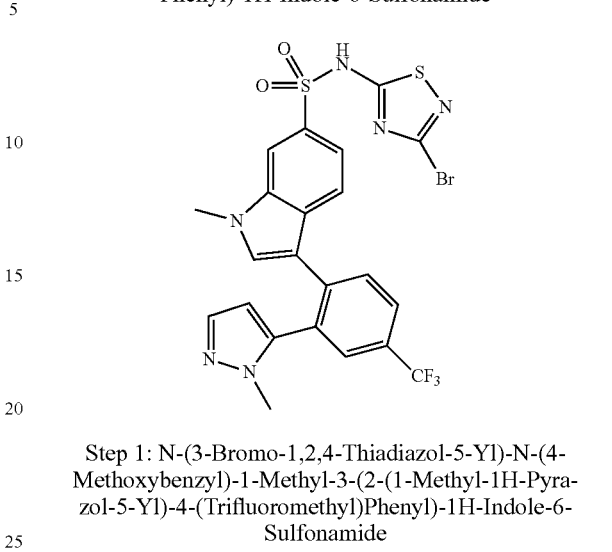

Step 1: N-(3-Bromo-1,2,4-Thiadiazol-5-Yl)-N-(4-Methoxybenzyl)-1-Methyl-3-(2-(1-Methyl-1H-Pyrazol-5-Yl)-4-(Trifluoromethyl)Phenyl)-1H-Indole-6-Sulfonamide A 25-mL round-bottom flask was charged with 3-bromo-N-(4-methoxybenzyl)-1,2,4-thiadiazol-5-amine (INTERMEDIATE K) (157 mg, 0.522 mmol) and THF (2.6 mL) to give a clear solution. The flask was cooled in a dry ice-acetone bath for 10 min, then lithium bis(trimethylsilyl)amide (1M in THF) (653 µl, 0.653 mmol) was added dropwise. The resulting clear solution was stirred for 20 min, then a solution perfluorophenyl 1-methyl-3-(2-(1-methyl-1H-pyrazol-5-yl)-4-(trifluoromethyl)phenyl)-1H-indole-6-sulfonate (INTERMEDIATE E) (157 mg, 0.261 mmol) in THF (1 mL with a 0.5 mL vial/syringe wash) was added dropwise over 1 min. The resulting solution was stirred for 10 min, then the flask was lowered into an ice bath for 2.5 h. The reaction mixture was quenched with saturated aq ammonium chloride solution, diluted with water, and extracted with EtOAc (2×). The combined organic extracts were concentrated, and the crude product was purified by chromatography on silica gel (0 to 60% EtOAc/Heptane) N-(3-bromo-1,2,4-thiadiazol-5-yl)-N-(4-methoxybenzyl)-1-methyl-3-(2-(1-methyl-1H-pyrazol-5-yl)-4-(trifluoromethyl)phenyl)-1H-indole-6-sulfonamide (136.87 mg, 0.191 mmol, 73.1% yield) as a white foam. $^1$H NMR (400 MHz, DMSO-$d_6$) δ=8.09 (d, J=1.8 Hz, 1 H), 7.96-7.83 (m, 2 H), 7.79 (d, J=1.4 Hz, 1 H), 7.66-7.49 (m, 2 H), 7.39 (d, J=1.9 Hz, 1 H), 7.31 (s, 1 H), 7.26 (d, J=8.8 Hz, 2 H), 6.86-6.79 (m, 2 H), 6.33 (d, J=1.9 Hz, 1 H), 5.08 (s, 2 H), 3.83 (s, 3 H), 3.68 (s, 3 H), 3.24 (s, 3H). m/z (ESI) 717.2 (M+H)+.

Step 2: N-(3-Bromo-1,2,4-Thiadiazol-5-Yl)-1-Methyl-3-(2-(1-Methyl-1H-Pyrazol-5-Yl)-4-(Trifluoromethyl)Phenyl)-1H-Indole-6-Sulfonamide A 10-mL round-bottom flask was charged with N-(3-bromo-1,2,4-thiadiazol-5-yl)-N-(4-methoxybenzyl)-1-methyl-3-(2-(1-methyl-1H-pyrazol-5-yl)-4-(trifluoromethyl)phenyl)-1H-indole-6-sulfonamide (28 mg, 0.039 mmol), DCM (1 mL), and trifluoroacetic acid (60.1 µl, 0.780 mmol). The flask was sealed, and the mixture was stirred for 2.5 h. An additional portion of TFA (0.15 mL) was added, and the resulting mixture was stirred for 48 h. The volatiles were removed in vacuo, and the residue was concentrated again from DCM. The crude product was purified by chromatography on silica gel (5 to 10% MeOH/DCM) to give N-(3-bromo-1,2,4-thiadiazol-5-yl)-1-methyl-3-(2-(1-methyl-1H- pyrazol-5-yl)-4-(trifluoromethyl)phenyl)-1H-indole-6-sulfonamide (19.91 mg, 0.033 mmol, 85% yield) as an off-white solid. ¹H NMR (400 MHz, DMSO-d₆) δ=7.94-7.83 (m, 3 H), 7.75 (s, 1 H), 7.55 (d, J=8.5 Hz, 1 H), 7.46-7.35 (m, 2 H), 7.05 (s, 1 H), 6.36 (d, J=1.9 Hz, 1 H), 3.78 (s, 3 H), 3.21 (s, 3 H). m/z (ESI) 597.0 (M+H)⁺.

Example 51

3-(3-Chloropyridin-4-Yl)-1-Methyl-N-(1,2,4-Thiadiazol-5-Yl)-1H-Indole-6-Sulfonamide

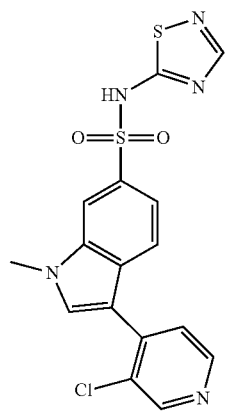 [SMILES: Cn1cc(-c2ccncc2Cl)c2ccc(S(=O)(=O)Nc3ncns3)cc21]

The title compound was prepared in an analogous manner to that described in Example 23 using 3-chloro-4-iodopyridine as the coupling partner to afford 3-(3-chloropyridin-4-yl)-1-methyl-N-(1,2,4-thiadiazol-5-yl)-1H-indole-6-sulfonamide as a dark-yellow solid. ¹H NMR (400 MHz, DMSO-d₆) δ=8.79 (s, 1 H), 8.58 (d, J=5.2 Hz, 1 H), 8.46 (s, 1 H), 8.19 (s, 1 H), 8.09-8.03 (m, 1 H), 7.81 (d, J=8.5 Hz, 1 H), 7.71 (d, J=5.2 Hz, 1 H), 7.59 (dd, J=1.7, 8.5 Hz, 1 H), 4.00 (s, 3 H). m/z (ESI) 406.0 (M+H)⁺.

Example 52

1-Methyl-3-(1-Methyl-1H-Pyrazol-5-Yl)-N-(1,2,4-Thiadiazol-5-Yl)-1H-Indole-6-Sulfonamide

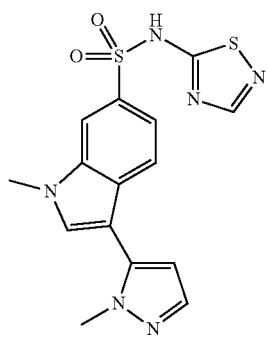 [SMILES: Cn1nccc1-c1cn(C)c2cc(S(=O)(=O)Nc3ncns3)ccc12]

The title compound was prepared in an analogous manner to that described in Example 28 using (1-methyl-1H-pyrazol-5-yl)boronic acid as the coupling partner to afford 1-methyl-3-(1-methyl-1h-pyrazol-5-yl)-n-(1,2,4-thiadiazol-5-yl)-1h-indole-6-sulfonamide as an off-white solid. ¹H NMR (500 MHz, DMSO-d₆) δ −0.50 (s, 1 H), 1.24 (br. s., 1 H), 3.17 (br. s., 2 H), 3.64 (s, 2 H), 3.85 (s, 3 H), 6.97 (br. s., 1 H), 7.08 (br. s., 1 H), 7.18 (br. s., 1 H), 7.47 (d, J=8.36 Hz, 1 H), 7.54 (dd, J=8.42, 1.43 Hz, 1 H), 7.73 (s, 1 H), 7.90 (s, 1 H), 7.97 (s, 1 H). m/z (ESI) 374.1 (M+H)⁺.

Example 53

1-Methyl-3-(1,2,3,4-Tetrahydroisoquinolin-5-Yl)-N-(1,2,4-Thiadiazol-5-Yl)-1H-Indole-6-Sulfonamide Hydrochloride

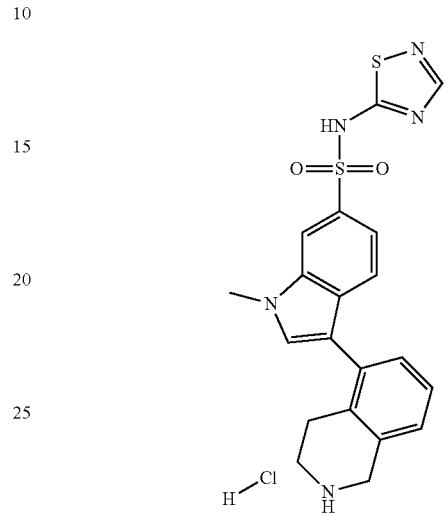

The title compound was prepared in an analogous manner to that described in Example 18 using tert-butyl 5-(4,4,5,5-tetramethyl-1,3,2-dioxaborolan-2-yl)-3,4-dihydroisoquinoline-2(1H)-carboxylate as the coupling partner to afford 1-methyl-3-(1,2,3,4-tetrahydroisoquinolin-5-yl)-N-(1,2,4-thiadiazol-5-yl)-1H-indole-6-sulfonamide hydrochloride as a brown solid. ¹H NMR (500 MHz, DMSO-d₆) δ=9.32 (br. s., 2 H), 8.40 (s, 1 H), 7.99 (s, 1 H), 7.70 (s, 1 H), 7.48 (s, 2 H), 7.39-7.29 (m, 2 H), 7.24 (br. s., 1 H), 4.32 (br. s., 2 H), 3.27 (br. s., 2 H), 2.86 (t, J=5.6 Hz, 2 H), 1.76 (s, 3 H). m/z (ESI) 426.2 (M+H)⁺.

Example 54

1-Methyl-3-(1,2,3,4-Tetrahydroisoquinolin-8-Yl)-N-(1,2,4-Thiadiazol-5-Yl)-1H-Indole-6-Sulfonamide Hydrochloride

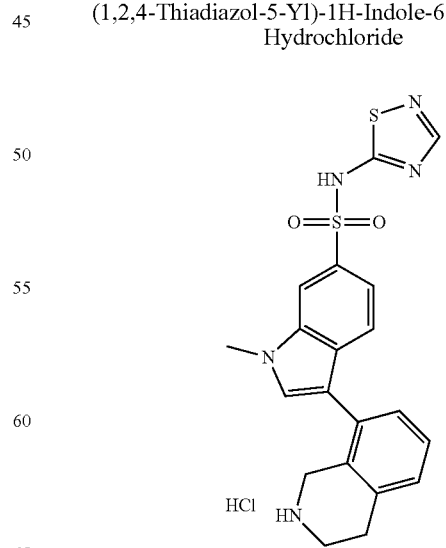

The title compound was prepared in an analogous manner to that described in Example 43 using tert-butyl 8-bromo-3, 4-dihydroisoquinoline-2(1H)-carboxylate as the coupling partner and employing a PEAX ion exchange column (eluting the product with HCl in MeOH/EtOAc) to afford 1-methyl-3-(1,2,3,4-tetrahydroisoquinolin-8-yl)-N-(1,2,4-thiadiazol-5-yl)-1H-indole-6-sulfonamide hydrochloride as light-pink solid. $^1$H NMR (400 MHz, DMSO-$d_6$) δ=7.89 (s, 1 H), 7.79 (s, 1 H), 7.57 (br. s., 1 H), 7.48 (d, J=8.2 Hz, 1 H), 7.39 (d, J=8.7 Hz, 1 H), 7.29 (d, J=7.9 Hz, 1 H), 7.25-7.13 (m, 2 H), 3.99 (br. s., 1 H), 3.89 (s, 3 H), 2.99 (br. s., 2 H). m/z (ESI) 426.0 (M+H)$^+$.

Example 55

3-(1-Cyclopropyl-1H-Pyrazol-4-Yl)-1-Methyl-N-(1,2,4-Thiadiazol-5-Yl)-1H-Indole-6-Sulfonamide

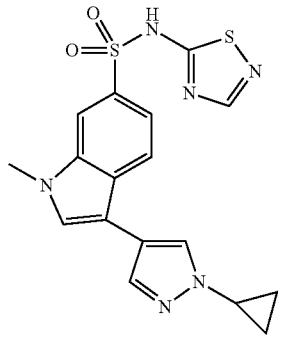 [SMILES: Cn1cc(-c2cnn(C3CC3)c2)c2ccc(S(=O)(=O)Nc3ncns3)cc21]

The title compound was prepared in an analogous manner to that described in Example 28 using 1-cyclopropyl-4-(4,4,5,5-tetramethyl-1,3,2-dioxaborolan-2-yl)-1H-pyrazoleas the coupling partner to afford 3-(1-cyclopropyl-1H-pyrazol-4-yl)-1-methyl-N-(1,2,4-thiadiazol-5-yl)-1H-indole-6-sulfonamide as an off-white solid. $^1$H NMR (600 MHz, DMSO-$d_6$) δ ppm 0.90-1.02 (m, 1 H), 1.05-1.14 (m, 1 H), 1.18-1.28 (m, 1 H), 2.08 (s, 4 H), 2.33-2.49 (m, 3 H), 2.51-2.54 (m, 1 H), 3.59 (br. s., 1 H), 3.74 (tdd, J=7.39, 7.39, 3.85, 3.74 Hz, 1 H), 3.84 (s, 1 H), 7.47 (dd, J=8.40, 1.58 Hz, 1 H), 7.69 (br. s., 1 H) 7.76 (s, 1 H), 7.80-7.89 (m, 1 H), 7.99 (br. s., 1 H), 8.08-8.15 (m, 1 H). m/z (ESI) 401.3 (M+H)$^+$.

Example 56

3-(5-Fluoro-2-Methoxypyridin-4-Yl)-1-Methyl-N-(1,2,4-Thiadiazol-5-Yl)-1H-Indole-6-Sulfonamide

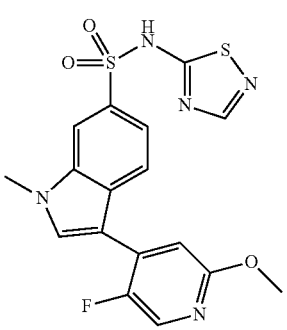

The title compound was prepared in an analogous manner to that described in Example 28 using (5-fluoro-2-methoxypyridin-4-yl)boronic acid as the coupling partner to afford 3-(5-fluoro-2-methoxypyridin-4-yl)-1-methyl-N-(1,2,4-thiadiazol-5-yl)-1H-indole-6-sulfonamide as an off-white solid. $^1$H NMR (500 MHz, DMSO-$d_6$) δ ppm−0.50 (s, 1 H), 1.23 (br. s., 1 H), 3.76-3.82 (m, 1 H), 3.87 (s, 2 H), 3.94 (s, 3 H), 6.98 (s, 1 H), 7.06-7.14 (m, 1 H), 7.18 (s, 1 H), 7.59 (dd, J=8.53, 1.55 Hz, 1 H), 7.88 (d, J=8.13 Hz, 1 H) 7.96 (d, J=1.15 Hz, 1 H), 8.04-8.11 (m, 2 H), 8.20 (d, J=2.63 Hz, 1 H). m/z (ESI) 420.3 (M+H)$^+$.

Example 57

1-Methyl-N-(1,2,4-Thiadiazol-5-Yl)-3-(4-(Trifluoromethyl)Phenyl)-1H-Indole-6-Sulfonamide

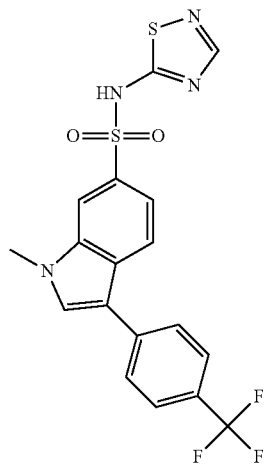 [SMILES: Cn1cc(-c2ccc(C(F)(F)F)cc2)c2ccc(S(=O)(=O)Nc3ncns3)cc21]

The title compound was prepared in an analogous manner to that described in Example 43 using 4-iodobenzotrifluoride, and the desired product, 1-methyl-N-(1,2,4-thiadiazol-5-yl)-3-(4-(trifluoromethyl)phenyl)-1H-indole-6-sulfonamide, was isolated as an off-white solid. $^1$H NMR (500 MHz, DMSO-$d_6$) δ ppm−0.50 (s, 1 H), 1.23 (s, 1 H), 3.17 (br. s., 1 H), 3.55 (s, 1 H), 3.95 (s, 2 H), 7.59 (dd, J=8.53, 1.55 Hz, 1 H), 7.78 (d, J=8.36 Hz, 1 H), 7.90 (d, J=8.13 Hz, 2 H), 8.01 (d, J=1.38 Hz, 1 H), 8.07 (d, J=8.59 Hz, 1 H), 8.14 (s, 1 H) 8.43 (s, 1 H). m/z (ESI) 438.7 (M+H)$^+$.

Example 58

1-Methyl-N-(1,2,4-Thiadiazol-5-Yl)-3-(2-(Trifluoromethoxy)Phenyl)-1H-Indole-6-Sulfonamide

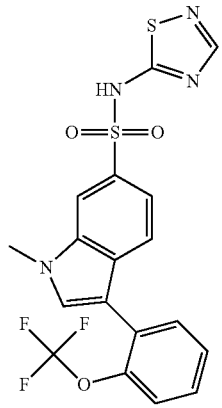 [SMILES: Cn1cc(-c2ccccc2OC(F)(F)F)c2ccc(S(=O)(=O)Nc3ncns3)cc21]

The title compound was prepared in an analogous manner to that described in Example 43 using 1-iodo-2-(trifluoromethoxy)benzene, and the desired product, 1-methyl-N-(1,2,4-thiadiazol-5-yl)-3-(2-(trifluoromethoxy)phenyl)-1H-indole-6-sulfonamide, was isolated as an off-white solid. $^1$H NMR (500 MHz, DMSO-$d_6$) δ ppm−0.50 (s, 2 H), 1.24 (s, 1 H), 3.17 (br. s., 1 H), 3.93 (d, J=2.41 Hz, 4 H), 7.37 (d, J=8.48

Hz, 1 H), 7.56 (dd, J=8.48, 1.60 Hz, 1 H), 7.79 (s, 1 H), 7.87-7.95 (m, 1H), 7.97-8.01 (m, 1 H), 8.41 (s, 1 H). m/z (ESI) 455.0 (M+H)$^+$.

Example 59

3-(Benzofuran-2-Yl)-1-Methyl-N-(1,2,4-Thiadiazol-5-Yl)-1H-Indole-6-Sulfonamide

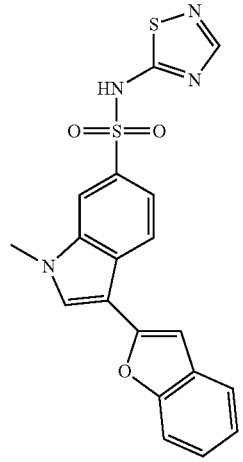 [SMILES: Cn1cc(-c2cc3ccccc3o2)c2ccc(S(=O)(=O)Nc3ncns3)cc21]

The title compound was prepared in an analogous manner to that described in Example 43 using 2-bromobenzofuran, and the desired product, 3-(benzofuran-2-yl)-1-methyl-N-(1,2,4-thiadiazol-5-yl)-1H-indole-6-sulfonamide, was isolated as an off-white solid. $^1$H NMR (500 MHz, DMSO-d$_6$) δ 8.21 (s, 1H), 7.56-7.65 (m, 1H), 7.24 (s, 1H), 3.95 (s, 1H), 3.16 (s, 2H), 2.50 (s, 7H), −0.50 (s, 1H). m/z (ESI) 410.8 (M+H)$^+$.

Example 60

3-(3-Cyano-4-Methoxyphenyl)-1-Methyl-N-(1,2,4-Thiadiazol-5-Yl)-1H-Indole-6-Sulfonamide

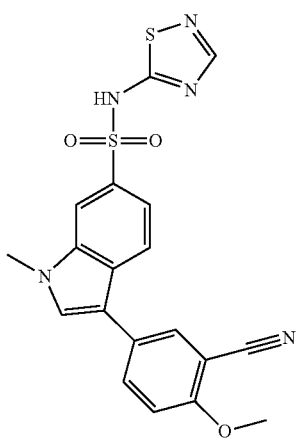 [SMILES: COc1ccc(-c2cn(C)c3cc(S(=O)(=O)Nc4ncns4)ccc23)cc1C#N]

The title compound was prepared in an analogous manner to that described in Example 43 using 5-bromo-2-methoxybenzonitrile, and the desired product, 3-(3-cyano-4-methoxyphenyl)-1-methyl-N-(1,2,4-thiadiazol-5-yl)-1H-indole-6-sulfonamide, was isolated as an off-white solid. $^1$H NMR (500 MHz, DMSO-d$_6$) δ 7.90-7.98 (m, 1H), 7.61 (d, J=8.13 Hz, 1H), 7.36 (d, J=8.13 Hz, 1H), 7.22 (s, 2H), 7.12 (s, 2H), 7.01 (s, 2H), 5.73 (s, 1H), 3.91 (s, 1H), 3.17 (s, 2H), 2.91 (s, 1H), 2.83 (s, 1H), 2.54 (s, 1H), −0.50 (s, 1H). m/z (ESI) 425.8 (M+H)$^+$.

Example 61

3-(6-Methoxypyridin-3-Yl)-1-Methyl-N-(1,2,4-Thiadiazol-5-Yl)-1H-Indole-6-Sulfonamide

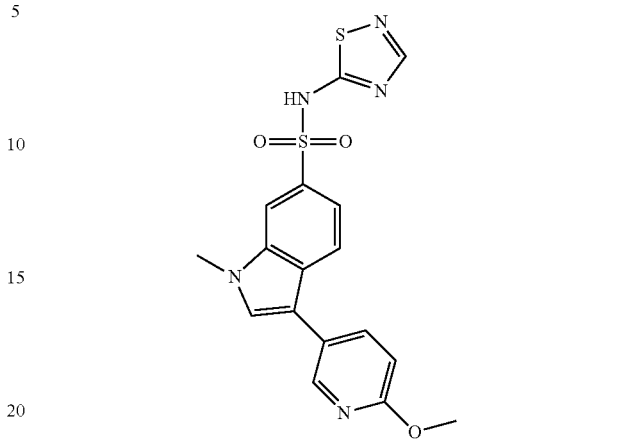

The title compound was prepared in an analogous manner to that described in Example 43 using 5-iodo-2-methoxypyridine, and the desired product, 3-(6-methoxypyridin-3-yl)-1-methyl-N-(1,2,4-thiadiazol-5-yl)-1H-indole-6-sulfonamide, was isolated as an off-white solid. $^1$H NMR (500 MHz, DMSO-d$_6$) δ 8.42-8.47 (m, 1H), 7.83-8.01 (m, 2H), 7.53 (dd, J=1.55, 8.53 Hz, 1H), 7.22 (s, 1H), 7.12 (s, 1H), 7.02 (s, 1H), 6.92 (d, J=8.48 Hz, 1H), 3.91 (d, J=18.33 Hz, 4H), 3.82 (d, J=3.09 Hz, 2H), 3.17 (s, 1H), −0.50 (s, 1H). m/z (ESI) 401.8 (M+H)$^+$.

Example 62

1-(4-Chloro-2-(1-Methyl-1H-Pyrazol-5-Yl)Phenyl)-N-(1,2,4-Thiadiazol-5-Yl)-1H-Benzo[D]Imidazole-5-Sulfonamide

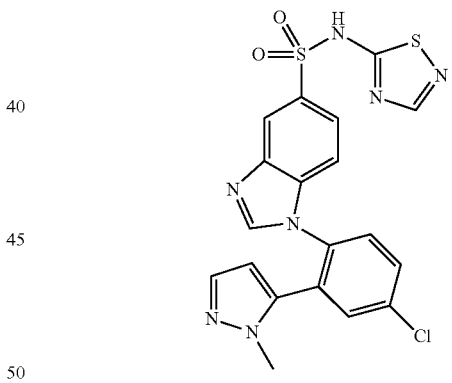

Step 1: 4-((4-Chloro-2-(1-Methyl-1H-Pyrazol-5-Yl)Phenyl)Amino)-N-(2,4-Dimethoxybenzyl)-3-Nitro-N-(1,2,4-Thiadiazol-5-Yl)Benzenesulfonamide A round-bottom flask was charged with N-(2,4-dimethoxybenzyl)-4-fluoro-3-nitro-N-(1,2,4-thiadiazol-5-yl)benzenesulfonamide (INTERMEDIATE M) (189 mg, 0.416 mmol), 4-chloro-2-(1-methyl-1H-pyrazol-5-yl)aniline (the product of STEP 1 in the preparation of INTERMEDIATE F) (95 mg, 0.457 mmol), and THF (2079 μl) to give a brown solution. The flask was cooled in an ice bath for 5 min, then lithium bis(trimethylsilyl)amide (1M in THF) (1248 μl, 1.248 mmol) was added dropwise over 1 minute to give a dark maroon mixture. After 10 min, the mixture was diluted with a saturated aq. ammonium chloride solution and water, then extracted with EtOAc (3×). The combined organic extracts were dried over sodium sulfate, filtered and concentrated. The crude product was purified by chromatography on silica gel (20 to 70% EtOAc/heptane) give 4-((4-chloro-2-(1-methyl-1H-pyrazol-5-yl)phenyl)amino)-N-(2,4-dimethoxybenzyl)-3-nitro-N-(1,2,4-thiadiazol-5-yl)benzenesulfonamide (197.46 mg, 0.308 mmol, 73.9% yield) as a bright orange solid. m/z (ESI) 642.0 (M+H)$^+$.

Step 2: 1-(4-Chloro-2-(1-Methyl-1H-Pyrazol-5-Yl)Phenyl)-N-(1,2,4-Thiadiazol-5-Yl)-1H-Benzo[D]Imidazole-5-Sulfonamide A vial was charged with 4-((4-chloro-2-(1-methyl-1H-pyrazol-5-yl)phenyl)amino)-N-(2,4-dimethoxybenzyl)-3-nitro-N-(1,2,4-thiadiazol-5-yl)benzenesulfonamide (95.54 mg, 0.149 mmol), iron (83 mg, 1.488 mmol), THF (0.5 mL) and acetic acid (0.5 mL). The vial was sealed and heated in a 70° C. bath for 1 h. After cooling to room temperature, the mixture was diluted with DCM and MeOH, then filtered through Celite® (diatomaceous earth). The filtrate was concentrated under a vacuum, and the residue was taken up in a saturated aq. sodium bicarbonate solution. The mixture was extracted with EtOAc (3×), and the combined organic extracts were dried over sodium sulfate, filtered and concentrated to give an off-white foam. The foam was transferred to a microwave vial and dissolved in formic acid (0.75 mL). The resulting mixture was heated to 110° C. for 12 h (microwave). After cooling to room temperature, the mixture was diluted with methanol and DCM, transferred to a flask, and concentrated under a vacuum. The residue was diluted with 2N ammonia in methanol (about 25 mL), then concentrated again. The residue was taken up in MeOH/DCM to give an opaque mixture which was purified by chromatography on silica gel (0 to 10% MeOH/DCM) to give 1-(4-chloro-2-(1-methyl-1H-pyrazol-5-yOphenyl)-N-(1,2,4-thiadiazol-5-yl)-1H-benzo[d]imidazole-5-sulfonamide (52.08 mg, 0.110 mmol, 74.2% yield) as an off-white solid. $^1$H NMR (400 MHz, DMSO-d$_6$) δ=8.39-8.31 (m, 2 H), 8.06 (d, J=1.3 Hz, 1 H), 7.88 (d, J=2.1 Hz, 1 H), 7.85-7.74 (m, 2 H), 7.64 (dd, J=1.8, 8.6 Hz, 1 H), 7.37 (d, J=8.6 Hz, 1 H), 7.21 (d, J=2.0 Hz, 1 H), 5.86 (d, J=1.9 Hz, 1 H), 3.59 (s, 3 H). m/z (ESI) 472.0 (M+H)$^+$.

Example 63

1-(2-(1-Methyl-1H-Pyrazol-5-Yl)-4-(Trifluoromethyl)Phenyl)-N-(1,2,4-Thiadiazol-5-Yl)-1H-Benzo[D]Imidazole-5-Sulfonamide

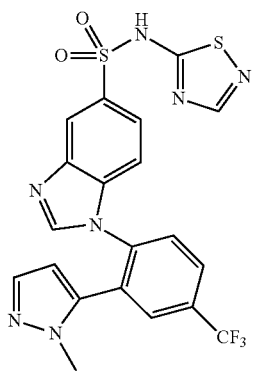 [SMILES: Cn1nccc1-c1cc(C(F)(F)F)ccc1-n1cnc2cc(S(=O)(=O)Nc3ncns3)ccc21]

The title compound was prepared in an analogous manner to that described in Example 62, except that 2-(1-methyl-1H-pyrazol-5-yl)-4-(trifluoromethyl)aniline (INTERMEDIATE L) was used in place of 4-chloro-2-(1-methyl-1H-pyrazol-5-yl)aniline in STEP 1. The desired product, 1-(2-(1-methyl-1h-pyrazol-5-yl)-4-(trifluoromethyl)phenyl)-n-(1,2,4-thiadiazol-5-yl)-1h-benzo[d]imidazole-5-sulfonamide, was isolated as a bright-yellow solid. $^1$H NMR (400 MHz, DMSO-d$_6$) δ=8.38 (s, 1 H), 8.33 (s, 1 H), 8.18-8.12 (m, 2 H), 8.08 (d, J=1.4 Hz, 1 H), 8.01 (d, J=8.0 Hz, 1 H), 7.66 (dd, J=1.7, 8.6 Hz, 1H), 7.42 (d, J=8.6 Hz, 1H), 7.26 (d, J=1.9 Hz, 1 H), 5.95 (d, J=2.0 Hz, 1 H), 3.57 (s, 3 H). m/z (ESI) 506.0 (M+H)$^+$.

Example 64

1-Methyl-3-(1,2,3,4-Tetrahydroisoquinolin-8-Yl)-N-(1,2,4-Thiadiazol-5-Yl)-1H-Indole-6-Sulfonamide

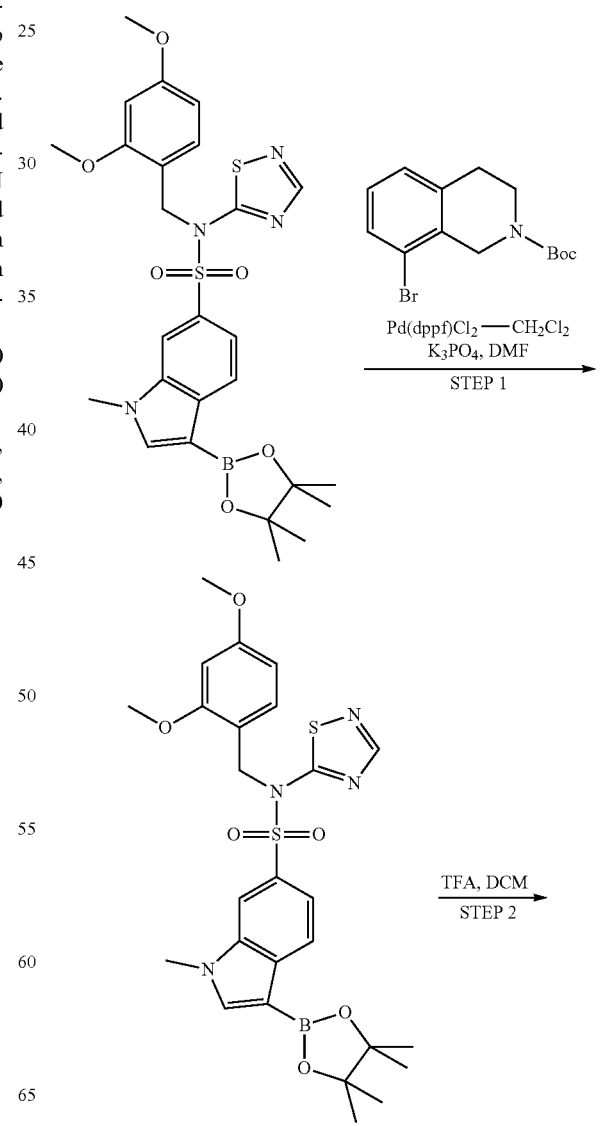

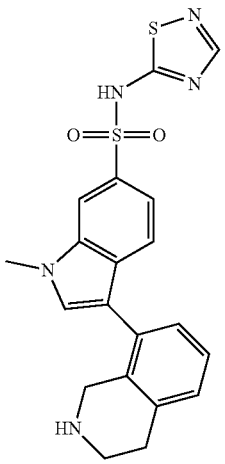

Step 1: Tert-Butyl 8-(6-(N-(2,4-Dimethoxybenzyl)-N-(1,2,4-Thiadiazol-5-Yl)Sulfamoyl)-1-Methyl-1H-Indol-3-Yl)-3,4-Dihydroisoquinoline-2(1H)-Carboxylate A vial was charged with N-(2,4-dimethoxybenzyl)-1-methyl-3-(4,4,5,5-tetramethyl-1,3,2-dioxaborolan-2-yl)-N-(1,2,4-thiadiazol-5-yl)-1H-indole-6-sulfonamide (Intermediate H)(0.188 g, 0.330 mmol), tert-butyl 8-bromo-3,4-dihydroisoquinoline-2(1H)-carboxylate (0.257 g, 0.824 mmol), potassium phosphate (0.315 g, 1.483 mmol), and PdCl$_2$(dppf)-CH$_2$Cl$_2$ adduct (0.027 g, 0.033 mmol). DMF (2.197 ml) was added, and the vial was flushed with argon, sealed, and stirred at 85° C. for two hours. Additional tert-butyl 8-bromo-3,4-dihydroisoquinoline-2(1H)-carboxylate (Oakwood Inc., West Columbia, S.C.) (0.257 g, 0.824 mmol) was added and the reaction was stirred at 85° C. for two hours. The reaction was diluted with ethyl acetate and washed with water. The aqueous layer was extracted with ethyl acetate, and the combined organic layers were washed with brine, dried with sodium sulfate, filtered, and concentrated. The material was purified via column chromatography (RediSep Gold 40 g silica gel column (Teledyne Isco, Lincoln, Nebr.), gradient elution 0 to 100% EtOAc:Hex) to afford tert-butyl 8-(6-(N-(2,4-dimethoxybenzyl)-N-(1,2,4-thiadiazol-5-yl)sulfamoyl)-1-methyl-1H-indol-3-yl)-3,4-dihydroisoquinoline-2(1H)-carboxylate as a light yellow solid.

Step 2: 1-Methyl-3-(1,2,3,4-Tetrahydroisoquinolin-8-Yl)-N-(1,2,4-Thiadiazol-5-Yl)-1H-Indole-6-Sulfonamide Tert-butyl 8-(6-(N-(2,4-dimethoxybenzyl)-N-(1,2,4-thiadiazol-5-yl)sulfamoyl)-1-methyl-1H-indol-3-yl)-3,4-dihydroisoquinoline-2(1H)-carboxylate (0.223 g, 0.330 mmol) was dissolved in 0.5 mL of DCM and TFA (0.1 ml, 1.298 mmol) was added. The reaction was stirred overnight at room temperature. The reaction was concentrated, dissolved in acetonitrile, and passed through a Biotage Isolute® PE-AX ion exchange column (Biotage AB, Uppsala, SE). The column was flushed several times with acetonitrile, then the product was liberated by flushing several times with an HCl solution in 15% MeOH/EtOAc. The resulting solution was concentrated. The material was redissolved in DCM and ethyl acetate and dried over magnesium sulfate. The solution was filtered and concentrated to afford 1-methyl-3-(1,2,3,4-tetrahydroisoquinolin-8-yl)-N-(1,2,4-thiadiazol-5-yl)-1H-indole-6-sulfonamide as a light pink solid. m/z (ESI) 427.0 (M+H)$^+$. $^1$H NMR (400 MHz, DMSO-d$_6$) δ ppm=7.89 (s, 1 H), 7.79 (s, 1 H), 7.57 (br. s., 1 H), 7.48 (d, J=8.2 Hz, 1 H), 7.39 (d, J=8.7 Hz, 1 H), 7.29 (d, J=7.9 Hz, 1 H), 7.25-7.13 (m, 2 H), 3.99 (br. s., 1 H), 3.89 (s, 3 H), 2.99 (br. s., 2 H)

Example 65

1-Methyl-3-(2-(1,2,3,6-Tetrahydropyridin-4-Yl)-4-(Trifluoromethyl)Phenyl)-N-(Thiazol-2-Yl)-1H-Indole-6-Sulfonamide 2,2,2-Trifluoroacetate

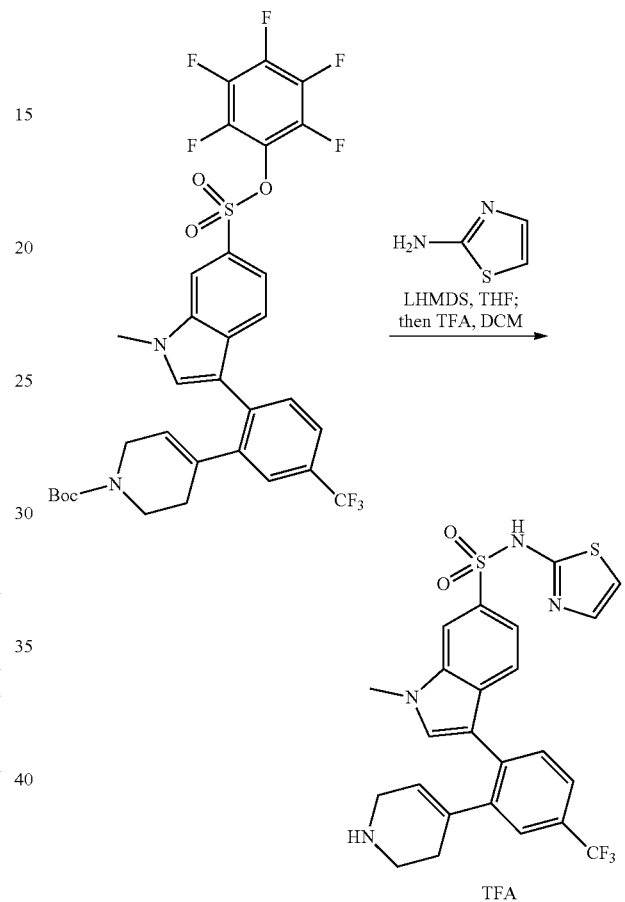

A flask containing a mixture of 2-aminothiazole (7.93 mg, 0.079 mmol), tert-butyl 4-(2-(1-methyl-6-((perfluorophenoxy)sulfonyl)-1H-indol-3-yl)-5-(trifluoromethyl)phenyl)-5,6-dihydropyridine-1(2H)-carboxylate (INTERMEDIATE O) (0.053 g, 0.075 mmol), and THF (0.503 ml) was cooled to 0° C. LHMDS (1.0M in THF) (0.151 ml, 0.151 mmol) was added dropwise and the reaction was stirred for 15 minutes at 0° C. An additional equivalent of aminothiazole was added, followed by 2 equivalents of LHMDS solution. The reaction was stirred for one hour at 0° C. The reaction was quenched with saturated ammonium chloride solution, diluted with DCM, and the layers were separated. The aqueous layer was extracted with DCM, and the combined organic layers were concentrated. The material was dissolved in DCM and TFA (0.1 ml, 1.298 mmol) was added. The reaction was stirred at 50° C. overnight. The reaction was concentrated and the material was purified via column chromatography (RediSep Gold 12 g silica gel column (Teledyne Isco, Lincoln, Nebr., gradient elution 0 to 10% MeOH:DCM) to afford 1-methyl-3-(2-(1,2,3,6-tetrahydropyridin-4-yl)-4-(trifluoromethyl)phenyl)-N-(thiazol-2-yl)-1H-indole-6-sulfonamide 2,2,2-trifluoroacetate as a tan solid. m/z (ESI) 519.4 (M+H)$^+$. $^1$H NMR (400 MHz, DMSO-d$_6$) δ ppm=12.61 (br. s., 1 H), 8.70

(br. s., 2 H), 7.99 (s, 1 H), 7.81-7.67 (m, 5 H), 7.59-7.52 (m, 2 H), 7.24 (d, J=4.8 Hz, 1 H), 6.81 (d, J=4.5 Hz, 1 H), 5.89 (br. s., 1 H), 3.95 (s, 3 H), 3.71 (br. s., 2 H), 2.98 (br. s., 2 H), 2.11 (br. s., 3 H)

Example 66

1-Methyl-3-(2-(1,2,3,6-Tetrahydropyridin-4-Yl)-4-(Trifluoromethyl)Phenyl)-N-(Thiazol-4-Yl)-1H-Indole-6-Sulfonamide

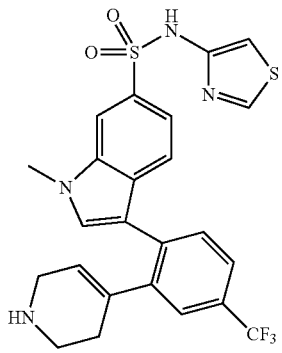 [SMILES: Cn1cc(-c2ccc(C(F)(F)F)cc2C2=CCNCC2)c2ccc(S(=O)(=O)Nc3cscn3)cc21]

The title compound was prepared in an analogous manner to that described for Example 65, except that 4-aminothiazole was used in place of 2-aminothiazole, and the final product was purified via reverse-phase HPLC (Phenomenex $C_{18}$ column 150×30 mm, 5 micron; 25 to 70% MeCN:$H_2O$ w/0.1% TFA modifier (Phenomenex, Torrance, Calif.)). The product fractions were partitioned between ethyl acetate and saturated sodium bicarbonate solution. The aqueous layer was extracted with ethyl acetate, and the combined organic layers were dried with sodium sulfate, filtered, and concentrated to afford 1-methyl-3-(2-(1,2,3,6-tetrahydropyridin-4-yl)-4-(trifluoromethyl)phenyl)-N-(thiazol-4-yl)-1H-indole-6-sulfonamide as a tan solid. m/z (ESI) 519.3 (M+H)$^+$. $^1$H NMR (500 MHz, DMSO-$d_6$) δ ppm=8.80 (d, J=1.9 Hz, 1 H), 8.02 (s, 1 H), 7.73 (s, 1 H), 7.71-7.68 (m, 1 H), 7.67-7.62 (m, 2 H), 7.54-7.50 (m, 2 H), 6.93 (s, 1 H), 5.81 (br. s., 1 H), 3.91 (s, 4 H), 2.63 (br. s., 2 H), 1.88 (br. s., 2 H)

Nav 1.7 and Nav 1.5 In Vitro Assay 293 cells stably transfected with either Nav 1.7 or with Nav 1.5 were recorded in population patch-clamp mode with the IonWorks® Quattro automated electrophysiology system in accordance with the manufacturer's specifications (Molecular Devices, LLC, Sunnyvale, Calif.). Sodium channel currents were measured in response to a train of depolarizations that induced successively greater inactivation.

Cells were held at −110 mV for three seconds (Nav 1.7) or half a second (Nav 1.5) from a holding voltage of −15 mV, then put through a series of 26 pulses of 150 msec duration to −20 mV at a frequency of 5 Hz. Cells were then left unclamped for a period of 3 to 8 minutes while a single concentration of test compound was added. Cells were then reclamped and put through the same voltage protocol. Current at the end of the 26$^{th}$ pulse to −20 mV was subtracted from the peak current evoked by the 26$^{th}$ pulse to −20 mV to correct for leak current. Percent block was calculated for each concentration in duplicate, and IC$_{50}$ curves were fitted to percent block as a function of concentration. Data for compounds of the present invention are shown in the table below.

| Example No. | Nav 1.7 IC$_{50}$ (μM) or % inhibition at 4.9 μM | Nav 1.5 IC$_{50}$ (μM) |
|---|---|---|
| 1 | 0.445 μM | >10.0 |
| 2 | 0.253 μM | >10.0 |
| 3 | 1.93 μM | >10.0 |
| 4 | 0.0505 μM | >10.0 |
| 5 | 0.724 μM | >10.0 |
| 6 | 0.356 μM | >10.0 |
| 7 | 0.532 μM | >10.0 |
| 8 | 0.147 μM | >10.0 |
| 9 | 1.7 μM | >10.0 |
| 10 | 2.13 μM | >10.0 |
| 11 | 3.19 μM | >10.0 |
| 12 | 0.835 μM | >10.0 |
| 13 | 1.86 μM | >10.0 |
| 14 | 3.29 μM | >10.0 |
| 15 | 1.54 μM | >10.0 |
| 16 | 0.551 μM | >10.0 |
| 17 | 9.11 μM | >10.0 |
| 18 | 0.05 μM | >10.0 |
| 19 | 0.263 μM | >10.0 |
| 20 | 36.2% | >10.0 |
| 21 | 0.0375 μM | >10.0 |
| 22 | 0.0425 μM | >10.0 |
| 23 | 0.687 μM | >10.0 |
| 24 | 3.19 μM | >10.0 |
| 25 | 6.7 μM | 8.55 |
| 26 | 1.02 μM | >10.0 |
| 27 | 0.674 μM | >10.0 |
| 28 | 0.338 μM | >10.0 |
| 29 | 5.96 μM | >10.0 |
| 30 | 1.28 μM | 7.63 |
| 31 | 3.06 μM | >10.0 |
| 32 | 4.67 μM | >10.0 |
| 33 | 0.87 μM | >10.0 |
| 34 | 2 μM | >10.0 |
| 35 | 1.55 μM | >10.0 |
| 36 | 0.904 μM | >10.0 |
| 37 | 0.306 μM | >10.0 |
| 38 | 0.663 μM | >10.0 |
| 39 | 0.528 μM | >10.0 |
| 40 | 2.64 μM | >10.0 |
| 41 | 2.31 μM | >10.0 |
| 42 | 2.62 μM | >10.0 |
| 43 | 3.53 μM | >10.0 |
| 44 | 6 μM | >10.0 |
| 45 | 5.95 μM | >10.0 |
| 46 | 2.35 μM | >10.0 |
| 47 | 4.2 μM | >10.0 |
| 48 | 3.81 μM | >10.0 |
| 49 | 4.48 μM | >10.0 |
| 50 | 1.38 μM | >10.0 |
| 51 | 8.53 μM | >10.0 |
| 52 | 7.14 μM | >10.0 |
| 53 | 0.292 μM | >10.0 |
| 54 | 1.63 μM | >10.0 |
| 55 | 20.5% | >10.0 |
| 56 | 20.8% | >10.0 |
| 57 | 23.3% | >10.0 |
| 58 | 25.1% | >10.0 |
| 59 | 36.2% | >10.0 |
| 60 | 24.7% | >10.0 |
| 61 | 37.2% | >10.0 |
| 62 | 2.68 μM | >10.0 |
| 63 | 1.13 μM | >10.0 |
| 64 | 1.63 μM | >10.0 |
| 65 | 0.269 μM | >10.0 |
| 66 | 1.41 μM | >10.0 |

The compounds of the present invention may also be tested in the following in vivo assays.

Rat Formalin Model of Persistent Pain

On the test day, animals (Naïve, male Sprague Dawley rats) weighing between 260-300 g at the start of testing can be obtained from Harlan (Indianapolis, Ind.). All animals may be housed under a 12/12 h light/dark cycle with lights on at 0600. Rodents can be housed two to a cage on solid bottom cages with corn cob bedding and can have access to food and water ad libitum. Animals should be allowed to habituate to the vivarium for at least five days before testing is begun and should be brought into the testing room at least 30 minutes prior to dosing. Animals are pretreated with the appropriate test compound either by oral gavage or intraperitoneal injection at the desired pretreatment time (typically two hours before test onset) and then returned to their home cages. After dosing and at least 30 minutes prior to test onset, animals can be acclimated to the individual testing chambers. At test time, each animal can be gently wrapped in a towel with the left hindpaw exposed. A dilute solution of formalin (2.5%) in phosphate buffered saline can be injected subcutaneously into the dorsal surface of the left hindpaw in a volume to 50 µL with a 30 g needle. Immediately following injection, a small metal band can be affixed to the plantar side of the left hindpaw with a drop of loctite. Animals may be then placed into the testing chambers and the number of flinches can be recorded between 10-40 minutes after formalin injection. A flinch is defined as a quick and spontaneous movement of the injected hindpaw not associated with ambulation. Flinches can be quantified with the aid of the Automated Nociception Analyzer built by the University of California, San Diego Department of Anesthesiology. Individual data can be expressed as a % maximal potential effect (% MPE) calculated with the following formula:

(−(Individual score−Vehicle average score)/Vehicle average score))*100=% MPE

Statistical analysis can be performed by analysis of variance (ANOVA), with post-hoc analysis using Bonferroni compared to the vehicle group for a significant main effect. Data can be represented as mean % MPE+/−standard error for each group.

Rat Open Field Assay

On the test day, animals (Naïve, male Sprague Dawley rats) weighing between 260-300 g at the start of testing may be obtained from Harlan (Indianapolis, Ind.). All animals can be housed under a 12/12 h light/dark cycle with lights on at 0600. Rodents can be housed two to a cage on solid bottom cages with corn cob bedding and can have access to food and water ad libitum. Animals should be allowed to habituate to the vivarium for at least five days before testing is begun and should be brought into the testing room at least 30 minutes prior to dosing. In a room separate from the testing room, animals can be pretreated with the appropriate test compound either by oral gavage or intraperitoneal injection at the desired pretreatment time (typically two hours before test onset) and then can be returned to their home cages until the pretreatment has elapsed. At test time, animal can be transferred to the open field testing room in their home cages. Each animal may be placed in a separate testing chamber and the motion tracking system is started. The house lights in the testing room should be turned off and the animals can be allowed to explore the novel open field for 30 minutes. An automated motion tracker, made by San Diego Instruments, San Diego, Calif., can be used to capture animal exploration with the aid of infrared photo beams to detect animal movement. These behaviors include basic movement and vertical rearing, which can be used as the primary endpoints for this assay. At the end of the test, house lights can be turned on and the animals should be removed from the testing apparatus. Data can be expressed as a percent change from the vehicle control using the following equation.

(1−(Test mean/Vehicle mean))*100=% Change.

Statistical analysis can be performed by analysis of variance (ANOVA), with post-hoc analysis using Dunnett to follow up significant main effects.

CFA-Thermal Assay

Animals (Naïve, male Sprague Dawley rats) weighing between 260-300 g at the start of testing) can be obtained from Harlan (Indianapolis, Ind.). All animals can be housed under a 12/12 h light/dark cycle with lights on at 0600. Rodents may be housed two to a cage on solid bottom cages with corn cob bedding with access to food and water ad libitum. Animals can be allowed to habituate to the vivarium for at least five days before testing was begun and may be brought into the testing room at least 30 minutes prior to dosing. The Complete Freund's Adjuvant (CFA)-thermal assay may use a three continuous day testing schedule consisting of a habituation day, a baseline day, and a test day. On day 1, animals can be brought into the testing room, labeled, and placed in their individual testing boxes on the testing apparatus. Animals may be allowed to explore this environment for at least an hour without actually being tested. After habituating, animals can be placed back in their home cages and returned to the vivarium. On day 2, animals can be brought back into the testing room and placed on the testing apparatus and allowed to calm down (typically 30-45 minutes). A basal thermal threshold should be then taken with the following procedure: once calm, a Ugo Basile plantar device is placed under the animals left hindpaw; the start button is depressed turning on a steadily increasing thermal source and a timer; when the animal reaches its thermal threshold it will flinch its hindpaw, stopping the timer and the thermal stimulus. This latency to flinch can be recorded three times for each animal, with at least 5 minutes between trials, and the mean score can be used as the animal's baseline threshold. After testing, animals can be injected intraplantarly with a 25 µg/50 µl of complete Freund's adjuvant into the left hindpaw. Animals are then retuned to their home cages and returned to the vivarium. On test day, animals can be again placed on the thermal testing apparatus and their post-CFA baselines obtained with the procedure outlined above. Animals can be pretreated with the appropriate test compound either by oral gavage or intraperitoneal injection at the desired pretreatment time (typically two hours before test onset) and then can be returned to their home cages. Thirty minutes prior to testing, animals can be placed on the apparatus again. Once the pretreatment time has elapsed, animals can be again tested with the procedure above. Data may be expressed as a percent maximal potential effect with the following formula:

((Post-Drug Mean−Pre-Drug Mean)/(Baseline Mean− Pre-Drug Mean))*100=% MPE

Statistical analysis can be performed by analysis of variance (ANOVA), with post-hoc analysis using Bonferroni compared to the vehicle group for a significant main effect. Data can be represented as mean % MPE+/−standard error for each group.

Spinal Nerve Ligation (Chung)

Animals (Naïve, male Sprague Dawley rats) weighing between 150-200 g at the start of first time testing can be obtained from Harlan (Indianapolis, Ind.). All animals may be housed under a 12/12 h light/dark cycle with lights on at 0600. Rodents can be housed two to a cage on solid bottom cages with corn cob bedding with access to food and water ad libitum. Animals may be allowed to habituate to the vivarium for at least five days before testing is begun. Surgery may be then performed based on the method described by Kim and Chung (1992). Briefly, animals can be placed under isoflurane anesthesia and placed in a sterile surgical field. The area of the lumbar spine is excised and the spinal nerves at L4-L5 are exposed. The L5 spinal nerve is identified and tightly ligated with 5-0 silk suture. The muscle may be closed with absorbable suture and the skin with wound clip. Animals may be returned to the vivarium for 7-14 days and monitored daily. On test day, animals can be brought into the testing room and placed on a wire mesh floor in individual testing chambers. They may be allowed to acclimate to the chambers until they are calm. A series of Semmes-Weinstein monofilaments (von Frey hairs) with calibrated bending forces are then applied to determine a hyperalgesic baseline following the method set forth by Chaplan et al. (1994). Briefly, filaments are applied with an increasing force (if there was not reaction to the previous stimulus) or decreasing force (if there was a reaction to the previous stimulus) until a baseline value is reached. Animals are then pretreated with the appropriate test compound either by oral gavage or intraperitoneal injection at the desired pretreatment time (typically two hours before test onset) and then returned to their home cages. Thirty minutes prior to testing, animals are placed on the apparatus again. After the pretreatment time had elapsed, the procedure above is repeated to determine drug efficacy. Data can be expressed as the mean gram force to elicit a nociceptive behavior. Statistical analysis can be performed by analysis of variance (ANOVA), with post-hoc analysis using Bonferroni compared to the vehicle group for a significant main effect

What is claimed is:

1. A compound of Formula I or II, or a pharmaceutically acceptable salt thereof,

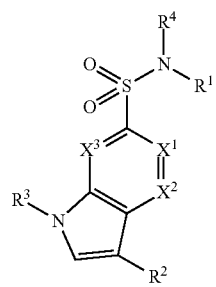

wherein:
each $X^1$, $X^2$ or $X^3$ is independently $CR^a$;
each $R^a$ is independently hydrogen, halo, $C_{1-6}$alkyl, —$OC_{1-6}$alkyl, or —CN;
each $R^b$ is independently hydrogen or $C_{1-6}$alkyl;
$R^1$ is a five or six membered heteroaryl or heterocycloalkyl group having from one to four heteroatoms independently selected from O, N or S, or a five or six membered aryl or cycloalkyl group, where the heteroaryl, heterocycloalkyl, aryl or cycloalkyl group is unsubstituted or substituted with from one to four substituents selected from halo, $C_{1-6}$alkyl, —OH, —$OC_{1-6}$alkyl or —$NR^bR^b$;
$R^2$ is a five to ten membered cycloalkyl, heterocycloalkyl, aryl or heteroaryl group, the heteroaryl or heterocycloalkl group having from one to four heteroatoms independently selected from O, N or S, and where the cycloalkyl, heterocycloalkyl, aryl or heteroaryl group is unsubstituted or substituted with from one to four substituents independently selected from —$CF_3$, —$CHF_2$, —$CF_2H$, —$OC_{1-6}$alkyl, —$OCF_3$, —$C_{1-6}$alkyl, halo, —C≡C—$R^b$, —CN, —$NR^bR^b$, —$S(=O)_2C_{1-6}$alkyl, or Y;
Y is a five or six membered heteroaryl or heterocycloalkyl group having from one to four heteroatoms independently selected from O, N or S, or six membered aryl or five or six membered cycloalkyl group, which heteroaryl, heterocycloalkyl, aryl or cycloalkyl group is unsubstituted or substituted with from one to four substituents independently selected from —$CF_3$, —$CHF_2$, —$CF_2H$, —$OC_{1-6}$alkyl, —$OCF_3$, $C_{1-6}$alkyl, halo, —C≡C—$R^b$, —CN, —$NR^bR^b$, —$S(=O)_2C_{1-6}$alkyl, —C(=O)$C_{1-6}$alkyl or Z;
Z is a three to six membered heterocycloalkyl group having from one to four heteroatoms independently selected from O, N or S;
$R^3$ is hydrogen, $C_{1-6}$alkyl, —C(=O)$C_{1-6}$alkyl, —C(=O)O$C_{1-6}$alkyl, or —$S(=O)_2C_{1-6}$alkyl; and
$R^4$ is hydrogen or $C_{1-6}$alkyl, provided that the compound of Formula I is not 1-methyl-3-(2-(1-methyl-1H-pyrazol-5-yl)-4-(trifluoromethyl)phenyl)-N-2-pyrimidinyl-1H-indole-6-sulfonamide;

3-(1-(3-azetidinyl)-1H-pyrazol-3-yl)-1-methyl-N-1,2,4-thiadiazol-5-yl-1H-indole-6-sulfonamide;

3-(2-(5-acetyl-2-thiophenyl)-4-(trifluoromethyl)phenyl)-1-methyl-N-1,2,4-thiadiazol-5-yl-1H-indole-6-sulfonamide;

1-methyl-3-(5-phenyl-2-thiophenyl)-N-1,2,4-thiadiazol-5-yl-1H-indole-6-sulfonamide;

N-(4-((1R)-1-methoxyethyl)-1,3-thiazol-2-yl)-1-methyl-3-(2-(1-methyl-1H-pyrazol-5-yl)-4-(trifluoromethyl)phenyl)-1H-indole-6-sulfonamide;

N-(4-((1S)-1-methoxyethyl)-1,3-thiazol-2-yl)-1-methyl-3-(2(1-methyl-1H-pyrazol-5-yl)-4-(trifluoromethyl)phenyl)-1H-indole-6-sulfonamide;

1-methyl-3-(4-(methylsulfonyl)phenyl)-N-1,2,4-thiadiazol-5-yl-1H-indole-6-sulfonamide;

N-(3-ethyl-1,2,4-thiadiazol-5-yl)-1-methyl-3-(241-methyl-1H-pyrazol-5-yl)-4-(trifluoromethyl)phenyl)-1H-indole-6-sulfonamide;

1-methyl-3-(4-((methylsulfonyl)amino)phenyl)-N-1,2,4-thiadiazol-5-yl-1H-indole-6-sulfonamide; or 3(1,3-dimethyl-2,4-dioxo-1,2,3,4-tetrahydro-5-pyrimidinyl)-1-methyl-N-1,2,4-thiadiazol-5-yl-1H-indole-6-sulfonamide.

2. A compound in accordance with claim 1, or a pharmaceutically acceptable salt thereof, wherein $R^4$ is hydrogen or methyl.

3. A compound in accordance with claim 1, or a pharmaceutically acceptable salt thereof, wherein $R^4$ is hydrogen.

4. A compound in accordance with claim 1, or a pharmaceutically acceptable salt thereof, wherein $X^1$ is CH; $X^2$ is CH and $X^3$ is CH.

5. A compound in accordance with claim 1, or a pharmaceutically acceptable salt thereof, wherein $R^3$ is methyl or hydrogen.

6. A compound in accordance with claim 1, or a pharmaceutically acceptable salt thereof, wherein $R^3$ is methyl.

7. A compound in accordance with claim 1, or a pharmaceutically acceptable salt thereof, wherein $R^3$ is hydrogen.

8. A compound in accordance with claim 1, or a pharmaceutically acceptable salt thereof, wherein $R^3$ is hydrogen, methyl, —C(=O)$CH_3$, —C(=O)O$CH_3$, or —$S(=O)_2CH_3$.

9. A compound in accordance with claim 1, or a pharmaceutically acceptable salt thereof, wherein $R^3$ is $C_{1-6}$alkyl.

10. A compound in accordance with claim 1, or a pharmaceutically acceptable salt thereof, wherein $R^1$ is a five or six membered heteroaryl group having from one to four heteroatoms independently selected from O, N or S.

11. A compound in accordance with claim 1, or a pharmaceutically acceptable salt thereof, wherein $R^1$ is

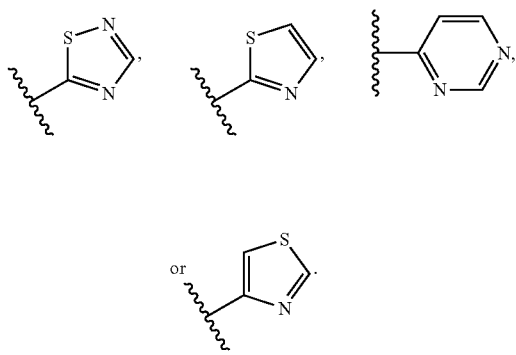

12. A compound in accordance with claim 1, or a pharmaceutically acceptable salt thereof, wherein $R^1$ is

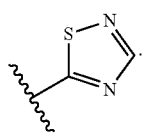

13. A compound in accordance with claim 1, or a pharmaceutically acceptable salt thereof, wherein $R^2$ is a five, six or ten membered aryl or heteroaryl group, the heteroaryl group having from one to four heteroatoms independently selected from O, N or S, and where the aryl or heteroaryl group is unsubstituted or substituted with from one to four substituents independently selected from —$CF_3$, —$CHF_2$, —$CF_2H$, —$OC_{1-6}$alkyl, —$OCF_3$, —$C_{1-6}$alkyl, halo, —C≡C—$R^b$, —CN, —$NR^bR^b$, —$S(═O)_2C_{1-6}$alkyl, or Y;
  Y is a five or six membered heteroaryl or heterocycloalkyl group having from one to four heteroatoms independently selected from O, N or S, or six membered aryl or five or six membered cycloalkyl group, which heteroaryl, heterocycloalkyl, aryl or cycloalkyl group is unsubstituted or substituted with from one to four substituents independently selected from —$CF_3$, —$CHF_2$, —$CF_2H$, —$OC_{1-6}$alkyl, —$OCF_3$, $C_{1-6}$alkyl, halo, —C≡C—$R^b$, —CN, —$NR^bR^b$, —$S(═O)_2C_{1-6}$alkyl, —$C(═O)C_{1-6}$alkyl or Z; and
  Z is a three to six membered heterocycloalkyl group having from one to four heteroatoms independently selected from O, N or S.

14. A compound in accordance with claim 1, or a pharmaceutically acceptable salt thereof, wherein $R^2$ is a six membered aryl or heteroaryl group, the heteroaryl group having from one to four heteroatoms independently selected from O, N or S, and where the aryl or heteroaryl group is unsubstituted or substituted with from one to four substituents independently selected from —$CF_3$, —$CHF_2$, —$CF_2H$, —$OC_{1-6}$alkyl, —$OCF_3$, —$C_{1-6}$alkyl, halo, —C≡C—$R^b$, —CN, —$NR^bR^b$, —$S(═O)_2C_{1-6}$alkyl, or Y;
  Y is a five or six membered heteroaryl or heterocycloalkyl group having from one to four heteroatoms independently selected from O, N or S, or six membered aryl or five or six membered cycloalkyl group, which heteroaryl, heterocycloalkyl, aryl or cycloalkyl group is unsubstituted or substituted with from one to four substituents independently selected from —$CF_3$, —$CHF_2$, —$CF_2H$, —$OC_{1-6}$alkyl, —$OCF_3$, $C_{1-6}$alkyl, halo, —C≡C—$R^b$, —CN, —$NR^bR^b$, —$S(═O)_2C_{1-6}$alkyl, —$C(═O)C_{1-6}$alkyl or Z; and
  Z is a three to six membered heterocycloalkyl group having from one to four heteroatoms independently selected from O, N or S.

15. A compound in accordance with claim 1, or a pharmaceutically acceptable salt thereof, wherein $R^2$ is a six membered aryl or heteroaryl group, the heteroaryl group having from one to four heteroatoms independently selected from O, N or S, and where the aryl or heteroaryl group is unsubstituted or substituted with from one to four substituents independently selected from —$CF_3$, —$CHF_2$, —$CF_2H$, —$OC_{1-6}$alkyl, —$OCF_3$, —$C_{1-6}$alkyl, halo, —C≡C—$R^b$, —CN, —$NR^bR^b$, —$S(═O)_2C_{1-6}$alkyl, or Y;
  Y is

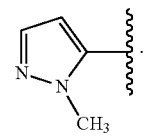

16. A compound in accordance with claim 1, or a pharmaceutically acceptable salt thereof, wherein $R^2$ is phenyl substituted with from one to three substituents independently selected from —$CF_3$, —$CHF_2$, —$CF_2H$, —$OC_{1-6}$alkyl, —$OCF_3$, —$C_{1-6}$alkyl, halo, —C≡C—$R^b$, —CN, —$NR^bR^b$, —$S(═O)_2C_{1-6}$alkyl, or Y;
  Y is a five or six membered heteroaryl group having from one to four heteroatoms independently selected from O, N or S, which heteroaryl group is unsubstituted or substituted with from one to four substituents independently selected from —$CF_3$, —$CHF_2$, —$CF_2H$, —$OC_{1-6}$alkyl, —$OCF_3$, $C_{1-6}$alkyl, halo, —C≡C—$R^b$, —CN, —$NR^bR^b$, —$S(═O)_2C_{1-6}$alkyl, —$C(═O)C_{1-6}$alkyl or Z; and
  Z is a three to six membered heterocycloalkyl group having from one to four heteroatoms independently selected from O, N or S.

17. A compound in accordance with claim 1, or a pharmaceutically acceptable salt thereof, wherein $R^2$ is

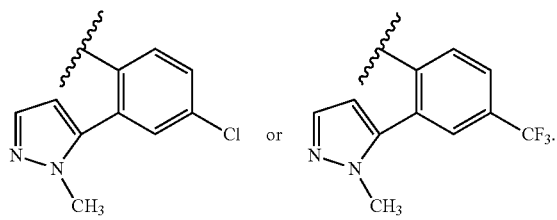 [SMILES: *c1ccc(Cl)cc1-c1ccnn1C ; *c1ccc(C(F)(F)F)cc1-c1ccnn1C]

18. A compound, or a pharmaceutically acceptable salt thereof, selected from:
  3-(4-chloro-2-(1-methyl-1H-pyrazol-5-yl)phenyl)-N-(2,4-dimethoxybenzyl)-N-(1,2,4-thiadiazol-5-yl)-1H-indole-6-sulfonamide;
  3-(4-chloro-2-(1-methyl-1H-pyrazol-5-yl)phenyl)-1-methyl-N-(1,2,4-thiadiazol-5-yl)-1H-indole-6-sulfonamide;
  1-isopropyl-3-(2-(1-methyl-1H-pyrazol-5-yl)-4-(trifluoromethyl)phenyl)-N-(1,2,4-thiadiazol-5-yl)-1H-indole-6-sulfonamide;
  1-acetyl-3-(2-(1-methyl-1H-pyrazol-5-yl)-4-(trifluoromethyl)phenyl)-N-(1,2,4-thiadiazol-5-yl) -1H-indole-6-sulfonamide;
  3-(2-(1-methyl-1H-pyrazol-5-yl)-4-(trifluoromethyl)phenyl)-N-(1,2,4-thiadiazol-5-yl)-1H-indole-6-sulfonamide;
  methyl 6-(N-(1,2,4-thiadiazol-5-yl)sulfamoyl)-3-(2-(1-methyl-1H-pyrazol-5-yl)-4-(trifluoromethyl)phenyl)-1H-indole-1-carboxylate;

3-(2-(1-methyl-1H-pyrazol-5-yl)-4-(trifluoromethyl)phenyl)-1-(methylsulfonyl)-N-(1,2,4-thiadiazol-5-yl)-1H-indole-6-sulfonamide;

1-methyl-3-(2-(1-methyl-1H-pyrazol-5-yl)-4-(trifluoromethyl)phenyl)-N-(1,2,4-thiadiazol-5-yl)-1H-indole-6-sulfonamide;

1-methyl-3-(pyridin-3-yl)-N-(1,2,4-thiadiazol-5-yl)-1H-indole-6-sulfonamide;

3-(2,5-difluorophenyl)-1-methyl-N-(1,2,4-thiadiazol-5-yl)-1H-indole-6-sulfonamide;

1-methyl-3-(2-(1-methyl-1H-pyrazol-5-yl)-4-(trifluoromethyl)phenyl)-N-(thiazol-2-yl)-1H-indole-6-sulfonamide;

1-methyl-3-(2-(1-methyl-1H-pyrazol-5-yl)-4-(trifluoromethyl)phenyl)-N-(pyrimidin-4-yl)-1H-indole-6-sulfonamide;

1-methyl-3-(2-(1-methyl-1H-pyrazol-5-yl)-4-(trifluoromethyl)phenyl)-N-(1,3,4-thiadiazol-2-yl)-1H-indole-6-sulfonamide;

1-methyl-3-(5-(prop-1-yn-1-yl)pyridin-3-yl)-N-(1,2,4-thiadiazol-5-yl)-1H-indole-6-sulfonamide;

1-methyl-3-(3-(pyridin-4-yl)-5-(trifluoromethyl)phenyl)-N-(1,2,4-thiadiazol-5-yl)-1H-indole-6-sulfonamide;

3-(2-cyano-4-(trifluoromethyl)phenyl)-1-methyl-N-(1,2,4-thiadiazol-5-yl)-1H-indole-6-sulfonamide;

3-(3-bromo-5-(trifluoromethyl)phenyl)-1-methyl-N-(1,2,4-thiadiazol-5-yl)-1H-indole-6-sulfonamide;

1-methyl-3-(2-(pyridin-4-yl)-4-(trifluoromethyl)phenyl)-N-(1,2,4-thiadiazol-5-yl)-1H-indole-6-sulfonamide;

3-(2-(1-(azetidin-3-yl)-1H-pyrazol-3-yl)-4-(trifluoromethyl)phenyl)-1-methyl-N-(1,2,4-thiadiazol-5-yl)-1H-indole-6-sulfonamide;

1-methyl-3-(2-(1-methyl-1H-pyrazol-5-yl)-4-(trifluoromethyl)phenyl)-N-(5-methyl-4-(trifluoromethyl)thiazol-2-yl)-1H-indole-6-sulfonamide;

3-(2-(1H-pyrazol-4-yl)-4-(trifluoromethyl)phenyl)-1-methyl-N-(1,2,4-thiadiazol-5-yl)-1H-indole-6-sulfonamide;

1-methyl-3-(2-(1,2,3,6-tetrahydropyridin-4-yl)-4-(trifluoromethyl)phenyl)-N-(1,2,4-thiadiazol-5-yl)-1H-indole-6-sulfonamide;

3-(2-chloro-4-(trifluoromethyl)phenyl)-1-methyl-N-(1,2,4-thiadiazol-5-yl)-1H-indole-6-sulfonamide;

3-(3-chloro-4-(trifluoromethyl)phenyl)-1-methyl-N-(1,2,4-thiadiazol-5-yl)-1H-indole-6-sulfonamide;

3-(4-fluoro-2-methoxyphenyl)-1-methyl-N-(1,2,4-thiadiazol-5-yl)-1H-indole-6-sulfonamide;

3-(3,5-dimethoxyphenyl)-1-methyl-N-(1,2,4-thiadiazol-5-yl)-1H-indole-6-sulfonamide;

3-(3-cyano-4-fluorophenyl)-1-methyl-N-(1,2,4-thiadiazol-5-yl)-1H-indole-6-sulfonamide;

3-(4-cyano-3-fluorophenyl)-1-methyl-N-(1,2,4-thiadiazol-5-yl)-1H-indole-6-sulfonamide;

1-methyl-N-(1,2,4-thiadiazol-5-yl)-3-(4-(trifluoromethoxy)phenyl)-1H-indole-6-sulfonamide;

1-methyl-N-(1,2,4-thiadiazol-5-yl)-3-(3-(trifluoromethoxy)phenyl)-1H-indole-6-sulfonamide;

3-(3-cyanophenyl)-1-methyl-N-(1,2,4-thiadiazol-5-yl)-1H-indole-6-sulfonamide;

1-methyl-3-phenyl-N-(1,2,4-thiadiazol-5-yl)-1H-indole-6-sulfonamide;

3-(2,4-dimethoxyphenyl)-1-methyl-N-(1,2,4-thiadiazol-5-yl)-1H-indole-6-sulfonamide;

1-methyl-3-(naphthalen-1-yl)-N-(1,2,4-thiadiazol-5-yl)-1H-indole-6-sulfonamide;

1-methyl-3-(quinolin-5-yl)-N-(1,2,4-thiadiazol-5-yl)-1H-indole-6-sulfonamide;

1-methyl-3-(3-(methylsulfonyl)phenyl)-N-(1,2,4-thiadiazol-5-yl)-1H-indole-6-sulfonamide;

3-(4-methoxynaphthalen-1-yl)-1-methyl-N-(1,2,4-thiadiazol-5-yl)-1H-indole-6-sulfonamide;

3-(2-chloro-4-methoxyphenyl)-1-methyl-N-(1,2,4-thiadiazol-5-yl)-1H-indole-6-sulfonamide;

3-(3,5-dimethylisoxazol-4-yl)-1-methyl-N-(1,2,4-thiadiazol-5-yl)-1H-indole-6-sulfonamide;

3-(4-bromo-2-(trifluoromethyl)phenyl)-1-methyl-N-(1,2,4-thiadiazol-5-yl)-1H-indole-6-sulfonamide;

1-methyl-N-(1,2,4-thiadiazol-5-yl)-3-(2-(trifluoromethyl)phenyl)-1H-indole-6-sulfonamide;

3-(2-amino-5-methylpyridin-3-yl)-1-methyl-N-(1,2,4-thiadiazol-5-yl)-1H-indole-6-sulfonamide;

3-(4-cyano-2-methylphenyl)-1-methyl-N-(1,2,4-thiadiazol-5-yl)-1H-indole-6-sulfonamide;

3-(3-(dimethylamino)phenyl)-1-methyl-N-(1,2,4-thiadiazol-5-yl)-1H-indole-6-sulfonamide;

1-methyl-N-(1,2,4-thiadiazol-5-yl)-3-(3-(trifluoromethyl)phenyl)-1H-indole-6-sulfonamide;

3-(4-methoxy-3-(trifluoromethyl)phenyl)-1-methyl-N-(1,2,4-thiadiazol-5-yl)-1H-indole-6-sulfonamide;

N-(3-bromo-1,2,4-thiadiazol-5-yl)-1-methyl-3-(2-(1-methyl-1H-pyrazol-5-yl)-4-(trifluoromethyl)phenyl)-1H-indole-6-sulfonamide;

3-(3-chloropyridin-4-yl)-1-methyl-N-(1,2,4-thiadiazol-5-yl)-1H-indole-6-sulfonamide;

1-methyl-3-(1-methyl-1H-pyrazol-5-yl)-N-1,2,4-thiadiazol-5-yl)-1H-indole-6-sulfonamide;

1-methyl-3-(1,2,3,4-tetrahydroisoquinolin-5-yl)-N-(1,2,4-thiadiazol-5-yl)-1H-indole-6-sulfonamide hydrochloride;

1-methyl-3-(1,2,3,4-tetrahydroisoquinolin-8-yl)-N-(1,2,4-thiadiazol-5-yl)-1H-indole-6-sulfonamide hydrochloride;

3-(1-cyclopropyl-1H-pyrazol-4-yl)-1-methyl-N-(1,2,4-thiadiazol-5-yl)-1H-indole-6-sulfonamide;

3-(5-fluoro-2-methoxypyridin-4-yl)-1-methyl-N-(1,2,4-thiadiazol-5-yl)-1H-indole-6-sulfonamide;

1-methyl-N-(1,2,4-thiadiazol-5-yl)-3-(4-(trifluoromethyl)phenyl)-1H-indole-6-sulfonamide;

1-methyl-N-(1,2,4-thiadiazol-5-yl)-3-(2-(trifluoromethoxy)phenyl)-1H-indole-6-sulfonamide;

3-(benzofuran-2-yl)-1-methyl-N-(1,2,4-thiadiazol-5-yl)-1H-indole-6-sulfonamide;

3-(3-cyano-4-methoxyphenyl)-1-methyl-N-(1,2,4-thiadiazol-5-yl)-1H-indole-6-sulfonamide;

3-(6-methoxypyridin-3-yl)-1-methyl-N-(1,2,4-thiadiazol-5-yl)-1H-indole-6-sulfonamide;

1-methyl-3-(1,2,3,4-tetrahydroisoquinolin-8-yl)-N-(1,2,4-thiadiazol-5-yl)-1H-indole-6-sulfonamide;

1-methyl-3-(2-(1,2,3,6-tetrahydropyridin-4-yl)-4-(trifluoromethyl)phenyl)-N-(thiazol-2-yl)-1H-indole-6-sulfonamide; or 1-methyl-3-(2-(1,2,3,6-tetrahydropyridin-4-yl)-4-(trifluoromethyl)phenyl)-N-(thiazol-4-yl)-1H-indole-6-sulfonamide.

19. A pharmaceutical composition comprising a compound in accordance with claim 1, or a pharmaceutically acceptable salt thereof, and a pharmaceutically acceptable excipient.

* * * * *